US008383822B2

(12) United States Patent
Allerheiligen et al.

(10) Patent No.: US 8,383,822 B2
(45) Date of Patent: Feb. 26, 2013

(54) SUBSTITUTED OXAZOLIDINONES AND THEIR USE

(75) Inventors: Swen Allerheiligen, Essen (DE); Marcus Bauser, Berlin (DE); Dirk Heimbach, Düsseldorf (DE); Stefan Heitmeier, Wülfrath (DE); Mark Jean Gnoth, Mettmann (DE); Christoph Gerdes, Köln (DE); Georges Von Degenfeld, Leverkusen (DE); Susanne Röhrig, Hilden (DE); Ulrich Rester, Wuppertal (DE); Elke Dittrich-Wengenroth, Wuppertal (DE); Uwe Saatmann, Wuppertal (DE); Adrian Tersteegen, Wuppertal (DE); Joachim Krüger, Düsseldorf (DE); Holger Paulsen, Hilden (DE)

(73) Assignee: Bayer Intellectual Property GmbH, Monheim (DE)

(*) Notice: Subject to any disclaimer, the term of this patent is extended or adjusted under 35 U.S.C. 154(b) by 178 days.

(21) Appl. No.: 12/665,729

(22) PCT Filed: Jun. 7, 2008

(86) PCT No.: PCT/EP2008/004562
§ 371 (c)(1),
(2), (4) Date: Dec. 21, 2009

(87) PCT Pub. No.: WO2008/155032
PCT Pub. Date: Dec. 24, 2008

(65) Prior Publication Data
US 2010/0184740 A1 Jul. 22, 2010

(30) Foreign Application Priority Data
Jun. 20, 2007 (DE) .................... 10 2007 028 319

(51) Int. Cl.
*A61K 31/44* (2006.01)
*C07D 413/00* (2006.01)
(52) U.S. Cl. .................................. 546/271.4; 514/340
(58) Field of Classification Search .............. None
See application file for complete search history.

(56) References Cited

U.S. PATENT DOCUMENTS

| 7,049,443 | B2 | 5/2006 | Hester, Jr. | |
|---|---|---|---|---|
| 7,157,456 | B2* | 1/2007 | Straub et al. | 514/236.8 |
| 7,265,140 | B2 | 9/2007 | Josyula et al. | |
| 7,351,823 | B2 | 4/2008 | Berwe et al. | |
| 7,576,111 | B2 | 8/2009 | Straub et al. | |
| 7,767,702 | B2 | 8/2010 | Straub et al. | |
| 8,153,670 | B2 | 4/2012 | Zhu et al. | |
| 8,198,267 | B2 | 6/2012 | Allerheiligen et al. | |
| 2003/0153610 | A1 | 8/2003 | Straub et al. | |
| 2006/0069260 | A1* | 3/2006 | Zhang et al. | 546/290 |
| 2006/0258724 | A1 | 11/2006 | Straub et al. | |
| 2007/0026065 | A1 | 2/2007 | Benke et al. | |
| 2008/0026057 | A1 | 1/2008 | Benke | |
| 2008/0200674 | A1 | 8/2008 | Straub et al. | |
| 2008/0306070 | A1 | 12/2008 | Perzborn | |
| 2010/0029651 | A1 | 2/2010 | Härter et al. | |
| 2010/0261759 | A1 | 10/2010 | Allerheiligen et al. | |
| 2010/0292230 | A1 | 11/2010 | Lerchen et al. | |

OTHER PUBLICATIONS

Simmoneau, G., et al., J. Amer. Coll. Cardiol. 2004, vol. 43, pp. 5S-12S.*
Heart Disease: A Textbook of Cardiovascular Medicine, Eugene Braunwald, 5. Auflage, 1997, W.B. Saunders Company, Philadelphia.
J. Hirsh, J. Dalen, D.R. Anderson et al., "Oral anticoagulants: Mechanism of action, clinical effectiveness, and optimal therapeutic range" Chest 2001, 119, 8S-21S.
J. Ansell, J. Hirsh, J. Dalen et al., "Managing oral anticoagulant therapy" Chest 2001, 119, 22S-38S.
P.S. Wells, A.M. Holbrook, N.R. Crowther et al., "Interactions of warfarin with drugs and food" Ann. Intern. Med. 1994, 121, 676-683.
J.H. Sohn, et al., Appl. Microbiolog. Biotechn. 2001, 57, 606-613.
T. Gladwell, Clin. Ther. 2002, 24, 38-58.
G. Escolar, Drugs of Today, 2006, 42, 223.
J. Hauptmann, J. Stürzebecher, Thrombosis Research 1999, 93, 203-241.
S.A.V. Raghavan, M. Dikshit, "Recent advances in the status and targets of antithrombotic agents" Drugs Fut. 2002, 27, 669-683.
H.A. Wieland, V. Laux, D. Kozian, M. Lorenz, "Approaches in anticoagulation: Rationales for target positioning" Curr. Opin. Investig. Drugs 2003, 4, 264-271.
U.J. Ries, W. Wienen, "Serine proteases as targets for antithrombotic therapy" Drugs Fut. 2003, 28, 355-370.
L.-A. Linkins, J.I. Weitz, "New anticoagulant therapy" Annu. Rev. Med. 2005, 56, 63-77.
A. Casimiro-Garcia et al., "Progress in the discovery of Factor Xa inhibitors", Expert Opin. Ther. Patents, 2006, 15, 119-145.
J.M. Walenga, W.P. Jeske, D. Hoppensteadt, J. Fareed, "Factor Xa Inhibitors: Today and beyond" Curr. Opin. Investig. Drugs 2003, 4, 272-281.
J. Ruef, H.A. Katus, "New antithrombotic drugs on the horizon" Expert Opin. Investig. Drugs 2003, 12, 781-797.
M.L. Quan, J.M. Smallheer, "The race to an orally active Factor Xa inhibitor: Recent advances" Curr. Opin. Drug Discovery & Development 2004, 7, 460-469.
Journal of Thrombosis and Haemostasis, 4, pp. 834-841.
International Search Report, Appl. No. PCT/EP2008/004563, dated Sep. 17, 2008.

(Continued)

*Primary Examiner* — Janet Andres
*Assistant Examiner* — Heidi Reese
(74) *Attorney, Agent, or Firm* — Karen B. King; Jonathan R. Harris; Thomas C. Blankinship

(57) ABSTRACT

The invention relates to novel substituted oxazolidinones, to processes for their preparation, to their use for the treatment and/or prophylaxis of diseases and their use for preparing medicaments for the treatment and/or prophylaxis of diseases, in particular of thromboembolic disorders.

11 Claims, No Drawings

OTHER PUBLICATIONS

International Search Report, Appl. No. PCT/EP2008/004746, dated Sep. 3, 2008.
International Search Report, Appl. No. PCT/EP2008/004562, dated Sep. 17, 2008.
Copending U.S. Appl. No. 12/665,728, filed Jun. 28, 2010.
Copending U.S. Appl. No. 12/665,718, filed Dec. 20, 2009.
Mackman:"Triggers, Targets and Treatments for Thrombosis," Nature, Feb. 2008, 451:914-918.
Roehrig, et al.:"Discovery of the Novel Antithrombotic Agent 5-Chloro-N-({(5S)-2-oxo-3-[4-(3-oxomorpholin-4-yl) phenyl]-1,3-oxazolidin-5-yl}methyl)thiophene-2-carboxamide (BAY 59/7939): An Oral, Direct Factor Xa Inhibitor," J. Med. Chem., 2005, 48(19):5900-5908.
U.S. Appl. No. 13/328,532, filed Dec. 16, 2011.
U.S. Appl. No. 12/438,097, filed Dec. 28, 2009.
U.S. Appl. No. 12/665,718, filed Dec. 20, 2009.

\* cited by examiner

SUBSTITUTED OXAZOLIDINONES AND THEIR USE

The invention relates to novel substituted oxazolidinones, to processes for their preparation, to their use for the treatment and/or prophylaxis of diseases and their use for preparing medicaments for the treatment and/or prophylaxis of diseases, in particular of thromboembolic disorders.

Blood coagulation is a protective mechanism of the organism which helps to "seal" defects in the wall of the blood vessels quickly and reliably. Thus, loss of blood can be avoided or kept to a minimum. Haemostasis after injury of the blood vessels is effected mainly by the coagulation system in which an enzymatic cascade of complex reactions of plasma proteins is triggered. Numerous blood coagulation factors are involved in this process, each of which factors converts, on activation, the respectively next inactive precursor into its active form. At the end of the cascade comes the conversion of soluble fibrinogen into insoluble fibrin, resulting in the formation of a blood clot. In blood coagulation, traditionally the intrinsic and the extrinsic system, which end in a joint reaction path, are distinguished. Here, factors Xa and IIa (thrombin) play key roles.

Factor Xa bundles the signals of the two coagulation paths since it is formed both via factor VIIa/tissue factor (extrinsic path) and via the tenase complex (intrinsic path) by conversion of factor X. The activated serine protease Xa cleaves prothrombin to thrombin.

Via a bunch of reactions, thrombin transfers the signals from the cascade to the coagulation state of the blood. Thrombin cleaves fibrinogen directly to fibrin. It activates factor XIII, which is required for stabilizing the fibrin clot, to factor XIIIa. In addition, thrombin is a potent trigger of platelet aggregation (via PAR-1 activation), which also contributes considerably to haemostasis. By activating TAFI (thrombin-activatable fibrinolysis inhibitor) to TAFIa, thrombin in a complex with thrombomodulin inhibits the dissolution of the clot. Activation of factors V and VIII potentiates the production of thrombin and thus in turn amplifies the coagulation reaction; the activated protein C, produced in a complex with thrombomodulin, antagonizes this increased thrombin production, thus preventing excessive haemostasis (thrombosis).

In addition to unbound factor X and thrombin in the blood, bound forms are also known. During the formation of a fibrin clot, thrombin and prothrombinase (factor Xa in a complex) are bound to the fibrin skeleton. These enzyme molecules are still active and cannot be inhibited by endogenous antithrombin III. Thus, in this manner, clots still have a general coagulative potential.

During the course of many cardiovascular and metabolic disorders, as a result of systemic factors, such as, for example, hyperlipidaemia, diabetes or smoking, owing to changes in the blood with stasis, such as, for example, atrial fibrillation, or owing to pathologic changes of the vascular walls, for example endothelial dysfunctions or atherosclerosis, there is an increased tendency of coagulation and platelet activation. This unwanted and excessive haemostasis can, by forming fibrin- and platelet-rich thrombi, cause thromboembolic disorders and thrombotic complications with life-threatening states.

Haemostasis is subject to a complex regulatory mechanism. Uncontrolled activation of the coagulation system or defect inhibition of the activation processes may lead to the formation of local thromboses or embolisms in vessels (arteries, veins, lymph vessels) or cardiac cavities. This may lead to serious thrombotic or thromboembolic disorders. In addition, systemic hypercoagulability may lead to consumption coagulopathy in the context of a disseminated intravasal coagulation. Thromboembolic complications are furthermore encountered in microangiopathic haemolytic anaemias, extracorporeal circulatory systems, such as haemodialysis, and also prosthetic heart valves and stents.

Thromboembolic disorders are the most frequent cause of morbidity and mortality in most industrialized countries [Heart Disease: A Textbook of Cardiovascular Medicine, Eugene Braunwald, 5th edition, 1997, W.B. Saunders Company, Philadelphia].

In the therapy and prophylaxis of thromboembolic and thrombotic disorders, anticoagulants, i.e. substances for inhibiting or preventing blood coagulation, play an essential role. For the treatment of acute thromboembolic or thrombotic disorders—in particular those where rapid and simple reduction or adjustment of anticoagulation is required (for example actue coronary syndrome, sepsis)—or disorders requiring a short-term prophylactic inhibition of the coagulation system as required (for example haemodialysis, cardioconversion), anticoagulants are administered parenterally.

The anticoagulants known from the prior art, for example substances for inhibiting or preventing blood coagulation, have various, frequently grave disadvantages. Accordingly, in practice, efficient and safe treatment methods or the prophylaxis of acute thrombotic/thromboembolic disorders is frequently found to be difficult and unsatisfactory.

In the acute therapy and prophylaxis of thromboembolic disorders, use is made, firstly, of heparin and low-molecular-weight heparins (NMH) which are administered intravenously or subcutaneously. Heparin is a mixture of highly sulphated glucosaminoglucans of animal origin (molar mass 3-40 kDa, with the highest frequency at 15 kDa; for example extracted from bovine lungs), of which, depending on the preparation, about 30% act anticoagulatively. Accordingly, the dosage is in units and has to be controlled accurately in the patient. Uncontrolled administration without monitoring results in a high risk of underdosage or overdosage and thus haemorrhages. Low-molecular-weight heparins (NMH) are prepared from unfractionated heparin (UFH). With respect to their size, they are better defined, and owing to their lower size, they have a modified side-effect profile.

The heparins do not act directly at the enzyme, but, by binding to antithrombin III (AT(III)), accelerate binding of AT(III) to coagulation factors having an AT(III) binding site. These include in particular factor Xa and thrombin (factor IIa). Whereas the potency of UFHs is approximately the same for both enzymes, the NMHs exhibit an activity spectrum which is shifted in favour of factor Xa, ultimately culminating in the pure factor Xa inhibition of the pentasaccharide fondaparinux. Under certain aspects, this indirect mechanism is disadvantageous:

In the case of diseases associated with consumption coagulopathy, the depletion of AT(III) results in heparins no longer being effective. In contrast: by administering heparins, the last reserve of free AT(III) is removed from the organism.

During the formation of a thrombus, prothrombinase (factor Xa) and thrombin are bound to the thrombus. These coagulation enzymes are active and contribute to the further development of the thrombus. Accordingly, in the risk reduction in arterial disorders, particular attention is paid to the inhibition of thrombus-bound thrombin or factor Xa. AT(III) is, as a protein, owing to its size, not able to inhibit thrombus-bound coagulation factors. Accordingly, it is not possible for heparins to contribute to this risk reduction.

In the context of the use for treating diseases such as, for example, acute coronary syndrome or sepsis, it is a particular advantage if the therapy can be discontinued short-term.

UFHs have a relatively short half-life of 30-150 minutes. Moreover, their action can be antagonized by protamine sulphate. The long half-life of the different NMHs, in particular of fondaparinux, which make it virtually impossible to simply adjust the therapy to acute situations, is disadvantageous here. In addition, the action of these substances can be antagonized only partially by protamine sulphate.

In general, when UFH is administered, there is a high risk of bleeding, where in particular cerebral bleeding and bleeding in the gastrointestinal tract may occur, and there may be thrombopenia, alopecia medicomentosa or osteoporosis [Pschyrembel, Klinisches Wörterbuch [Clinical Dictionary], 257th edition, 1994, Walter de Gruyter Verlag, page 610, key word "Heparin"; Römpp Lexikon Chemie [Römpp Chemical Encyclopaedia], Version 1.5, 1998, Georg Thieme Verlag Stuttgart, key word "Heparin"]. Low-molecular-weight heparins have—albeit with lower incidence—a similar side-effect spectrum—in particular with regard to the occurrence of HIT-II.

Associated with cardiac diseases or else septic disorders, there may be simultaneous—occasionally acute—kidney dysfunction. In these situations, substances which are eliminated via the kidneys may accumulate in the body, leading to a significantly increased risk of bleeding. Whereas in the case of UFHs, it is not necessary to adjust the dosage, the dosage of NMHs has to be adjusted. Fondaparinux is not recommended for patients with serious kidney dysfunction.

Additionally used—albeit much less frequently—are hirudin and the synthetically produced peptide bivalirudin derived therefrom, and also the low-molecular-weight substance argatroban. These are direct thrombin inhibitors exhibiting a high risk of bleeding. In cases of kidney dysfunction, the dosage of hirudin and bivalirudin has to be adjusted. Argatroban has a comparably weak antithrombotic action and is poorly water-soluble. As a result of the lacking inhibition of factor Xa, it is not possible to inhibit thrombin production within and outside of a thrombus, i.e. in the case of a highly excessive coagulation reaction, there is the risk that these substances are "titred out".

Further substances which can be administered parenterally are in development. These are substances which inhibit either factor Xa or thrombin, thus inhibiting either thrombin production or thrombin activity.

In addition, there are substances which are used or developed for oral therapy. Owing to their activity profile and physicochemical profile (poor solubility, slow onset of action, long half-life) they are of little, if any, use for treatment in acute situations. Such a class of anticoagulants are the vitamin K antagonists. These include, for example, 1,3-indanediones, but especially compounds such as warfarin, phenprocoumone, dicumarole and other coumarine derivatives which unselectively inhibit the synthesis of various products of certain vitamin-K-dependent coagulation factors in the liver. Owing to the mechanism of action, the onset of the activity is very slow (latency time to onset of action 36 to 48 hours). The compounds can be administered orally; however, owing to the high risk of bleeding and the narrow therapeutic index, complicated individual adjustment and observation of the patient is required. In addition, further side-effects such as gastrointestinal dysfunctions, hair loss and skin necroses, have been described.

Other anti-thrombin or anti-factor-Xa substances which are in development for oral therapy have a solubility which is too low for parenteral therapy or have—which is desirable for oral therapy—a long half-life, which does not allow a quick reaction to changes.

Recently, approaches have been described where low-molecular-weight thrombin and factor Xa inhibitors were tested in vitro and in vivo in various mixing ratios. Here, a strong synergistic potential was found. Tanogitran is a low-molecular-weight substance which has been described to inhibit, in vitro, both thrombin and factor Xa, but which has a strong preference for thrombin inhibition. A substantial fraction of tanogitran is excreted unchanged via the kidneys, which makes it likely that the dosage has to be adjusted in case of kidney insufficiency.

For antithrombotic medicaments, the therapeutic width is of central importance: The distance between the therapeutically active dose for coagulation inhibition and the dose where bleeding may occur should be as big as possible so that maximum therapeutic activity is achieved at a minimum risk profile.

As shown by the experiments with mixtures of low-molecular-weight thrombin and factor Xa inhibitors, compounds which inhibit both thrombin and factor Xa would, by virtue of their dual character, have a particularly strong synergism, thus being particularly effective in controlling the formation of thrombi. In this manner, the compounds inhibit the two key enzymes of the coagulation cascade, without completely blocking the individual enzymes. The remaining rest of factor Xa and thrombin results in an intact haemostasis and thus a particularly advantageous therapeutic width. In an arteriovenous shunt model in rabbits, it was possible to demonstrate that coadministration of only weakly antithrombotically active dosages of the selective factor Xa inhibitor PD0313052 and the selective thrombin inhibitor argatroban results in a strong superadditive antithrombotic effect. In addition, when the individual doses with the maximum synergistic effect were combined, no increased bleeding was observed. These observations allow the conclusion to be drawn that simultaneous inhibition of thrombin and factor Xa increases the therapeutic width with respect to the distance between antithrombotic action and bleeding risk (Journal of Thrombosis and Haemostasis, 4: 834-841).

This synergism is particularly pronounced when the prothrombin time as a function of the substance concentration is studied by direct comparison with pure factor Xa and thrombin inhibitors. This strong effect on the two key enzymes of the coagulation cascade is considered to be particularly advantageous when a high risk of thrombi formation is present, or when the formation of thrombi may result in a fatal disease. Both are relevant, for example, in the case of atherothrombotic disorders of the acute coronary syndrome type or the situation after an acute myocardial infarction.

Furthermore, in contrast to heparins, hirudin and vitamin K antagonists, compounds inhibiting both thrombin and factor Xa would also be active against coagulation factors bound to fibrin clots. The limitation of the thrombotic potential of an already existing clot is a critical point in the prevention of arterial occlusion. This is achieved particularly effectively by inhibiting both the present thrombin activity and the formation of new thrombin in the clot. Whereas a pure thrombin inhibitor cannot prevent the avalanche-like thrombin production by the clot-bound factor Xa-containing prothrombinase complex and the inhibitory effect can thus be overcompensated in a highly stimulated coagulation by the large amount of thrombin produced, pure factor Xa inhibitors are not capable of inhibiting the thrombin activity already present. Since inhibition is likewise not possible by physiological mechanisms, this clot-bound thrombin poses a particularly large risk. In contrast, dual compounds, i.e. compounds inhibiting both thrombin and factor Xa, are capable of inhibiting both the thrombin production and the thrombin activity on clots, thus also preventing a potential clot growth.

Oxazolidinones as non-peptidic low-molecular-weight factor Xa inhibitors are described in WO 01/47919.

Accordingly, it is an object of the present invention to provide dual compounds, i.e. compounds which inhibit both thrombin and factor Xa and which, by inhibiting thrombin production and thrombin activity on clots, prevent their potential growth, which have a broad therapeutic window and good solubility in water and physiological media, for controlling diseases, in particular thromboembolic disorders, in humans and animals.

The invention provides compounds of the formula

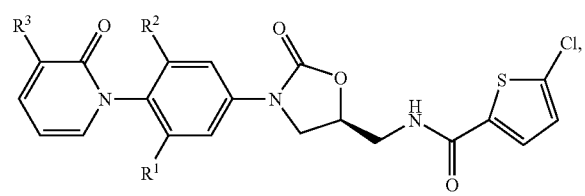

(I)

in which
$R^1$ represents chlorine, trifluoromethoxy, methyl, ethyl, n-propyl, methoxy, methoxymethyl or ethoxymethyl,
$R^2$ represents hydrogen or methyl,
and
$R^3$ represents a group of the formula

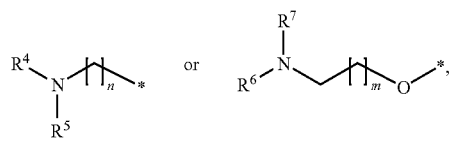

where
* is the point of attachment to the oxopyridine ring,
n represents the number 1, 2, 3 or 4,
m represents the number 1 or 2,
$R^4$ represents hydrogen, methyl, ethyl, cyclopropyl, cyclobutyl, 2-hydroxyeth-1-yl, 3-hydroxyprop-1-yl, 2-methoxyeth-1-yl, 3-methoxyprop-1-yl, 4-hydroxycyclohex-1-yl, tetrahydrofuran-2-ylmethyl or 1,4-dioxan-2-ylmethyl,
$R^5$ represents hydrogen, methyl or ethyl,
or
$R^4$ and $R^5$ together with the nitrogen atom to which they are attached form a pyrrolidin-1-yl ring, a 2-methoxymethylpyrrolidin-1-yl ring, a morpholin-4-yl ring, a 1,1-dioxothiomorpholin-4-yl ring, a 1,4-oxazepan-4-yl ring, a 4-methylpiperazin-1-yl or a 4-hydroxypiperidin-1-yl ring,
$R^6$ represents hydrogen, methyl, ethyl, cyclopropyl, cyclobutyl, 2-hydroxyeth-1-yl, 3-hydroxyprop-1-yl, 2-methoxyeth-1-yl, 3-methoxyprop-1-yl, 4-hydroxycyclohex-1-yl, tetrahydrofuran-2-ylmethyl or 1,4-dioxan-2-ylmethyl,
$R^7$ represents hydrogen, methyl or ethyl,
$R^6$ and $R^7$ together with the nitrogen atom to which they are attached form a pyrrolidin-1-yl ring, a 2-methoxymethylpyrrolidin-1-yl ring, a morpholin-4-yl ring, a 1,1-dioxothiomorpholin-4-yl ring, a 1,4-oxazepan-4-yl ring, a 4-methylpiperazin-1-yl or a 4-hydroxypiperidin-1-yl ring,
and their salts, their solvates and the solvates of their salts.

Compounds according to the invention are the compounds of the formula (I) and their salts, solvates and solvates of the salts, the compounds, comprised by formula (I), of the formulae mentioned below and their salts, solvates and solvates of the salts and the compounds, comprised by formula (I), mentioned below as exemplary embodiments and their salts, solvates and solvates of the salts if the compounds, comprised by formula (I), mentioned below are not already salts, solvates and solvates of the salts.

Depending on their structure, the compounds according to the invention can exist in stereoisomeric forms (enantiomers, diastereomers). Accordingly, the invention comprises the enantiomers or diastereomers and their respective mixtures. From such mixtures of enantiomers and/or diastereomers, it is possible to isolate the stereoisomerically uniform components in a known manner.

If the compounds according to the invention can be present in tautomeric forms, the present invention comprises all tautomeric forms.

In the context of the present invention, preferred salts are physiologically acceptable salts of the compounds according to the invention. The invention also comprises salts which for their part are not suitable for pharmaceutical applications, but which can be used, for example, for isolating or purifying the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalene disulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of customary bases, such as, by way of example and by way of preference, alkali metal salts (for example sodium salts and potassium salts), alkaline earth metal salts (for example calcium salts and magnesium salts) and ammonium salts, derived from ammonia or organic amines having 1 to 16 carbon atoms, such as, by way of example and by way of preference, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

In the context of the invention, solvates are those forms of the compounds according to the invention which, in solid or liquid state, form a complex by coordination with solvent molecules. Hydrates are a specific form of the solvates where the coordination is with water. In the context of the present invention, preferred solvates are hydrates.

Moreover, the present invention also comprises prodrugs of the compounds according to the invention. The term "prodrugs" includes compounds which for their part may be biologically active or inactive but which, during the time they spend in the body, are converted into compounds according to the invention (for example metabolically or hydrolytically).

In the formulae of the group which may represent $R^3$, the end point of the line which is marked by an * is not a carbon atom or a $CH_2$ group, but is part of the bond to the atom to which $R^3$ is attached.

Preference is given to compounds of the formula (I) in which
$R^1$ represents chlorine, trifluoromethoxy, methyl, ethyl, n-propyl, methoxy or methoxymethyl,
$R^2$ represents hydrogen or methyl,
and
$R^3$ represents a group of the formula $$R^4\diagdown\underset{R^5}{N}-(\phantom{x})_n-* \quad \text{or} \quad R^6-\underset{|}{\overset{R^7}{N}}-(\phantom{x})_m-O-*,$$

where
* is the point of attachment to the oxopyridine ring,
n is the number 1, 2 or 3,
m represents the number 1 or 2,
$R^4$ represents hydrogen, methyl, ethyl, cyclopropyl, cyclobutyl, 2-hydroxyeth-1-yl, 3-hydroxyprop-1-yl, 2-methoxyeth-1-yl, 3-methoxyprop-1-yl, 4-hydroxycyclohex-1-yl, tetrahydrofuran-2-ylmethyl or 1,4-dioxan-2-ylmethyl,
$R^5$ represents hydrogen, methyl or ethyl,
or
$R^4$ and $R^5$ together with the nitrogen atom to which they are attached form a pyrrolidin-1-yl ring, a 2-methoxymethylpyrrolidin-1-yl ring, a morpholin-4-yl ring, a 1,1-dioxothiomorpholin-4-yl ring, a 1,4-oxazepan-4-yl ring, a 4-methylpiperazin-1-yl or a 4-hydroxypiperidin-1-yl ring,
$R^6$ represents hydrogen, methyl, ethyl, cyclopropyl, cyclobutyl, 2-hydroxyeth-1-yl, 3-hydroxyprop-1-yl, 2-methoxyeth-1-yl, 3-methoxyprop-1-yl, 4-hydroxycyclohex-1-yl, tetrahydrofuran-2-ylmethyl or 1,4-dioxan-2-ylmethyl,
$R^7$ represents hydrogen, methyl or ethyl,
$R^6$ and $R^7$ together with the nitrogen atom to which they are attached form a pyrrolidin-1-yl ring, a 2-methoxymethylpyrrolidin-1-yl ring, a morpholin-4-yl ring, a 1,1-dioxothiomorpholin-4-yl ring, a 1,4-oxazepan-4-yl ring, a 4-methylpiperazin-1-yl or a 4-hydroxypiperidin-1-yl ring,
and their salts, their solvates and the solvates of their salts.

Preference is also given to compounds of the formula (I) in which
$R^1$ represents methyl, ethyl, n-propyl, methoxy or methoxymethyl,
$R^2$ represents hydrogen or methyl,
and
$R^3$ represents a group of the formula $$R^4\diagdown\underset{R^5}{N}-(\phantom{x})_n-* \quad \text{or} \quad R^6-\underset{|}{\overset{R^7}{N}}-(\phantom{x})_m-O-*,$$

where
* is the point of attachment to the oxopyridine ring,
n is the number 1, 2 or 3,
m represents the number 1 or 2,
$R^4$ represents hydrogen, methyl, ethyl, cyclopropyl, cyclobutyl, 2-hydroxyeth-1-yl, 3-hydroxyprop-1-yl, 2-methoxyeth-1-yl, 3-methoxyprop-1-yl, 4-hydroxycyclohex-1-yl, tetrahydrofuran-2-ylmethyl or 1,4-dioxan-2-ylmethyl,
$R^5$ represents hydrogen, methyl or ethyl,
$R^6$ represents hydrogen, methyl, ethyl, cyclopropyl, cyclobutyl, 2-hydroxyeth-1-yl, 3-hydroxyprop-1-yl, 2-methoxyeth-1-yl, 3-methoxyprop-1-yl, 4-hydroxycyclohex-1-yl, tetrahydrofuran-2-ylmethyl or 1,4-dioxan-2-ylmethyl,
$R^7$ represents hydrogen, methyl or ethyl,
and their salts, their solvates and the solvates of their salts.

Preference is also given to compounds of the formula (I) in which
$R^1$ represents methyl, ethyl, n-propyl, methoxy or methoxymethyl,
$R^2$ represents hydrogen,
or
$R^1$ represents methyl,
$R^2$ represents methyl,
and
$R^3$ represents a group of the formula $$R^4\diagdown\underset{R^5}{N}-(\phantom{x})_n-* \quad \text{or} \quad R^6-\underset{|}{\overset{R^7}{N}}-(\phantom{x})_m-O-*,$$

where
* is the point of attachment to the oxopyridine ring,
n represents the number 1, 2 or 3,
m represents the number 1 or 2,
$R^4$ represents hydrogen, cyclopropyl, cyclobutyl, 2-hydroxyeth-1-yl, 3-hydroxyprop-1-yl or 4-hydroxycyclohex-1-yl,
$R^5$ represents hydrogen,
$R^6$ represents hydrogen, cyclopropyl, cyclobutyl, 2-hydroxyeth-1-yl, 3-hydroxyprop-1-yl or 4-hydroxycyclohex-1-yl,
$R^7$ represents hydrogen,
and their salts, their solvates and the solvates of their salts.

Preference is also given to compounds of the formula (I) in which
$R^1$ represents methyl, methoxy or methoxymethyl,
$R^2$ represents hydrogen,
or
$R^1$ represents methyl,
$R^2$ represents methyl,
and
$R^3$ represents a group of the formula $$R^4\diagdown\underset{R^5}{N}-(\phantom{x})_n-* \quad \text{or} \quad R^6-\underset{|}{\overset{R^7}{N}}-(\phantom{x})_m-O-*,$$

where
* is the point of attachment to the oxopyridine ring,
n represents the number 2,
m represents the number 1,
$R^4$ represents 2-hydroxyeth-1-yl or 4-hydroxycyclohex-1-yl,
$R^5$ represents hydrogen,
$R^6$ represents 2-hydroxyeth-1-yl or 4-hydroxycyclohex-1-yl,
$R^7$ represents hydrogen,
and their salts, their solvates and the solvates of their salts.

Preference is also given to compounds of the formula (I) in which
$R^1$ represents methyl or methoxy,
$R^2$ represents hydrogen,
or
$R^1$ represents methyl,
$R^2$ represents methyl,
and
$R^3$ represents a group of the formula

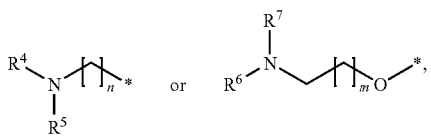

where
* is the point of attachment to the oxopyridine ring,
n represents the number 2,
m represents the number 1,
$R^4$ represents 2-hydroxyeth-1-yl or 4-hydroxycyclohex-1-yl,
$R^5$ represents hydrogen,
$R^6$ represents 2-hydroxyeth-1-yl or 4-hydroxycyclohex-1-yl,
$R^7$ represents hydrogen,
and their salts, their solvates and the solvates of their salts.

Preference is also given to compounds of the formula (I) in which
$R^1$ represents methyl, methoxy or methoxymethyl,
$R^2$ represents hydrogen,
or
$R^1$ represents methyl,
$R^2$ represents methyl,
and
$R^3$ represents a group of the formula

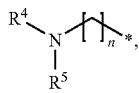

where
* is the point of attachment to the oxopyridine ring,
n is the number 2,
$R^4$ is 2-hydroxyeth-1-yl or 4-hydroxycyclohex-1-yl,
$R^5$ is hydrogen,
and their salts, their solvates and the solvates of their salts.

Preference is also given to compounds of the formula (I) in which
$R^1$ represents methoxymethyl,
$R^2$ represents hydrogen,
or
$R^1$ represents methyl,
$R^2$ represents methyl,
and
$R^3$ represents a group of the formula

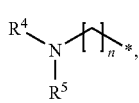

where
* is the point of attachment to the oxopyridine ring,
n represents the number 2,
$R^4$ represents 2-hydroxyeth-1-yl or 4-hydroxycyclohex-1-yl,
$R^5$ represents hydrogen,
and their salts, their solvates and the solvates of their salts.

Preference is also given to compounds of the formula (I) in which
$R^1$ represents methyl,
$R^2$ represents hydrogen,
or
$R^1$ represents methyl,
$R^2$ represents methyl,
and
$R^3$ represents a group of the formula

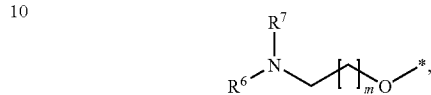

where
* is the point of attachment to the oxopyridine ring,
m represents the number 1,
$R^6$ represents 2-hydroxyeth-1-yl or 4-hydroxycyclohex-1-yl,
$R^7$ represents hydrogen,
and their salts, their solvates and the solvates of their salts.

Preference is also given to compounds of the formula (I) in which n represents the number 2.
Preference is also given to compounds of the formula (I) in which m represents the number 1.
Preference is also given to compounds of the formula (I) in which $R^1$ represents methyl, methoxy or methoxymethyl.
Preference is also given to compounds of the formula (I) in which $R^2$ represents hydrogen.
Preference is also given to compounds of the formula (I) in which $R^1$ represents methyl and $R^2$ represents hydrogen.
Preference is also given to compounds of the formula (I) in which $R^1$ represents methyl and $R^2$ represents methyl.
Preference is also given to compounds of the formula (I) in which $R^4$ represents 2-hydroxyeth-1-yl or 4-hydroxycyclohex-1-yl.
Preference is also given to compounds of the formula (I) in which $R^5$ represents hydrogen.
Preference is also given to compounds of the formula (I) in which $R^6$ represents 2-hydroxyeth-1-yl or 4-hydroxycyclohex-1-yl.
Preference is also given to compounds of the formula (I) in which $R^7$ represents hydrogen.
Preference is also given to compounds of the formula (I) in which
$R^1$ represents methyl, ethyl, n-propyl, methoxy or methoxymethyl,
$R^2$ represents hydrogen or methyl,
and
$R^3$ represents a group of the formula

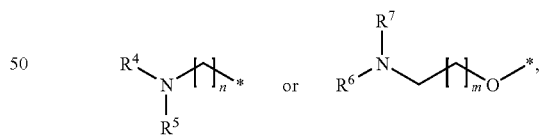

where
* is the point of attachment to the oxopyridine ring,
n represents the number 1, 2 or 3,
m represents the number 1 or 2,
$R^4$ represents methyl, ethyl, cyclopropyl, cyclobutyl, 2-methoxyeth-1-yl, 3-methoxyprop-1-yl, tetrahydrofuran-2-ylmethyl or 1,4-dioxan-2-ylmethyl,
$R^5$ represents hydrogen, methyl or ethyl,
or
$R^4$ and $R^5$ together with the nitrogen atom to which they are attached form a pyrrolidin-1-yl ring, a 2-methoxymethylpyrrolidin-1-yl ring, a morpholin-4-yl ring, a 1,1-dioxothiomorpholin-4-yl ring, a 1,4-oxazepan-4-yl ring, a 4-methylpiperazin-1-yl or a 4-hydroxypiperidin-1-yl ring, $R^6$ represents methyl, ethyl, cyclopropyl, cyclobutyl, 2-methoxyeth-1-yl, 3-methoxyprop-1-yl, tetrahydrofuran-2-ylmethyl or 1,4-dioxan-2-ylmethyl, $R^7$ represents hydrogen, methyl or ethyl, $R^6$ and $R^7$ together with the nitrogen atom to which they are attached form a pyrrolidin-1-yl ring, a 2-methoxymethylpyrrolidin-1-yl ring, a morpholin-4-yl ring, a 1,1-dioxothiomorpholin-4-yl ring, a 1,4-oxazepan-4-yl ring, a 4-methylpiperazin-1-yl or a 4-hydroxypiperidin-1-yl ring, and their salts, their solvates and the solvates of their salts.

Preference is also given to compounds of the formula (I) in which $R^1$ represents methyl, ethyl, n-propyl, methoxy or methoxymethyl, $R^2$ represents hydrogen, or $R^1$ represents methyl, $R^2$ represents methyl, and $R^3$ represents a group of the formula

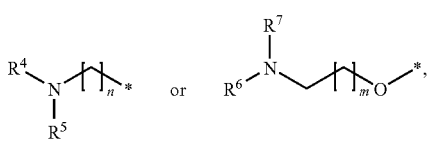

where

* is the point of attachment to the oxopyridine ring, n represents the number 1, 2 or 3, m represents the number 1 or 2, $R^4$ represents methyl, ethyl or cyclopropyl, $R^5$ represents hydrogen, methyl or ethyl, or $R^4$ and $R^5$ together with the nitrogen atom to which they are attached form a morpholin-4-yl ring, a 4-methylpiperazin-1-yl or a 4-hydroxypiperidin-1-yl ring, $R^6$ represents cyclopropyl, cyclobutyl, 2-methoxyeth-1-yl, tetrahydrofuran-2-ylmethyl or 1,4-dioxan-2-ylmethyl, $R^7$ represents hydrogen, methyl or ethyl, $R^6$ and $R^7$ together with the nitrogen atom to which they are attached form a pyrrolidin-1-yl ring, a 2-methoxymethylpyrrolidin-1-yl ring, a 1,1-dioxothiomorpholin-4-yl ring, a 1,4-oxazepan-4-yl ring or a 4-methylpiperazin-1-yl ring, and their salts, their solvates and the solvates of their salts.

Preference is also given to compounds of the formula (I) in which $R^1$ represents methyl, methoxy or methoxymethyl, $R^2$ represents hydrogen, or $R^1$ represents methyl, $R^2$ represents methyl, and $R^3$ represents a group of the formula

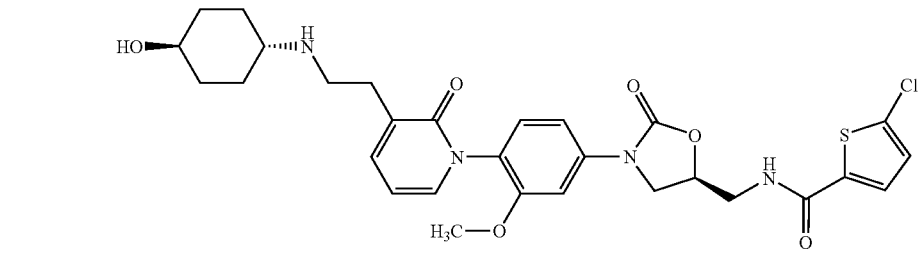

where

* is the point of attachment to the oxopyridine ring, n represents the number 1, 2 or 3, m represents the number 1 or 2, $R^4$ represents methyl or cyclopropyl, $R^5$ represents hydrogen or methyl, or $R^4$ and $R^5$ together with the nitrogen atom to which they are attached form a 4-methylpiperazin-1-yl or a 4-hydroxypiperidin-1-yl ring, $R^6$ represents cyclopropyl, cyclobutyl or 2-methoxyeth-1-yl, $R^7$ represents hydrogen or methyl, $R^6$ and $R^7$ together with the nitrogen atom to which they are attached form a pyrrolidin-1-yl ring, a 2-methoxymethylpyrrolidin-1-yl ring or a 4-methylpiperazin-1-yl ring, and their salts, their solvates and the solvates of their salts.

Particular preference is also given to the compound 5-chloro-N-{[(5S)-3-{4-[3-{2-[(trans-4-hydroxycyclohexyl)amino]ethyl}-2-oxopyridin-1(2H)-yl]-3-methoxyphenyl}-2-oxo-1,3-oxazolidin-5-yl]methyl}thiophene-2-carboxamide of the formula and its salts, its solvates and the solvates of its salts. The compound is described in Example 6.

Particular preference is also given to the compound 5-chloro-N-{[(5S)-3-{4-[3-{2-[(2-hydroxyethyl)amino]ethyl}-2-oxopyridin-1(2H)-yl]-3-(methoxymethyl)phenyl}-2-oxo-1,3-oxazolidin-5-yl]ethyl}thiophene-2-carboxamide of the formula

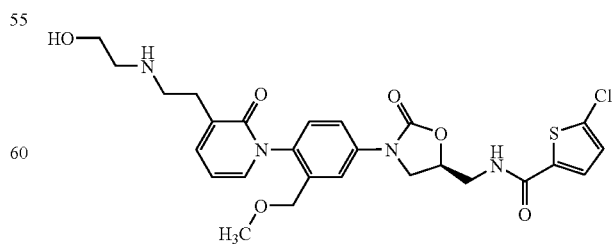

and its salts, its solvates and the solvates of its salts. The compound is described in Example 9.

Particular preference is also given to the compound 5-chloro-N-{[(5S)-3-{4-[3-{2-[(trans-4-hydroxycyclohexyl)amino]ethyl}-2-oxopyridin-1(2H)-yl]-3-(methoxymethyl)phenyl}-2-oxo-1,3-oxazolidin-5-yl]methyl}thiophene-2-carboxamide of the formula

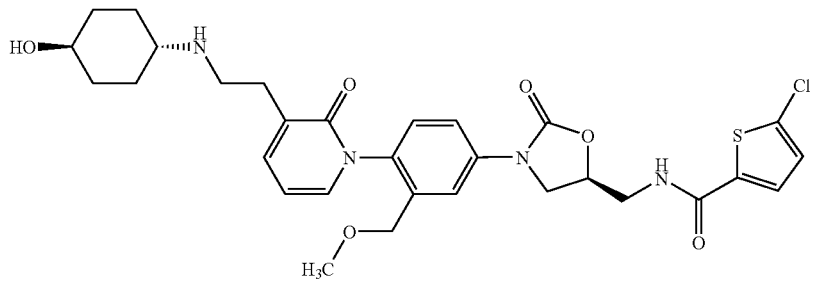 [SMILES: COCc1cc(N2C[C@H](CNC(=O)c3ccc(Cl)s3)OC2=O)ccc1-n1cccc(CCN[C@H]2CC[C@H](O)CC2)c1=O]

and its salts, its solvates and the solvates of its salts. The compound is described in Example 10.

Particular preference is also given to the compound 5-chloro-N-{[(5S)-3-{4-[3-{2-[(trans-4-hydroxycyclohexyl)amino]ethoxy}-2-oxopyridin-1(2H)-yl]-3-methylphenyl}-2-oxo-1,3-oxazolidin-5-yl]methyl}thiophene-2-carboxamide of the formula

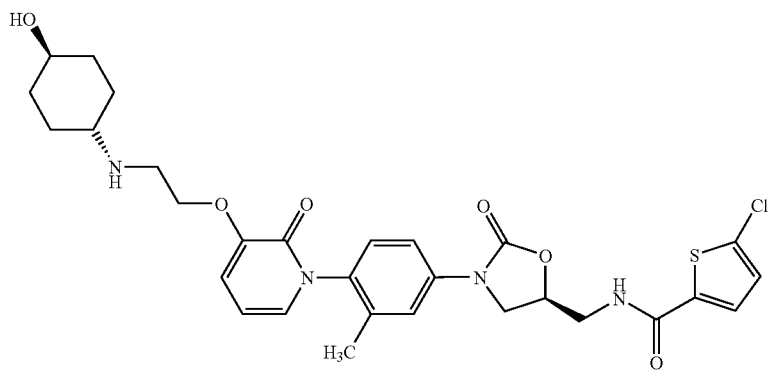

and its salts, its solvates and the solvates of its salts. The compound is described in Example 21.

Particular preference is also given to the compound 5-chloro-N-{[(5S)-3-{4-[3-{2-[(2-hydroxyethyl)amino]ethyl}-2-oxopyridin-1(2H)-yl]-3,5-dimethylphenyl}-2-oxo-1,3-oxazolidin-5-yl]methyl}thiophene-2-carboxamide of the formula

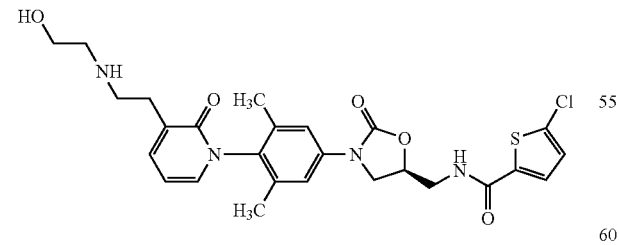

and its salts, its solvates and the solvates of its salts. The compound is described in Example 37.

Particular preference is also given to the compound 5-chloro-N-{[(5S)-3-{4-[3-{2-[(trans-4-hydroxycyclohexyl)amino]ethyl}-2-oxopyridin-1(2H)-yl]-3,5-dimethylphenyl}-2-oxo-1,3-oxazolidin-5-yl]methyl}thiophene-2-carboxamide of the formula

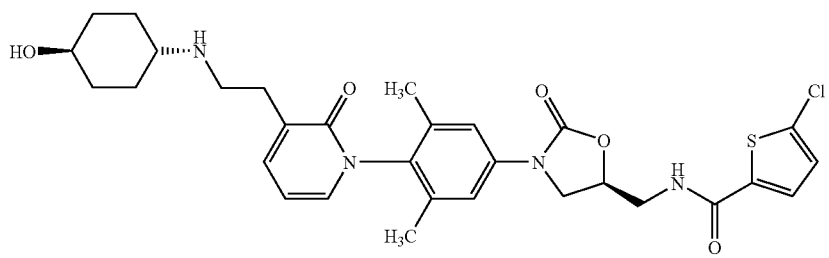

and its salts, its solvates and the solvates of its salts. The compound is described in Example 38.

The specific radical definitions given in the respective combinations or preferred combinations of radicals are, independently of the respective given combination of radicals, also replaced by any of the radical definitions of other combinations.

Very particular preference is given to combinations of two or more of the preferred ranges mentioned above.

The invention furthermore provides a process for preparing the compounds of the formula (I), or the salts, solvates or solvates of the salts thereof, wherein

[A] a compound of the formula

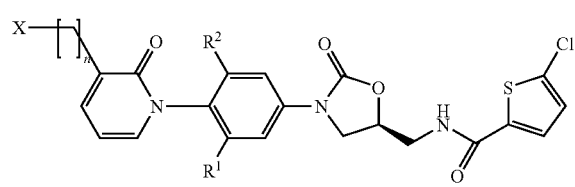
(II)

in which n, R¹ and R² have the meaning given above, and
X represents hydroxyl or bromine,
is reacted with a compound of the formula

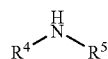
(III)

in which R⁴ and R⁵ have the meaning given above,
to give a compound of the formula

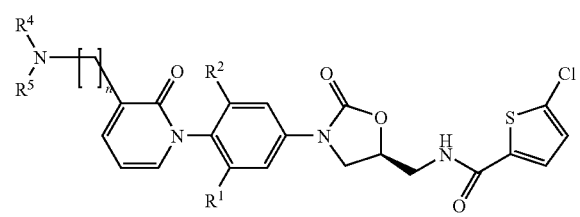
(Ia)

in which n, R¹, R², R⁴ and R⁵ have the meaning given above, or

[B] a compound of the formula

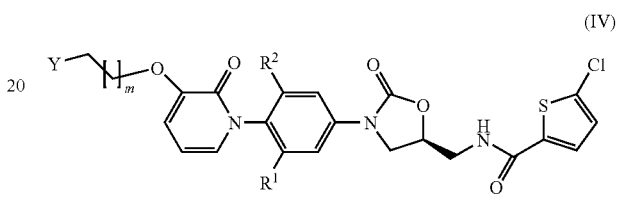
(IV)

in which m, R¹ and R² have the meaning given above, and
Y represents hydroxyl or chlorine,
is reacted with a compound of the formula

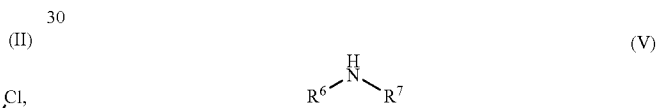
(V)

in which R⁶ and R⁷ have the meaning given above,
to give a compound of the formula

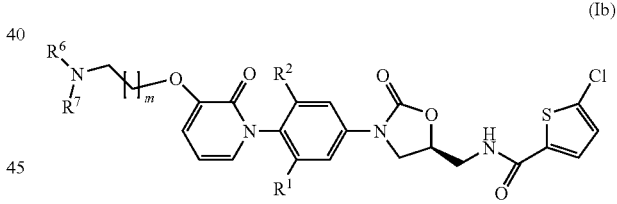
(Ib)

in which m, R¹, R², R⁶ and R⁷ have the meaning given above.

The compounds of the formulae (Ia) and (Ib) form the compounds of the formula (I).

The free base of the salts can be obtained, for example, by chromatograpy on a reversed phase column using an acetonitrile/water gradient with addition of a base, in particular by using an RP18 Phenomenex Luna C18(2) column and diethylamine as base, or by dissolving the salts in an organic solvent and extracting with aqueous solutions of basic salts such as sodium bicarbonate.

The invention furthermore provides a process for preparing the compounds of the formula (I) or solvates thereof wherein salts of the compounds or solvates of the salts of the compounds are converted by chromatography with addition of a base into the compounds.

If X is hydroxyl, the reaction according to process [A] is generally carried out in inert solvents in the presence of trifluoromethanesulphonic anhydride, if appropriate in the presence of a base, preferably in a temperature range of from −78° C. to room temperature at atmospheric pressure.

Inert solvents are, for example, dichloromethane, diethyl ether, nitromethane, 1,2-dichloroethane or acetonitrile; preference is given to dichloromethane.

Bases are, for example, 2,6-dimethylpyridine, pyridine, 2,6-di-tert-butyl-4-methylpyridine, diisopropylethylamine, 2,6-lutidine, trimethylamine, preference is given to 2,6-dimethylpyridine.

If X is bromine, the reaction according to process [A] is generally carried out in inert solvents, preferably in a temperature range of from −78° C. to room temperature at atmospheric pressure.

Inert solvents are, for example, dimethylformamide.

If Y is hydroxyl, the reaction according to process [B] is generally carried out in inert solvents, in the presence of trifluoromethanesulphonic anhydride, if appropriate in the presence of a base, preferably in a temperature range of from −78° C. to room temperature at atmospheric pressure.

Inert solvents are, for example, dichloromethane, diethyl ether, nitromethane, 1,2-dichloroethane or acetonitrile; preference is given to dichloromethane.

Bases are, for example, 2,6-dimethylpyridine, pyridine, 2,6-di-tert-butyl-4-methylpyridine, diisopropylethylamine, 2,6-lutidine, trimethylamine, preference is given to 2,6-dimethylpyridine.

If Y is chlorine, the reaction according to process [B] is generally carried out in inert solvents, if appropriate in the presence of a halogen salt, preferably in a temperature range of from room temperature to reflux of the solvent at atmospheric pressure.

Inert solvents are, for example, 1,2-dimethoxyethane.

A halogen salt is, for example, sodium iodide.

The compounds of the formulae (III) and (V) are known or can be synthesized according to known processes from the corresponding starting materials.

The compounds of the formula (II) in which X represents hydroxyl are known or can be prepared by reacting the compound of the formula

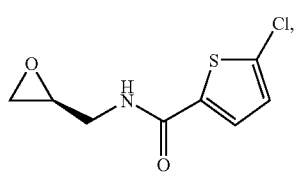

(VI)

in the first step with compounds of the formula

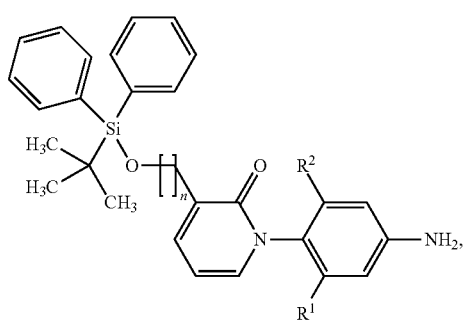

(VII)

in which n, $R^1$ and $R^2$ have the meaning given above, to give compounds of the formula

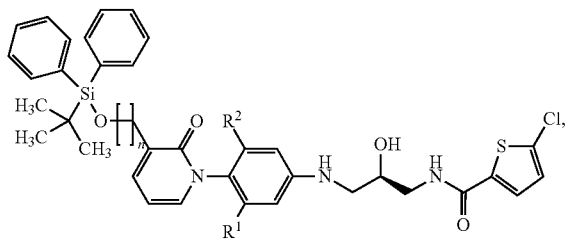

(VIII)

in which n, $R^1$ and $R^2$ have the meaning given above, cyclizing, in the second step, in the presence of phosgene or phosgene equivalents such as, for example, carbonyldiimidazole (CU), and, in the third step, removing the silyl group, giving the compounds of the formula The reaction of the first step is generally carried out in inert solvents, in the presence of a Lewis acid, preferably in a temperature range of from room temperature to reflux of the solvent at atmospheric pressure.

Inert solvents are, for example, polar aprotic solvents, such as, for example, acetonitrile, butyronitrile, dichloromethane or chloroform; preference is given to acetonitrile.

Lewis acids are, for example, magnesium perchlorate, ytterbium(III) trifluoromethanesulphonate, lithium bromide, magnesium triflate or aluminium trichloride; preference is given to magnesium perchlorate.

The reaction of the second step is generally carried out in inert solvents, in the presence of a base, preferably in a temperature range of from room temperature to reflux of the solvent at atmospheric pressure.

Inert solvents are, for example, polar aprotic solvents, such as, for example, acetonitrile or butyronitrile.

Bases are, for example, strong tertiary amine bases, such as, for example, 4-N,N-dimethylaminopyridine.

Preference is given to the reaction with N,N'-carbonyldiimidazole as carbonic acid equivalent with addition of 4-N,N-dimethylaminopyridine as base.

The reaction of the third step is carried out by methods known to the person skilled in the art, for example by reaction with tetrabutylammonium fluoride in a solvent, such as, for example, tetrahydrofuran, or by reaction with hydrogen chloride in methanol, preferably in a temperature range of from room temperature to reflux of the solvent at atmospheric pressure.

The compound of the formula (VI) is known or can be synthesized by known processes from the corresponding starting materials.

In an alternative process, compounds of the formula (II) in which X represents hydroxy can be prepared by reacting the compounds of the formula (XVI)

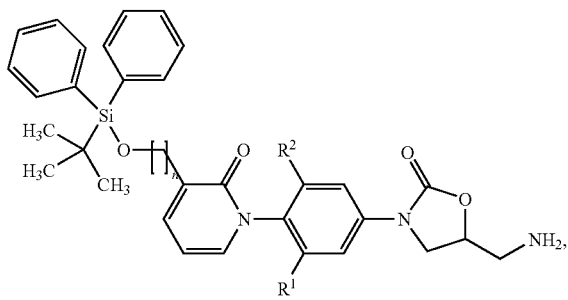

in which n, $R^1$ and $R^2$ have the meaning given above
with compounds of the formula (XVII)

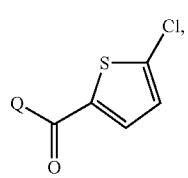

in which

Q represents halogen, preferably bromine or chlorine, or hydroxyl, followed by removal of the silyl group.

If Q is halogen, the reaction is generally carried out in inert solvents, if appropriate in the presence of a base, preferably in a temperature range of from −30° C. to 50° C. at atmospheric pressure.

Inert solvents are, for example, tetrahydrofuran, methylene chloride, pyridine, dioxane or dimethylformamide, preference is given to tetrahydrofuran or methylene chloride.

Bases are, for example, triethylamine, diisopropylethylamine or N-methylmorpholine; preference is given to diisopropylethylamine.

If Q is hydroxyl, the reaction is generally carried out in inert solvents, in the presence of a dehydrating agent, if appropriate in the presence of a base, preferably in a temperature range of from −30° C. to 50° C. at atmospheric pressure.

Inert solvents are, for example, halogenated hydrocarbons, such as dichloromethane or trichloromethane, hydrocarbons, such as benzene, nitromethane, dioxane, dimethylformamide or acetonitrile. It is also possible to use mixtures of the solvents. Particular preference is given to dichloromethane or dimethylformamide.

Here, suitable dehydrating agents are, for example, carbodiimides, such as, for example, N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethyl-polystyrene (PS-carbodiimide) or carbonyl compounds, such as carbonyldiimidazole, or 1,2-oxazolium compounds, such as 2-ethyl-5-phenyl-1,2-oxazolium 3-sulphate or 2-tert-butyl-5-methylisoxazolium perchlorate, or acylamino compounds, such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride or benzotriazolyloxy-tri(dimethylamino) phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)-phosphonium hexafluorophosphate (BOP), or N-hydroxysuccinimide, or mixtures of these, with bases.

Bases are, for example, alkali metal carbonates, such as, for example, sodium carbonate or potassium carbonate, or sodium bicarbonate or potassium bicarbonate, or organic bases, such as trialkylamines, for example triethylamine, N-methyl-morpholine, N-methylpiperidine, 4-dimethylaminopyridine or diisopropylethylamine.

The condensation with HATU or with EDC is preferably carried out in the presence of HOBt.

A silyl group is removed by methods known to the person skilled in the art, for example by reaction with tetrabutylammonium fluoride in a solvent, such as, for example, tetrahydrofuran, or by reaction with hydrogen chloride in methanol, preferably in a temperature range of from room temperature to reflux of the solvent at atmospheric pressure.

The compounds of the formula (XVII) are known or can be synthesized by known processes from the corresponding starting materials.

The compounds of the formula (II) in which X represents bromine are known or can be prepared by reacting the compounds of the formula (II) in which X represents hydroxyl with thionyl bromide, as described in Example 11A.

The compounds of the formula (VII) are known or can be prepared by reducing the nitro group in compounds of the formula (IX)

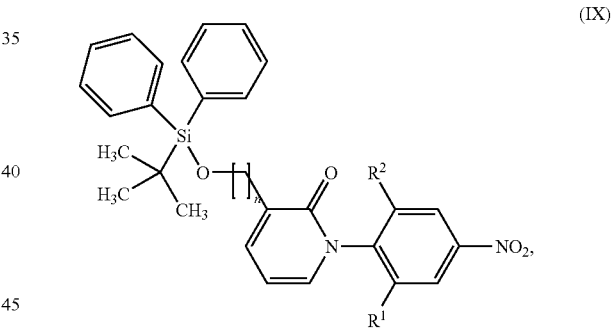

in which n, $R^1$ and $R^2$ have the meaning given above.

The reaction is generally carried out using a reducing agent in inert solvents, preferably in a temperature range of from room temperature to reflux of the solvents at from atmospheric pressure to 3 bar.

Reducing agents are, for example, palladium on carbon, hydrogen, tin dichloride, titanium trichloride or ammonium formate and palladium on carbon in a mixture of ethanol and ethyl acetate; preference is given to palladium on carbon and hydrogen or tin dichloride.

Inert solvents are, for example, ethers, such as diethyl ether, methyl tert-butyl ether, 1,2-dimethoxyethane, dioxane, tetrahydrofuran, glycol dimethyl ether or diethylene glycol dimethyl ether, alcohols, such as methanol, ethanol, n-propanol, isopropanol, n-butanol or tert-butanol, hydrocarbons, such as benzene, xylene, toluene, hexane, cyclohexan or mineral oil fractions, or other solvents, such as dimethylformamide, dimethylacetamide, acetonitrile or pyridine; preferred solvents are tetrahydrofuran, methanol, ethanol, isopropanol or, in the case of tin dichloride, dimethylformamide.

The compounds of the formula (IX) are known, can be synthesized by known processes from the corresponding starting materials or can be prepared analogously to the process described in the examples section.

The compounds of the formula (IV), in which Y represents chlorine are known or can be prepared by reacting compounds of the formula

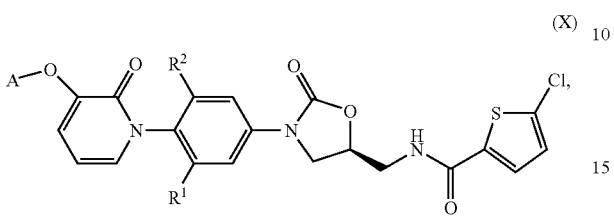
(X)

in which R$^1$ and R$^2$ have the meaning given above, and

A represents methyl or (2-methoxyethoxy)methyl, in a first step by removing the methoxy- or (2-methoxyethoxy)methoxy group, to give compounds of the formula

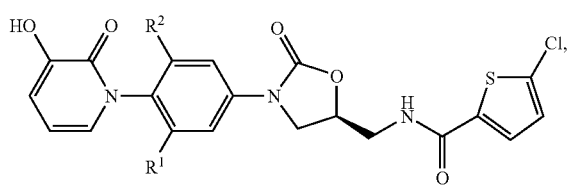
(XI)

in which R$^1$ and R$^2$ have the meaning given above, and, in the second step, with compounds of the formula

(XII)

in which m has the meaning given above, and

E represents bromine or iodine.

If A represents methyl, the reaction of the first step is generally carried out in inert solvents, in the present of bromine tribromide, preferably in a temperature range of from −78° C. to room temperature at atmospheric pressure.

Inert solvents are, for example, dichloromethane or 1,2-dichloroethane; preference is given to dichloromethane.

If A is (2-methoxyethoxy)methyl, the reaction of the first step is generally carried out in inert solvents, in the presence of trifluoroacetic acid, preferably in a temperature range of from room temperature to reflux of the solvent at atmospheric pressure.

Inert solvents are, for example, dichloromethane or 1,2-dichlorethane; preference is given to dichloromethane.

The reaction of the second step is generally carried out in inert solvents in the presence of a base, preferably in a temperature range of from room temperature to reflux of the solvent at atmospheric pressure. If appropriate, this reaction is carried out in a microwave oven.

Inert solvents are, for example, N,N-dimethylformamide or 1-methyl-2-pyrrolidine; preference is given to N,N-dimethylformamide.

Bases are, for example, alkali metal carbonates, such as caesium carbonate, sodium carbonate or potassium carbonate.

Compounds of the formula (XII) are known or can be synthesized by known processes from the corresponding starting materials.

The compounds of the formula (IV) in which Y represents hydroxyl are known or can be prepared by reacting, in the second step of the synthesis given above, the compounds of the formula (XI) with (2-bromoethoxy)(tert-butyl)dimethylsilane, followed by removal of the silyl group.

The compounds of the formula (X) are known or can be prepared by reacting the compounds of the formula (VI) in a first step with compounds of the formula

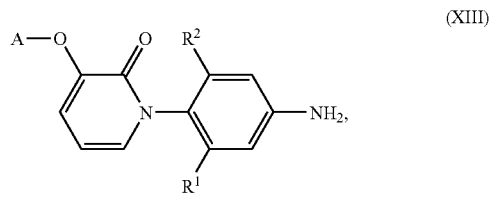
(XIII)

in which R$^1$ and R$^2$ have the meaning given above, and

A represents methyl or represents (2-methoxyethoxy)methyl, to give compounds of the formula

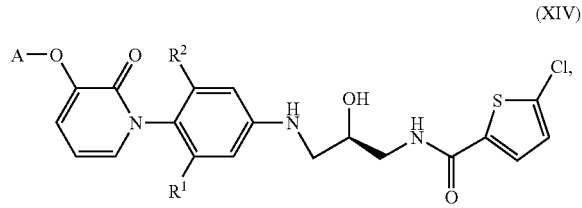
(XIV)

in which R$^1$ and R$^2$ have the meaning given above, and

A represents methyl or represents (2-methoxyethoxy)methyl, and, in the second step, cyclizing in the presence of phosgene or phosgene equivalents, such as, for example, carbonyldiimidazole (CU), to give the compounds of the formula (X).

The reaction of the first step is carried out according to the process described for the reaction of the compound of the formula (VI) with compounds of the formula (VII) to give compounds of the formula (VIII).

The reaction of the second step is carried out according to the process described for the reaction of compounds of the formula (VIII) to give compounds of the formula (II).

The compounds of the formula (XIII) are known or can be prepared by reducing the nitro group in compounds of the formula

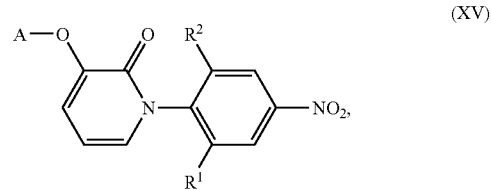
(XV)

in which R$^1$ and R$^2$ have the meaning given above, and

A represents methyl or represents (2-methoxyethoxy)methyl.

The reactions are carried out according to the process described for the reaction of compounds of the formula (IX) to give compounds of the formula (VII).

The compounds of the formula (XV) are known or can be synthesized by known processes from the corresponding starting materials.

The compounds of the formula (XVI) are known or can be prepared by removing the phthalimide protective group from compounds of the formula (XVIII)

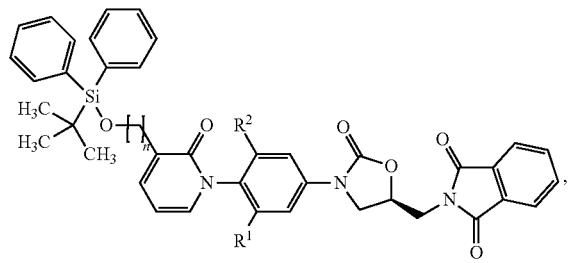

in which n, $R^1$ and $R^2$ have the meaning given above.

The reaction is generally carried out using an aqueous methylamine solution or a solution of hydrazine hydrate in ethanol, preferably using an aqueous methylamine solution at reflux of the solvents under atmospheric pressure.

The compounds of the formula (XVIII) are known or can be prepared by reacting, in a first step, compounds of the formula (VII) with a compound of the formula (XIX)

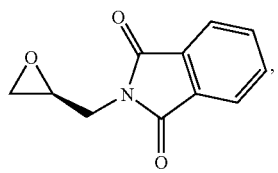

to give compounds of the formula (XX)

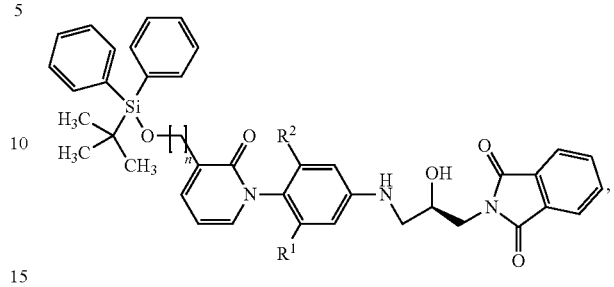

in which n, $R^1$ and $R^2$ have the meaning given above, and, in a second step, cyclizing in the presence of phosgene or phosgene equivalents, such as, for example, carbonyldiimidazole (CU), to give the compounds of the formula (XVIII).

The reaction of the first step is carried out according to the process described for the reaction of the compound of the formula (VI) with compounds of the formula (VII) to give compounds of the formula (VIII).

The reaction of the second step is carried out according to the process described for the reaction of compounds of the formula (VIII) to give compounds of the formula (II).

The compound of the formula (XIX) is known or can be synthesized by known processes from the corresponding starting materials.

The preparation of the compounds according to the invention can be illustrated by the synthesis schemes below:

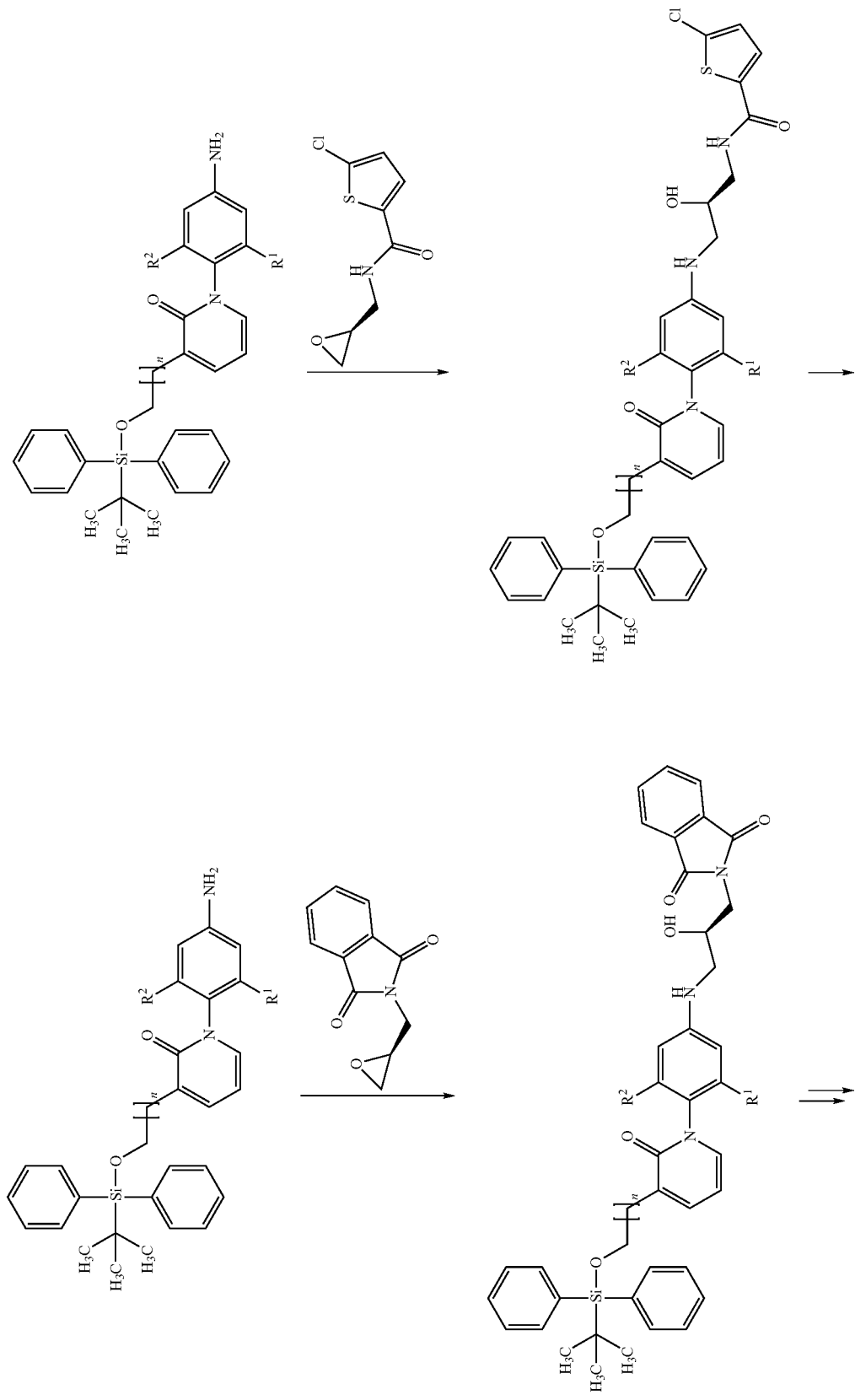
Scheme 1:

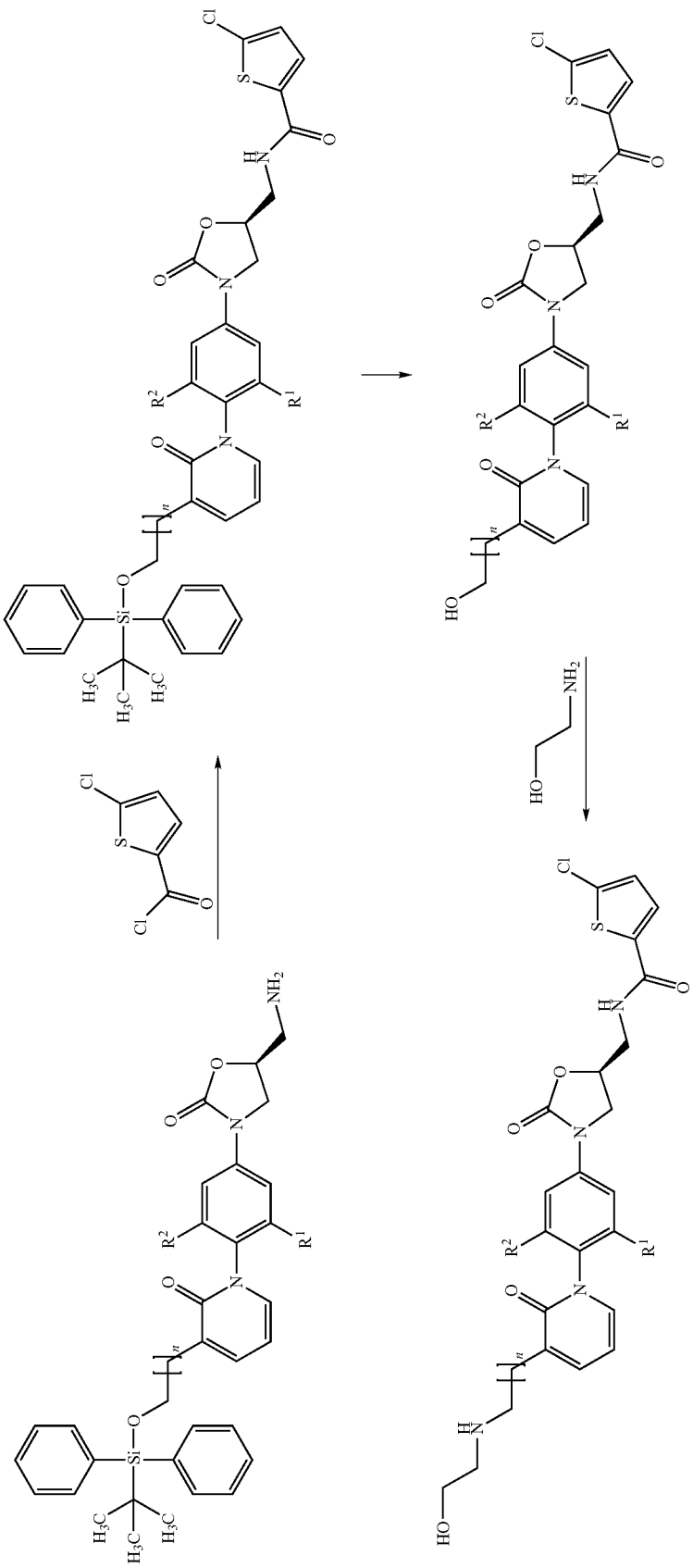

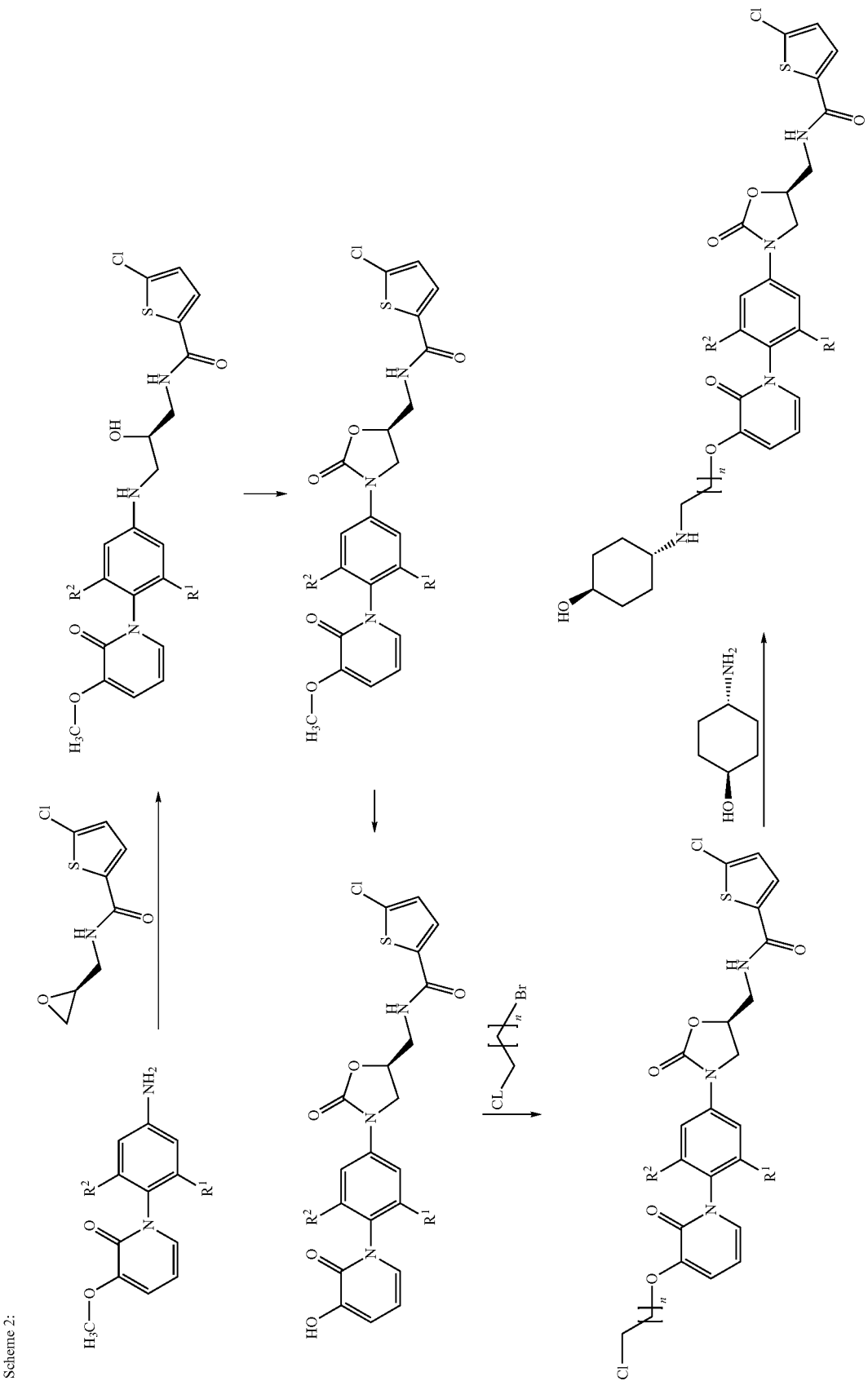
Scheme 2:

The compounds according to the invention have an unforeseeable useful spectrum of pharmacological activity.

Accordingly they are suitable for use as medicaments for the treatment and/or prophylaxis of diseases in humans and animals.

The compounds according to the invention are dual inhibitors of the blood coagulation factors Xa and thrombin (factor IIa) acting, in particular, as anticoagulants. The compounds inhibit both thrombin and factor Xa, prevent, by inhibiting thrombin production and activity on clots, their potential growth and have a wide therapeutic window.

In addition, the compounds according to the invention have favourable physicochemical properties such as, for example, good solubility in water and physiological media, which is advantageous for their therapeutic application.

The present invention furthermore provides the use of the compounds according to the invention for the treatment and/or prophylaxis of disorders, preferably thromboembolic disorders and/or thromboembolic complications.

"Thromboembolic disorders" in the sense of the present invention are in particular disorders such as myocardial infarction with ST segment elevation (STEMI) and without ST segment elevation (non-STEMI), stable angina pectoris, unstable angina pectoris, reocclusions and restenoses after coronary interventions such as angioplasty or aortocoronary bypass, peripheral arterial occlusion diseases, pulmonary embolisms, deep venous thromboses and kidney venous thromboses, transitory ischaemic attacks and also thrombotic and thromboembolic stroke.

Accordingly, the compounds according to the invention are also suitable for the prevention and treatment of cardiogenic thromboembolisms, such as, for example, cerebral ischaemias, stroke and systemic thromboembolisms and ischaemias, in patients having actue, intermittent or persistant cardial arrhythmias, such as, for example, atrial fibrillation, and those undergoing cardioversion, furthermore in patients having cardiac valve disorders or having artificial cardiac valves.

Thromboembolic complications are furthermore encountered in microangiopathic haemolytic anaemias, extracorporeal circulatory systems, such as haemodialysis, and prosthetic heart valves.

Moreover, the compounds according to the invention are also suitable for the prophylaxis and/or treatment of atherosclerotic vascular disorders and inflammatory disorders such as rheumatic disorders of the locomotor apparatus, and in addition also for the prophylaxis and/or treatment of Alzheimer's disease. Moreover, the compounds according to the invention can be used for inhibiting tumour growth and formation of metastases, for microangiopathies, age-related macula degeneration, diabetic retinopathy, diabetic nephropathy and other microvascular disorders, and also for the prevention and treatment of thromboembolic complications, such as, for example, venous thromboembolisms, for tumour patients, in particular those undergoing major surgical interventions or chemo- or radiotherapy.

Moreover, the compounds according to the invention are also suitable for the prophylaxis and/or treatment of pulmonary hypertension.

The term "pulmonary hypertension" includes certain forms of pulmonary hypertension, as determined, for example, by the World Health Organization (WHO) (*Clinical Classification of Pulmonary Hypertension*, Venice 2003). Examples which may be mentioned are pulmonary arterial hypertension, pulmonary hypertension associated with disorders of the left heart, pulmonary hypertension associated with pulmonary disorders and/or hypoxia and pulmonary hypertension owing to chronic thromboembolisms (CTEPH).

"Pulmonary arterial hypertension" comprises idiopathic pulmonary arterial hypertension (IPAH, formally also referred to as primary pulmonary hypertension), familiar pulmonary arterial hypertension (FPAH) and associated pulmonary-arterial hypertension (APAH), which is associated with collagenoses, congenital systemic-pulmonary shunt vitia, portal hypertension, HIV infections, the ingestion of certain drugs and medicaments, with other disorders (thyroid disorders, glycogen storage disorders, Morbus Gaucher, hereditary teleangiectasy, haemoglobinopathies, myeloproliferative disorders, splenectomy), with disorders having a significant venous/capillary contribution, such as pulmonary-venoocclusive disorder and pulmonary-capillary haemangiomatosis, and also persisting pulmonary hypertension of neonates.

Pulmonary hypertension associated with disorders of the left heart comprises a diseased left atrium or ventricle and mitral or aorta valve defects.

Pulmonary hyptertension associated with pulmonary disorders and/or hypoxia comprises chronic obstructive pulmonary disorders, interstitial pulmonary disorder, sleep apnoea syndrome, alveolar hypoventilation, chronic high-altitude sickness and inherent defects.

Pulmonary hypertension owing to chronic thromboembolisms (CTEPH) comprises the thromboembolic occlusion of proximal pulmonary arteries, the thromboembolic occlusion of distal pulmonary arteries and non-thrombotic pulmonary embolisms (tumour, parasites, foreign bodies).

The present invention furthermore provides the use of the compounds according to the invention for preparing medicaments for the treatment and/or prophylaxis of pulmonary hypertension associated with sarcoidosis, histiocytosis X and lymphangiomatosis.

Moreover, the substances according to the invention may also be suitable for treating pulmonary and hepatic fibroses.

Moreover, the compounds according to the invention may also be suitable for the treatment and/or prophylaxis of sepsis (or septicaemia), systemic inflammatory syndrome (SIRS), septic organ dysfunction, septic organ failure and multiorgan failure, acute respiratory distress syndrome (ARDS), acute lung injury (ALI), septic shock, DIC (disseminated intravascular coagulation or consumption coagulopathy) and/or septic organ failure.

"Sepsis" is defined as the presence of an infection and a systemic inflammatory response syndrome (hereinbelow referred to as "SIRS"). SIRS occurs associated with infections, but also other states such as injuries, burns, shock, operations, ischaemia, pancreatitis, reanimation or tumours. The definition of the ACCP/SCCM Consensus Conference Committee from 1992 (Crit Care Med 1992; 20:864-874) describes the diagnosis symptoms and measuring parameters required for the diagnosis "SIRS" (inter alia body temperature change, increased pulse, breathing difficulties and changed blood picture). The later (2001) SCCM/ESICM/ACCP/ATS/SIS International Sepsis Definitions Conference essentially kept the criteria, but fine-tuned details (Levy et al., Crit Care Med 2003; 31:1250-1256).

In the course of sepsis, there may be a generalized activation of the coagulation system (disseminated intravascular coagulation or consumption coagulopathy, hereinbelow referred to as "DIC") with microthromboses in various organs and secondary haemorrhagic complications. Moreover, there may be endothelial damage with increased permeability of the vessels and seeping of fluids and proteins into the extravasal lumen. As the sepsis progresses, there may be failure of an organ (for example kidney failure, liver failure, respiratory failure, central-nervous deficits and/or cardiovascular failure) or multiorgan failure. "Septic shock" refers to the onset of hypotension requiring treatment, which hypotension promotes further organ damage and is associated with a worsening of the prognosis.

Pathogens may be bacteria (Gram-negative and Gram-positive), fungi, viruses and/or eukaryotes. Entrance point or primary infection may be, for example, pneumonia, an infection of the urinary tract or peritonitis. Infection can be, but is not necessarily, associated with bacteremia.

DIC and/or SIRS may occur during sepsis, but also as a result of operations, tumour diseases, burns or other injuries. In DIC, there is a massive activation of the coagulatory system at the surface of damaged endothelial cells, the surfaces of foreign bodies or injured extravascular tissue. As a result, there is coagulation in small vessels of various organs with associated hypoxia and subsequent organ dysfunction. Secondary, there is a consumption of coagulation factors (for example factor X, prothrombin and fibrinogen) and platelets, which reduces the ability of the blood to coagulate and may result in serious bleeding.

Therapy of sepsis consists, firstly, of consequent elimination of the infectious cause, for example by operative focal reconstruction and antibiosis. Secondly, it consists in temporary intensive medical support of the affected organ systems. Therapies of various stages of this disease have been described, for example, in the following publication (Dellinger et al., Crit Care Med 2004; 32:858-873). For DIC, there are no proven effective therapies.

The invention furthermore provides medicaments comprising a compound according to the invention and one or more further active compounds, in particular for the treatment and/or prophylaxis of the disorders mentioned above. Exemplary and preferred active compound combinations are:

Antibiotic Therapy
  Various antibiotics or antifungal medicament combinations are suitable, either as calculated therapy (prior to the presence of the microbial diagnosis) or as specific therapy.
Fluid Therapy
  for example crystalloids or colloidal fluids.
Vasopressors
  for example norepinephrins, dopamines or vasopressin
Inotropic Therapy
  for example dobutamine
Corticosteroids
  for example hydrocortisone, or fludrocortisone
  Recombinant Human Activated Protein C
Xigris
Blood Products
  for example erythrocyte concentrates, platelet concentrates, erythropoietin or fresh frozen plasma
  Artificial ventilation in the case of sepsis-induced acute lung injury (ALI)
    or acute respiratory distress syndrome (ARDS)
    for example permissive hypercapnia, reduced tidal volumes
  Sedation, analgesia and neuromuscular blockade
  Sedation: for example diazepam, lorazepam, midazolam or propofol. Opioids: for example fentanyl, hydromorphone, morphine, meperidine or remifentanil. NSAIDs: for example ketorolac, ibuprofen or acetaminophen. Neuromuscular blockade: for example pancuronium
Glucose Control
  for example insulin, glucose
Renal Replacement Methods
  for example continuous veno-venous haemofiltration or intermittent haemodialysis. Low doses of dopamine for renal protection.
Anticoagulants
  for example for thrombosis prophylaxis or renal replacement methods, for example unfractionated heparins, low-molecular-weight heparins, heparinoids, hirudin, bivalirudin or argatroban.
Bicarbonate Therapy
Stress Ulcer Prophylaxis
  for example H2-receptor inhibitors, antacids In addition, the compounds according to the invention can also be used for preventing coagulation ex vivo, for example for preserving blood and plasma products, for cleaning/pretreatment of catheters and other medical aids and instruments, for coating synthetic surfaces of medical aids and instruments used in vivo or ex vivo or for biological samples comprising factor Xa and/or factor IIa.

The present invention furthermore provides the use of the compounds according to the invention for the treatment and/or prophylaxis of disorders, in particular the disorders mentioned above.

The present invention furthermore provides the use of the compounds according to the invention for preparing a medicament for the treatment and/or prophylaxis of disorders, in particular the disorders mentioned above.

The present invention furthermore provides a method for the treatment and/or prophylaxis of disorders, in particular the disorders mentioned above, using an anticoagulatory effective amount of the compound according to the invention.

The present invention furthermore provides a method for preventing the coagulation of blood in vitro, in particular in banked blood or biological samples containing factor Xa and/or factor IIa, which method is characterized in that an anticoagulatory effective amount of the compound according to the invention is added.

The present invention furthermore provides medicaments comprising a compound according to the invention and one or more further active compounds, in particular for the treatment and/or prophylaxis of the disorders mentioned above. By way of example and by way of preference, the following active compounds or combinations may be mentioned:

lipid-lowering substances, in particular HMG-CoA-(3-hydroxy-3-methylglutaryl-coenzyme A) reductase inhibitors, such as, for example, lovastatin (Mevacor; U.S. Pat. No. 4,231,938), simvastatin (Zocor; U.S. Pat. No. 4,444,784), pravastatin (Pravachol; U.S. Pat. No. 4,346,227), fluvastatin (Lescol; U.S. Pat. No. 5,354,772) and atorvastatin (Lipitor; U.S. Pat. No. 5,273,995);

coronary therapeutics/vasodilatators, in particular ACE (angiotensin converting enzyme) inhibitors, such as, for example, captopril, lisinopril, enalapril, ramipril, cilazapril, benazepril, fosinopril, quinapril and perindopril, or AII (angiotensin II) receptor antagonists, such as, for example, embusartan (U.S. Pat. No. 5,863,930), losartan, valsartan, irbesartan, candesartan, eprosartan and ternisartan, or β-adrenoceptor antagonists, such as, for example, carvedilol, alprenolol, bisoprolol, acebutolol, atenolol, betaxolol, carteolol, metoprolol, nadolol, penbutolol, pindolol, propanolol and timolol, or alpha-1-adrenoceptor antagonists, such as, for example, prazosine, bunazosine, doxazosine and terazosine, or diuretics, such as, for example, hydrochlorothiazide, furosemide, bumetanide, piretanide, torasemide, amiloride and dihydralazine, or calcium channel blockers, such as, for example, verapamil and diltiazem, or dihydropyridine derivatives, such as, for example, nifedipin (Adalat) and nitrendipine (Bayotensin), or nitro preparations, such as, for example, isosorbide 5-mononitrate, isosorbide dinitrate and glycerol trinitrate, or substances causing an increase in cyclic guanosine monophosphate (cGMP), such as, for example, stimulators of soluble guanylate cyclase (WO 98/16223, WO 98/16507, WO 98/23619, WO 00/06567, WO 00/06568, WO 00/06569, WO 00/21954, WO 00/66582, WO 01/17998, WO 01/19776, WO 01/19355, WO 01/19780, WO 01/19778, WO 07/045,366, WO 07/045,367, WO 07/045,369, WO 07/045,370, WO 07/045,433);

plasminogen activators (thrombolytics/fibrinolytics) and compounds which promote thrombolysis/fibrinolysis, such as inhibitors of the plasminogen activator inhibitor (PAI inhibitors) or inhibitors of the thrombin-activated fibrinolysis inhibitor (TAFI inhibitors) such as, for example, tissue plasminogen activator (t-PA), streptokinase, reteplase and urokinase;

anticoagulatory substances (anticoagulants), such as, for example, heparin (UFH), low-molecular-weight heparins (NMH), such as, for example, tinzaparin, certoparin, parnaparin, nadroparin, ardeparin, enoxaparin, reviparin, dalteparin, danaparoid, AVE 5026 (Sanofi-Aventis, *Company Presentation* 2008, Feb. 12), M118 (Momenta Pharmaceuticals Inc, *Press Release* 2008, Feb. 14), ORG42675 (Organon International Inc, *Company World Wide Website* 2007, April), and direct thrombin inhibitors (DTI), such as, for example, Exanta (ximelagatran)

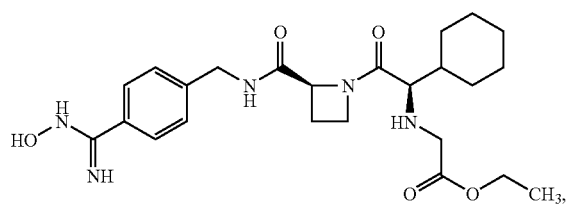

Rendix (dabigatran)

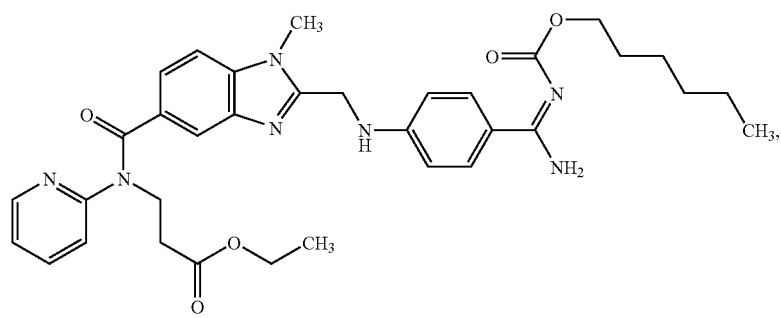

AZD-0837 [AstraZeneca Annual Report 2006, Mar. 19, 2007]

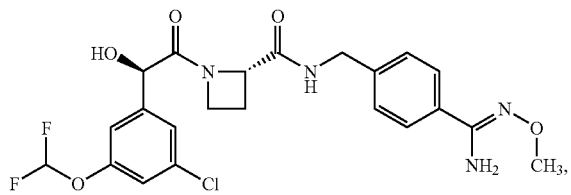

SSR-182289A [J. Lorrain et al. *Journal of Pharmacology and Experimental Therapeutics* 2003, 304, 567-574; J-M Altenburger et al. *Bioorg. Med. Chem.* 2004, 12, 1713-1730]

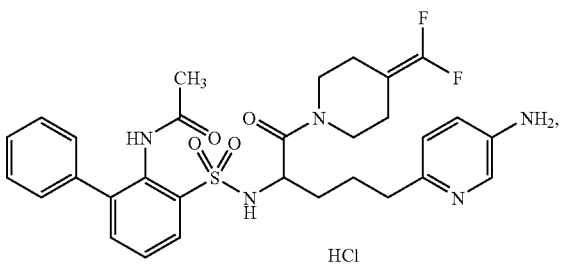

TGN-167 [S. Combe et al. *Blood* 2005, 106, abstract 1863 (ASH 2005)],

N-[(benzyloxy)carbonyl]-L-phenylalanyl-N-[(1S)-1-(dihydroxyboryl)-4-methoxybutyl]-D-prolinamide [WO 2005/084685]

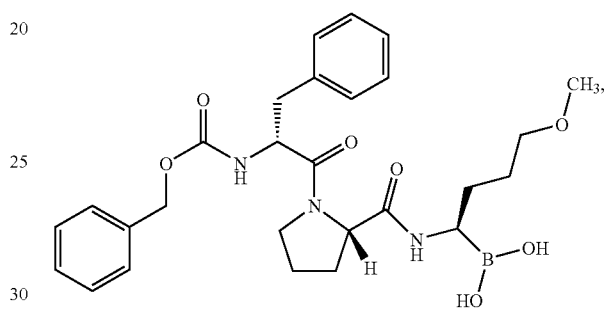

Sofigatran [*WHO Drug Information* 2007, 21, 77]

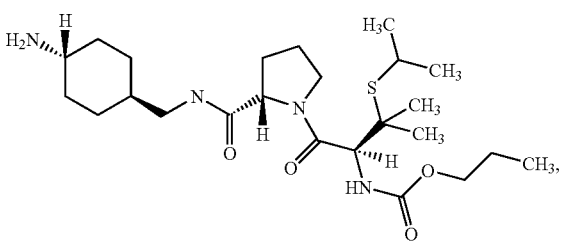

MCC-977 [Mitsubishi Pharma website pipeline 2006, Jul. 25, 2006],

MPC-0920 [Press Release: Myriad Genetics Begins Phase 1 Trial of Anti-Thrombin Drug MPC-0920", Myriad Genetics Inc, 02. Mai 2006] and TGN-255 (flovagatran)

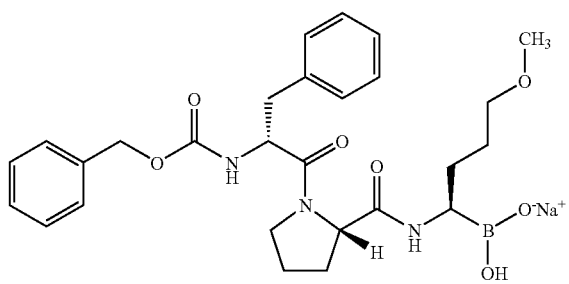

and direct factor Xa inhibitors, such as, for example,
rivaroxaban (BAY 59-7939): 5-chloro-N-({(5S)-2-oxo-3-[4-(3-oxomorpholin-4-yl)phenyl]-1,3-oxazolidin-5-yl}methyl)thiophene-2-carboxamide [WO 2001/47919]

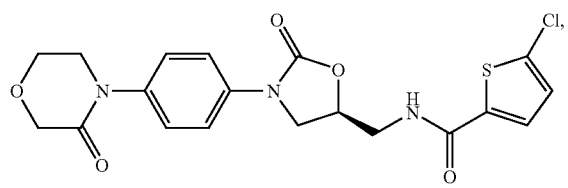

AX-1826 [S. Takehana et al. *Japanese Journal of Pharmacology* 2000, 82 (Suppl. 1), 213P; T. Kayahara et al. *Japanese Journal of Pharmacology* 2000, 82 (Suppl. 1), 213P],
tanogitran (BIBT-986, prodrug: BIBT-1011): N-[(1R)-1-{2-[({4-[amino(imino)methyl]-phenyl}amino)methyl]-1-methyl-1H-benzimidazol-5-yl}-1-methyl-2-oxo-2-pyrrolidin-1-ylethyl]glycine [American Chemical Society—226th National Meeting, New York City, N.Y., USA, 2003]

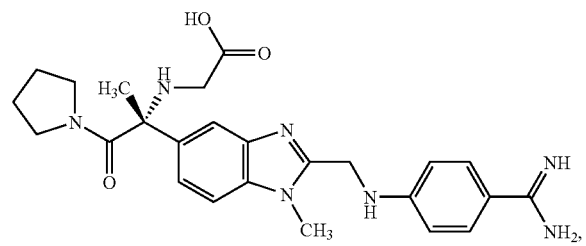

compounds disclosed in WO 2004/056784,
YM-150 [Y. Iwatsuki et al. *Blood* 2006, 108, abstract 911 (ASH 2006)],
N-{4-bromo-2-[(5-chloropyridin-2-yl)carbamoyl]-6-hydroxyphenyl}-1-isopropylpiperidine-4-carboxamide [JP 2005/179272]

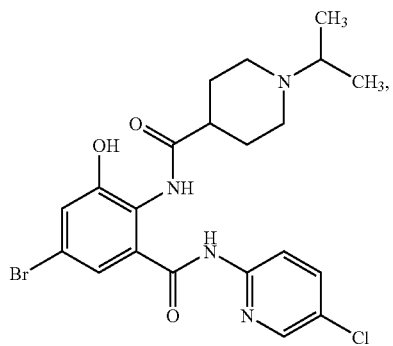

compounds disclosed in WO 2000/242270,

AZ 12300547: 6-[4-({(2S)-4-[(3-chloro-1H-indol-6-yl)sulphonyl]-2-methyl-6-oxopiperazin-1-yl}methyl)phenyl]-2-methylpyridazin-3(2H)-one [K. L Granberg et al. American Chemical Society—232th National Meeting, San Francisco, USA, 2006, MEDI 391]

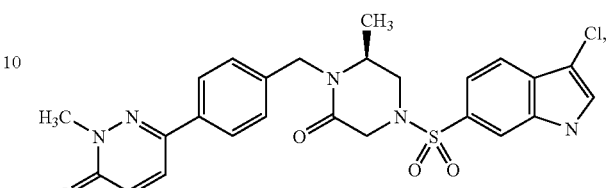

compounds disclosed in WO 2007/008142,
razaxaban (DPC-906): 1-(3-amino-1,2-benzisoxazol-5-yl)-N-(4-{2-[(dimethylamino)-methyl]-1H-imidazol-1-yl}-2-fluorophenyl)-3-(trifluoromethyl)-1H-pyrazole-5-carboxamide [*J. Med. Chem.* 2005, 48, 1729-1744]

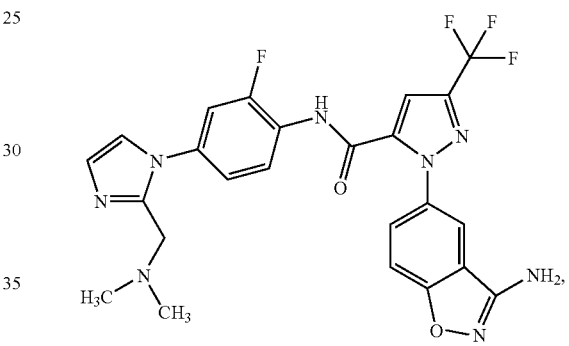

apixaban (BMS-562247): 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide [WO 2003/026652, WO 2003/049681]

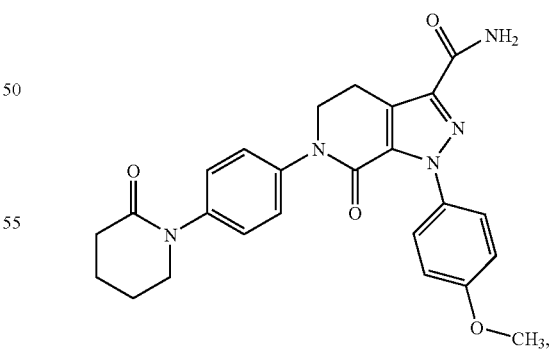

BMS-691648: 3-chloro-N-[(3S,4R)-1-(methylsulphonyl)-4-{[4-(2-oxopyridin-1(2H)-yl)benzoyl]amino}piperidin-3-yl]-1H-indole-6-carboxamide [T. Güngör et al. *Drugs Fut.* 2006, 31(Suppl A): abstract P118; WO 2004/082687]

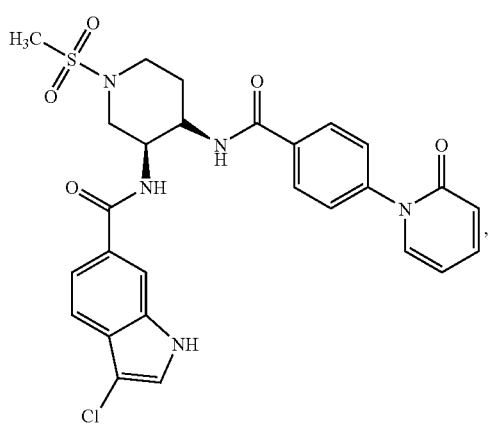

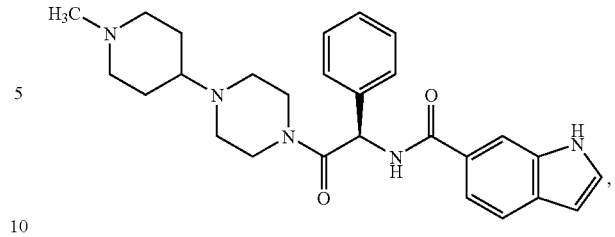

DX-9065a: (2S)-3-{7-[amino(imino)methyl]-2-naphthyl}-2-(4-{[(3S)-1-ethanimidoyl-pyrrolidin-3-yl]oxy}phenyl)propanoic acid [T. Nagahara et al. *J. Med. Chem.* 1994, 37, 1200-1207]

813893 [Proteinase Inhibitor Design—Fourth SCI-RSC Symposium, Proteinase 2004: Strategies for New Medicines (Part I), London], 6-chloro-N-{(3S)-1-[(1S)-1-methyl-2-morpholin-4-yl-2-oxoethyl]-2-oxopyrrolidin-3-yl}naphthalene-2-sulphonamide [N. S. Watson et al. *Bioorg. Med. Chem. Lett.* 2006, 16, 3784; WO 2002/100830; WO 2002/100886]

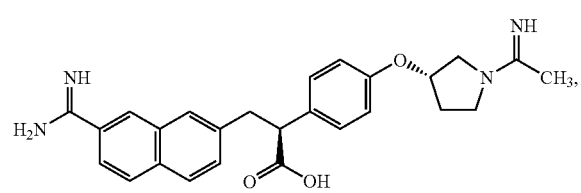

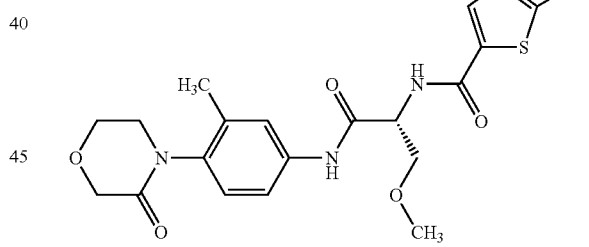

DU-176b [Y. Morishima et al. *Blood* 2004, 104, abstract 1862 (ASH 2004); T. Fukuda et al. *Blood* 2004, 104, abstract 1852 (ASH 2004); T. Furugohri et al. *Blood* 2004, 104, abstract 1851 (ASH 2004)], N-(5-chloropyridin-2-yl)-N'-[(1S,2R,4S)-4-(dimethylcarbamoyl)-2-{[(5-methyl-4,5,6,7-tetrahydro[1,3]thiazolo[5,4-c]pyridin-2-yl)carbonyl]amino}cyclohexyl]ethanediamide [US 2005/0020645, WO 2005/47296]

KFA-1982 (prodrug of KFA-1829) [T. Koizumi et al. *Journal of Thrombosis and Hemostasis* 2003, 1 Suppl 1, P2022], EMD-503982 [Merck KGaA Annual Report 2006, 48-49], EMD-495235: 5-chloro-N-[(1R)-1-(methoxymethyl)-2-{[3-methyl-4-(3-oxomorpholin-4-yl)-phenyl]amino}-2-oxoethyl]thiophene-2-carboxamide [*Bioorg. Med. Chem. Lett.* 2004, 14, 5817-5822]

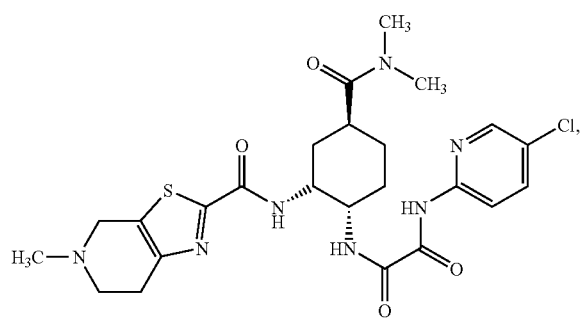

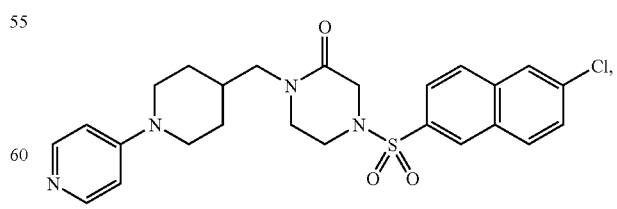

M-55113: 4-[(6-chloro-2-naphthyl)sulphonyl]-1-[(1-pyridin-4-ylpiperidin-4-yl)methyl]piperazin-2-one [H. Nishida et al. *Chem. Pharm. Bull.* 2001, 49, 1237-1244]

compounds disclosed in US 2005/0020645,

LY517717: N-{(1R)-2-[4-(1-methylpiperidin-4-yl)piperazin-1-yl]-2-oxo-1-phenylethyl}-1H-indole-6-carboxamide [WO 2000/76971, WO 2002/100847]

M-55551/M-55555: (2R)-4-[(6-chloro-2-naphthyl)sulphonyl]-6-oxo-1-[(1-pyridin-4-ylpiperidin-4-yl)methyl]piperazine-2-carboxylic acid [H. Nishida et al. *Chem. Pharm. Bull.* 2002, 50, 1187-1194]

compounds disclosed in WO 2006/002099, otamixaban (FXV-673, RPR-130673): methyl (2R,3R)-2-{3-[amino(imino)methyl]benzyl}-3-{[4-(1-oxidopyridin-4-yl)benzoyl]amino}butanoate [V. Chu et al. *Thrombosis Research* 2001, 103, 309-324; K. R. Guertin et al. *Bioorg Med. Chem. Lett.* 2002, 12, 1671-1674]

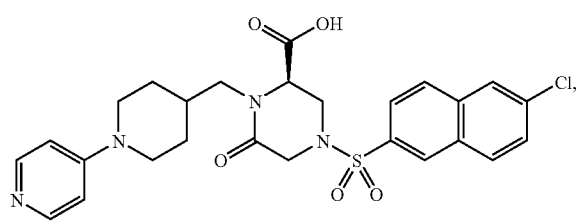

M-55190: ethyl (2R)-4-[(6-chloro-2-naphthyl)sulphonyl]-6-oxo-1-[(1-pyridin-4-ylpiperidin-4-yl)methyl]piperazine-2-carboxylate [H. Nishida et al. 16th Int Symp Med Chem, Bologna, 18-22 Sep. 2000, Abst PA-125]

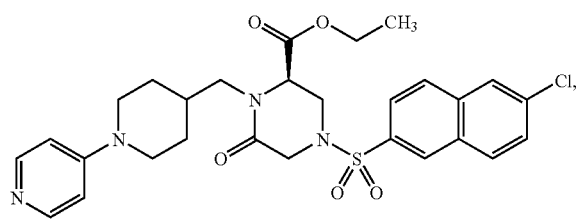

M-55532: 7-[(6-chloro-2-naphthyl)sulphonyl]-8a-(methoxymethyl)-1'-pyridin-4-yltetrahydro-5H-spiro[1,3-oxazolo[3,2-a]pyrazine-2,4'-piperidin]-5-one [H. Nishida et al. 228th ACS National Meeting, Philadelphia, Aug. 22-26, 2004, MEDI-251; H. Nishida et al. *Chem. Pharm. Bull.* 2004, 52, 406-412; dito 459-462]

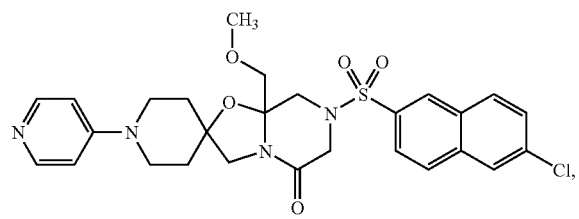

N-({7-[(5-chloro-1H-indol-2-yl)sulphonyl]-5-oxo-1'-propionyltetrahydro-8aH-spiro[1,3-oxazolo-[3,2-a]pyrazine-2,4'-piperidin]-8a-yl}methyl)-N-methylglycine [WO 2006/106804]

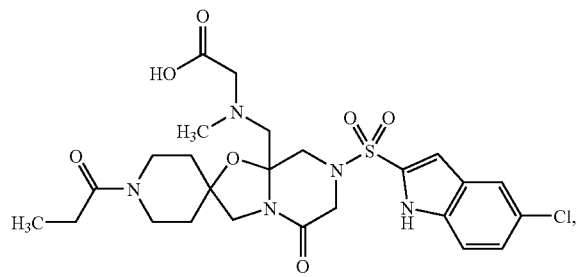

PRT54021 [U. Sinha et al. *Blood* 2006, 108, abstract 907 (ASH 2006); K. Abe et al. *Blood* 2006, 108, abstract 901 (ASH 2006)],

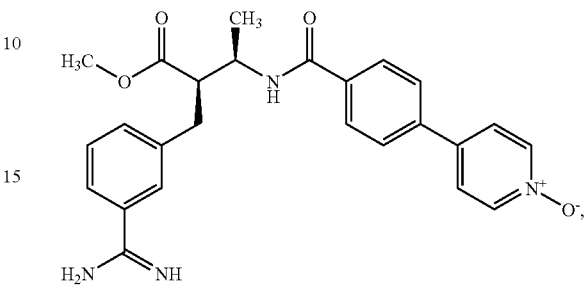

AVE3247 [Sanofi Aventis Company Presentation, Paris 2007, Feb. 13],

SAR377142 (SSR-7142) [Sanofi Aventis Company Presentation, Paris 2007, Feb. 13], HMR-2906 [XVIIth Congress of the International Society for Thrombosis and Haemostasis, Washington D.C., USA, 14-21 Aug. 1999; Generating greater value from our products and pipeline. Aventis SA Company Presentation, 5 Feb. 2004], idraparinux [Harry R. Büller et al. *Blood,* 2006, 108, abstract 571 (ASH 2006)] and fondaparinux;

substances which inhibit the aggregation of platelets (platelet aggregation inhibitors, thrombocyte aggregation inhibitors), such as, for example, acetylsalicylic acid (such as, for example, aspirin), ticlopidine (ticlid), clopidogrel (plavix) and prasugrel;

fibrinogen receptor antagonists (glycoprotein-IIb/IIIa antagonists), such as, for example, abciximab, eptifibatide, tirofiban, lamifiban, lefradafiban and fradafiban;

and also antiarrhythmics.

The present invention further relates to medicaments which comprise at least one compound according to the invention, normally together with one or more inert, non-toxic, pharmaceutically suitable excipients, and to the use thereof for the aforementioned purposes.

The compounds according to the invention can act systemically and/or locally. For this purpose, they can be administered in a suitable way such as, for example, by the oral, parenteral, pulmonal, nasal, sublingual, lingual, buccal, rectal, dermal, transdermal, conjunctival, otic route or as implant or stent.

The compounds according to the invention can be administered in administration forms suitable for these administration routes.

Suitable for oral administration are administration forms which function according to the prior art and deliver the compounds according to the invention rapidly and/or in modified fashion, and which contain the compounds according to the invention in crystalline and/or amorphized and/or dissolved form, such as, for example, tablets (uncoated or coated tablets, for example having enteric coatings or coatings which are insoluble or dissolve with a delay and control the release of the compound according to the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilizates or sterile powders.

Suitable for the other administration routes are, for example, pharmaceutical forms for inhalation (inter alia powder inhalers, nebulizers), nasal drops, solutions or sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (e.g. patches), milk, pastes, foams, dusting powders, implants or stents.

Oral or parenteral administration is preferred, especially oral administration.

The compounds according to the invention can be converted into the stated administration forms. This can take place in a manner known per se by mixing with inert, non-toxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (e.g. antioxidants such as, for example, ascorbic acid), colours (e.g. inorganic pigments such as, for example, iron oxides) and masking flavours and/or odours.

It has generally proved advantageous to administer on parenteral administration amounts of about 0.001 to 5 mg/kg, preferably about 0.01 to 1 mg/kg, of body weight to achieve effective results, and on oral administration the dosage is about 0.01 to 100 mg/kg, preferably about 0.01 to 20 mg/kg, and very particularly preferably 0.1 to 10 mg/kg, of body weight.

It may nevertheless be necessary where appropriate to deviate from the stated amounts, in particular as a function of the body weight, route of administration, individual response to the active ingredient, nature of the preparation and time or interval over which administration takes place. Thus, it may be sufficient in some cases to make do with less than the aforementioned minimum amount, whereas in other cases the stated upper limit must be exceeded. It may in the event of administration of larger amounts be advisable to divide these into a plurality of individual doses over the day.

The following exemplary embodiments illustrate the invention. The invention is not restricted to the examples.

The percentage data in the following tests and examples are, unless indicated otherwise, percentages by weight; parts are parts by weight. Solvent ratios, dilution ratios and concentration data for the liquid/liquid solutions are in each case based on volume.

A. EXAMPLES

Abbreviations
  CDI carbonyldiimidazole
  d doublet (in NMR)
  TLC thin-layer chromatography
  DCI direct chemical ionization (in MS)
  dd doublet of doublets (in NMR)
  DMAP 4-dimethylaminopyridine
  DMF N,N-dimethylformamide
  DMSO dimethyl sulphoxide
  d day(s)
  eq. equivalent(s)
  ESI electrospray ionization (in MS)
  h hour(s)
  HPLC high pressure, high performance liquid chromatography
  LC-MS liquid chromatography-coupled mass spectroscopy
  m multiplet (in NMR)
  min minute(s)
  MS mass spectroscopy
  NMR nuclear magnetic resonance spectroscopy
  RP reversed phase (in HPLC)
  RT room temperature
  $R_t$ retention time (in HPLC)
  singulet (in NMR)
  THF tetrahydrofuran LC-MS and HPLC Methods Method 1 (HPLC): Instrument: HP 1100 with DAD detection; column: Kromasil 100 RP-18, 60 mm×2.1 mm, 3.5 µm; mobile phase A: 5 ml perchloric acid (70% strength)/L of water, mobile phase B: acetonitrile; gradient: 0 min 2% B, 0.5 min 2% B, 4.5 min 90% B, 6.5 min 90% B, 6.7 min 2% B, 7.5 min 2% B; flow rate: 0.75 ml/min; column temperature: 30° C.; detection: UV 210 nm.

Method 2 (HPLC): Instrument: HP 1100 with DAD detection; column: Kromasil 100 RP-18, 60 mm×2.1 mm, 3.5 µm; mobile phase A: 5 ml perchloric acid (70% strength)/1 of water, mobile phase B: acetonitrile; gradient: 0 min 2% B, 0.5 min 2% B, 4.5 min 90% B, 9 min 90% B, 9.2 min 2% B, 10 min 2% B; flow rate: 0.75 ml/min; column temperature: 30° C.; detection: UV 210 nm.

Method 3 (LC-MS): MS instrument type: Micromass ZQ; HPLC instrument type: Waters Alliance 2795; column: Phenomenex Synergi 2µ Hydro-RP Mercury 20 mm×4 mm; mobile phase A: 1 l of water+0.5 ml 50% strength of formic acid, mobile phase B: 1 l of acetonitrile+0.5 ml 50% strength of formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 4 (LC-MS): MS instrument type: Micromass ZQ; HPLC instrument type: HP 1100 Series; UV DAD; column: Phenomenex Synergi 2µ Hydro-RP Mercury 20 mm×4 mm; mobile phase A: 1 l of water+0.5 ml 50% strength of formic acid, mobile phase B: 1 l of acetonitrile+0.5 ml 50% strength of formic acid; gradient: 0.0 min 90% A→2.5 min 30% A→3.0 min 5% A→4.5 min 5% A; flow rate: 0.0 min 1 ml/min, 2.5 min/3.0 min/4.5 min. 2 ml/min; oven: 50° C.; UV detection: 210 nm.

Method 5 (LC-MS): Instrument: Micromass Quattro LCZ with HPLC Agilent Serie 1100; column: Phenomenex Synergi 2µ Hydro-RP Mercury 20 mm×4 mm; mobile phase A: 1 l of water+0.5 ml 50% strength of formic acid, mobile phase B: 1 l of acetonitrile+0.5 ml 50% strength of formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 208-400 nm.

Method 6 (LC-MS): MS instrument type: Micromass ZQ; HPLC instrument type: HP 1100 Series; UV DAD; column: Phenomenex Gemini 3µ 30 mm×3.00 mm; mobile phase A: 1 l of water+0.5 ml 50% strength of formic acid, mobile phase B: 1 l of acetonitrile+0.5 ml 50% strength of formic acid;

gradient: 0.0 min 90% A→2.5 min 30% A→3.0 min 5% A→4.5 min 5% A; flow rate: 0.0 min 1 ml/min, 2.5 min/3.0 min/4.5 min. 2 ml/min; oven: 50° C.; UV detection: 210 nm.

Method 7 (LC-MS): Instrument: Micromass Platform LCZ with HPLC Agilent Serie 1100; column: Thermo Hypersil GOLD 3μ 20 mm×4 mm; mobile phase A: 1 l of water+0.5 ml 50% strength of formic acid, mobile phase B: 1 l of acetonitrile+0.5 ml 50% strength of formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 8 (LC-MS): MS instrument type: Waters ZQ; HPLC instrument type: Waters Alliance 2795; column: Phenomenex Onyx Monolithic C18, 100 mm×3 mm; mobile phase A: 1 l of water+0.5 ml 50% strength of formic acid, mobile phase B: 1 l of acetonitrile+0.5 ml 50% strength of formic acid; gradient: 0.0 min 90% A→2 min 65% A→4.5 min 5% A→6 min 5% A; flow rate: 2 ml/min; oven: 40° C.; UV detection: 210 nm.

Method 9 (GC-MS): Instrument: Micromass GCT, GC6890; column: Restek RTX-35MS, 30 m×250 μm×0.25 μm; constant helium flow: 0.88 ml/min; oven: 60° C.; inlet: 250° C.; gradient: 60° C. (maintained for 0.30 min), 50° C./min→120° C., 16° C./min→250° C., 30° C./min→300° C. (maintained for 1.7 min).

Method 10 (GC-MS): Instrument: Micromass GCT, GC6890; column: Restek RTX-35, 15 m×200 μm×0.33 μm; constant helium flow: 0.88 ml/min; oven: 70° C.; inlet: 250° C.; gradient: 70° C., 30° C./min→310° C. (maintained for 3 min).

Method 11 (LC-MS): Instrument: Micromass Quattro LCZ with HPLC Agilent Serie 1100; column: Phenomenex Onyx Monolithic C18, 100 mm×3 mm. mobile phase A: 1 l of water+0.5 ml 50% strength of formic acid, mobile phase B: 1 l of acetonitrile+0.5 ml 50% strength of formic acid; gradient: 0.0 min 90% A→2 min 65% A→4.5 min 5% A→6 min 5% A; flow rate: 2 ml/min; oven: 40° C.; UV detection: 208-400 nm.

Method 12 (LC-MS): Instrument: Micromass Quattro LCZ with HPLC Agilent Serie 1100; column: Phenomenex Synergi 2.5μ MAX-RP 100A Mercury 20 mm×4 mm; mobile phase A: 1 l of water+0.5 ml 50% strength of formic acid, mobile phase B: 1 l of acetonitrile+0.5 ml 50% strength of formic acid; gradient: 0.0 min 90% A→0.1 min 90% A→3.0 min 5% A→4.0 min 5% A→4.1 min 90% A; flow rate: 2 ml/min; oven: 50° C.; UV detection: 208-400 nm.

Method 13 (LC-MS): MS instrument type: Micromass ZQ; HPLC instrument type: Waters Alliance 2795; column: Phenomenex Synergi 2.5μ MAX-RP 100A Mercury 20 mm×4 mm; mobile phase A: 1 l of water+0.5 ml 50% strength of formic acid, mobile phase B: 1 l of acetonitrile+0.5 ml 50% strength of formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.

Method 14 (LC-MS): Instrument: Micromass Quattro Premier with Waters HPLC Acquity; column: Thermo Hypersil GOLD 1.9μ 50 mm×1 mm; mobile phase A: 1 l of water+0.5 ml 50% strength of formic acid, mobile phase B: 1 l of acetonitrile+0.5 ml 50% strength of formic acid; gradient: 0.0 min 90% A→0.1 min 90% A→1.5 min 10% A→2.2 min 10% A; flow rate: 0.33 ml/min; oven: 50° C.; UV detection: 210 nm.

Starting Materials

Example 1A

5-Chloro-N-[(2S)-oxiran-2-ylmethyl]thiophene-2-carboxamide

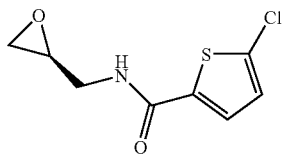 [SMILES: O=C(NC[C@H]1CO1)c1ccc(Cl)s1]

Example 1A is prepared as described in WO04/101557 (Example 6A).

Example 2A 3-(Hydroxymethyl)pyridin-2(1H)-one

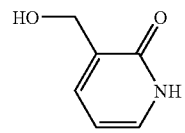

At RT, 23.2 g (144 mmol) of hexamethyldisilane and 0.781 g (7.19 mmol) of chlorotrimethylsilane are added to a suspension of 10.0 g (71.9 mmol) of 2-hydroxynicotinic acid in 100 ml of toluene, and the mixture is stirred with a KPG stirrer at 110° C. for 30 min. The mixture is then cooled to −40° C., and 22.5 g (158 mmol) of a 1 molar solution of diisobutylaluminium hydride in dichloromethane are added dropwise to the solution. The mixture is thawed to RT, stirred at RT for 18 h and finally, at −10° C., adjusted to pH=4 with dilute hydrochloric acid, and 500 ml of methanol are added such that the temperature does not exceed −10° C. The precipitate formed is filtered off, 100 ml of water are added to the filtrate, the mixture is stirred at 50° C. for 1 h and the precipitate is filtered off. Concentration of the filtrate gives 8.55 g (95% of theory) of the desired compound.

$^1$H-NMR (400 MHz, DMSO-d$_6$, δ/ppm): 11.53 (br. s, 1H), 7.40 (d, 1H), 7.25 (d, 1H), 6.19 (dd, 1H), 5.00 (t, 1H), 4.28 (d, 2H).

HPLC (method 1): R$_t$=0.27 min.

MS (ESIpos, m/z): 148 (M+Na)$^+$.

Example 3A 3-({[tert-Butyl(diphenyl)silyl]oxy}methyl)pyridin-2(1H)-one

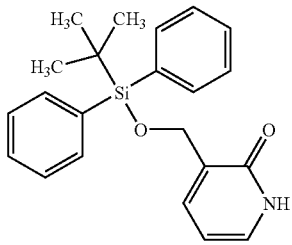 [SMILES: CC(C)(C)[Si](OCc1ccc[nH]c1=O)(c1ccccc1)c1ccccc1]

At RT, 0.65 g (9.59 mmol) of imidazole, 2.42 g (8.79 mmol) of t-butyldiphenylchlorosilane and 0.10 g (0.80 mmol) of DMAP are added to 1.00 g (7.99 mmol) of the compound from Example 2A in 19 ml of DMF, and the mixture is stirred for 18 h. 180 ml of water are then added, and the mixture is kept at 0° C. for 3 h. After filtration, the residue obtained is purified by chromatography on silica gel (ethyl acetate/ethyldimethylamine 1000:1). This gives 801 mg (27% of theory) of the desired compound.

$^{1}$H-NMR (400 MHz, DMSO-$d_6$, δ/ppm): 11.61 (br. s, 1H), 7.69-7.52 (m, 5H), 7.51-7.38 (m, 6H), 7.30 (d, 1H), 6.29 (dd, 1H), 4.51 (s, 2H), 1.05 (s, 9H).

HPLC (method 2): $R_f$=5.27 min.

MS (DCI, m/z): 364 (M+H)$^{+}$.

Example 4A 3-({[tert-Butyl(diphenyl)silyl]oxy}methyl)-1-(2-chloro-4-nitrophenyl)pyridin-2(1H)-one

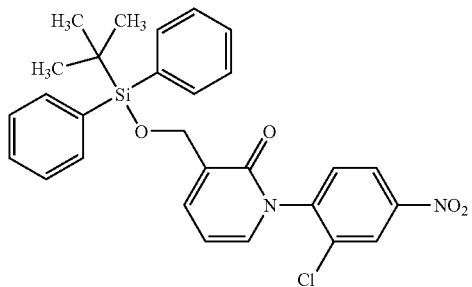 [SMILES: CC(C)(C)[Si](OCc1cccn(-c2ccc([N+](=O)[O-])cc2Cl)c1=O)(c1ccccc1)c1ccccc1]

At 0° C., 0.500 g (4.46 mmol) of potassium tert-butoxide is added to 1.08 g (2.97 mmol) of the compound from Example 3A in 21 ml of DMF, and the mixture is stirred at room temperature for 30 min. 0.571 g (3.27 mmol) of 2-chloro-1-fluoro-4-nitrobenzene is added, and the mixture is stirred at RT. After 4.5 h, 200 ml of water are added, and the mixture is then extracted three times with ethyl acetate. The combined organic phases are washed with water and then dried over sodium sulphate. After filtration, the solvents are removed under reduced pressure. The residue is purified by chromatography on silica gel (cyclohexane/ethyl acetate 9:1). This gives 872 mg (56% of theory) of the desired compound.

$^{1}$H-NMR (400 MHz, DMSO-$d_6$, δ/ppm): 8.52 (d, 1H), 8.32 (dd, 1H), 7.85 (d, 1H), 7.76 (dd, 1H), 7.68-7.63 (m, 4H), 7.59-7.55 (m, 1H), 7.54-7.41 (m, 6H), 6.54 (dd, 1H), 4.56 (br. s, 2H), 1.07 (s, 9H).

HPLC (method 2): $R_f$=6.05 min.

MS (DCI, m/z): 519 (M+H)$^{+}$.

Example 5A 1-(4-Amino-2-chlorophenyl)-3-({[tert-butyl(diphenyl)silyl]oxy}methyl)pyridin-2(1H)-one

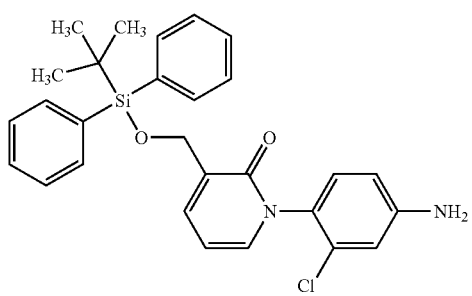

800 mg (1.54 mmol) of the compound from Example 4A are dissolved in 48 ml of THF. 50 mg (0.05 mmol) of palladium on carbon are then added, and the mixture is hydrogenated at RT in a hydrogen atmosphere under atmospheric pressure. The mixture is then filtered, the filter cake is washed with THF and the filtrate is freed from the solvent. The reaction product (purity: 95%) is reacted further without further purification.

HPLC (method 1): $R_f$=5.55 min.

MS (ESIpos, m/z): 489 (M+H)$^{+}$.

Example 6A

N-{[(5S)-3-{4-[3-({[tert-Butyl(diphenyl)silyl]oxy}methyl)-2-oxopyridin-1(2H)-yl]-3-chloro-phenyl}-2-oxo-1,3-oxazolidin-5-yl]methyl}-5-chlorothiophene-2-carboxamide

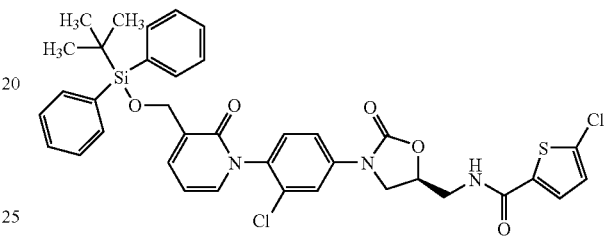

386 mg (1.77 mmol) of the compound from Example 1A are added to a solution of 789 mg (1.61 mmol) of the compound from Example 5A in 24 ml of acetonitrile. 540 mg (2.42 mmol) of magnesium perchlorate are added to the suspension. After 19 h at RT, 193 mg (0.952 mmol) of the compound from Example 1A are added, and stirring at RT is continued for a further 30 h. 523 mg (2.46 mmol) of 1,1'-carbonyldiimidazole and 19 mg (0.09 mmol) of DMAP are then added, and the mixture is heated at 60° C. After 21 h, the mixture is diluted with water, saturated aqueous sodium chloride solution and ethyl acetate. The aqueous phase is extracted twice with ethyl acetate, and the combined organic phases are dried over sodium sulphate. After filtration, the solvent is removed and the residue is purified by chromatography on silica gel (cyclohexane/ethyl acetate 1:1). This gives 533 mg (45% of theory) of the desired product.

$^{1}$H-NMR (400 MHz, DMSO-$d_6$, δ/ppm): 8.97 (t, 1H), 7.85 (dd, 1H), 7.73 (dd, 1H), 7.70-7.63 (m, 5H), 7.58 (dd, 1H), 7.53-7.38 (m, 8H), 7.19 (d, 1H), 6.47 (dd, 1H), 4.91-4.82 (m, 1H), 4.55 (br. s, 2H), 4.24 (dd, 1H), 3.89 (dd, 1H), 3.65-3.58 (m, 2H), 1.07 (s, 9H).

HPLC (method 2): $R_f$=6.07 min.

MS (ESIpos, m/z): 732 (M+H)$^{+}$.

Example 7A 3-({[tert-Butyl(diphenyl)silyl]oxy}methyl)-1-(2-methyl-4-nitrophenyl)pyridin-2(1H)-one

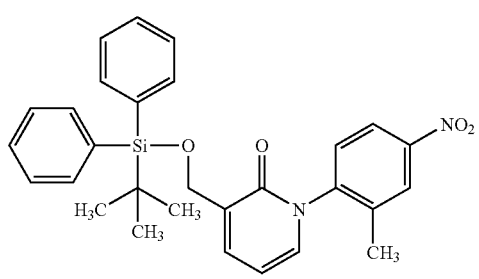

Analogously to Example 4A, 1.50 g (4.13 mmol) of the compound from Example 3A are reacted with 704 mg (4.54 mmol) of 2-fluoro-5-nitrotoluene. This gives 570 mg (28% of theory) of the title compound.

$^1$H-NMR (400 MHz, DMSO-d$_6$, δ/ppm): 8.29 (d, 1H), 8.17 (dd, 1H), 7.76 (dd, 1H), 7.67-7.63 (m, 4H), 7.57 (d, 1H), 7.53 (dd, 1H), 7.51-7.41 (m, 6H), 6.52 (t, 1H), 4.63-4.51 (m, 2H), 2.12 (s, 3H), 1.07 (s, 9H).

HPLC (method 4): R$_t$=3.39 min.
MS (ESIpos, m/z): 499 (M+H)$^+$.

Example 8A 1-(4-Amino-2-methylphenyl)-3-({[tert-butyl(diphenyl)silyl]oxy}methyl)pyridin-2(1H)-one

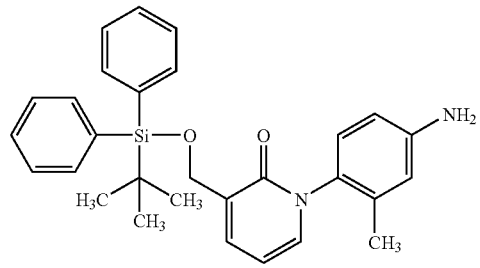 [SMILES: Cc1cc([N+](=O)[O-])ccc1-n1cccc(CO[Si](c2ccccc2)(c2ccccc2)C(C)(C)C)c1=O]

555 mg (1.11 mmol) of the compound from Example 7A are dissolved in 15 ml of THF, 150 mg of palladium on carbon are added and the mixture is hydrogenated in a hydrogen atmosphere at atmospheric pressure until the theoretical amount of hydrogen has been taken up. The catalyst is filtered off, which gives, after concentration under reduced pressure, 520 mg (99% of theory) of the title compound.

$^1$H-NMR (400 MHz, DMSO-d$_6$, δ/ppm): 7.70-7.63 (m, 5H), 7.51-7.41 (m, 6H), 7.40-7.36 (m, 1H), 6.78 (d, 1H), 6.47-6.41 (m, 2H), 6.38 (t, 1H), 5.22 (s, broad, 2H), 4.59-4.48 (m, 2H), 1.81 (s, 3H), 1.06 (s, 9H).

HPLC (method 5): R$_t$=3.20 min.
MS (ESIpos, m/z): 469 (M+H)$^+$.

Example 9A

N-[((5S)-3-{4-[3-({[tert-Butyl(diphenyl)silyl]oxy}methyl)-2-oxopyridin-1(2H)-yl]-3-methyl-phenyl}-2-oxo-1,3-oxazolidin-5-yl)methyl]-5-chlorothiophene-2-carboxamide

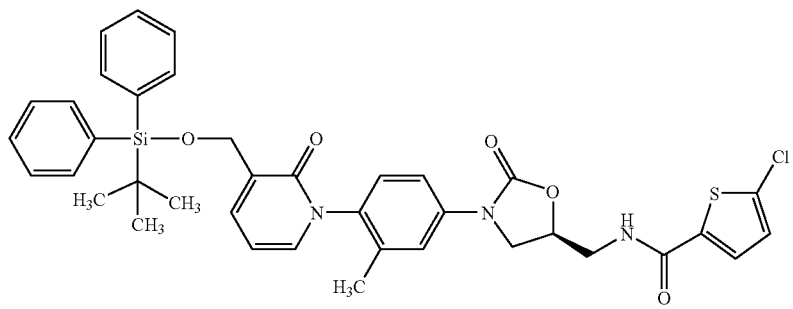 [SMILES: Cc1cc(N2C[C@H](CNC(=O)c3ccc(Cl)s3)OC2=O)ccc1-n1cccc(CO[Si](c2ccccc2)(c2ccccc2)C(C)(C)C)c1=O]

522 mg (1.11 mmol) of the compound from Example 8A are dissolved in 10 ml of acetonitrile, and 266 mg (1.22 mmol) of the compound from Example 1A are added at 0° C. 373 mg (1.67 mmol) of magnesium perchlorate are added, and the mixture is stirred at RT for 20 h. 271 mg (1.67 mmol) of 1,1'-carbonyldiimidazole and 14 mg (0.11 mmol) of DMAP are then added, and the reaction mixture is heated at 60° C. for 20 h. The mixture is then concentrated under reduced pressure, and water and tert-butyl methyl ether are added. The mixture is extracted twice with ethyl acetate. The combined organic phases are dried over sodium sulphate and concentrated. The residue is purified by preparative HPLC. This gives 562 mg (71% of theory) of the desired product.

$^1$H-NMR (400 MHz, DMSO-d$_6$, δ/ppm): 8.97 (t, 1H), 7.74-7.63 (m, 6H), 7.58-7.41 (m, 9H), 7.23 (d, 1H), 7.19 (d, 1H), 6.45 (t, 1H), 4.89-4.80 (m, 1H), 4.58-4.49 (m, 2H), 4.21 (t, 1H), 3.90-3.83 (m, 1H), 3.63-3.58 (m, 2H), 1.98 (s, 3H), 1.07 (s, 9H).

HPLC (method 4): R$_t$=3.39 min.
MS (ESIpos, m/z): 712/714 ($^{35}$Cl/$^{37}$Cl) (M+H)$^+$.

Example 10A

5-Chloro-N-[((5S)-3-{4-[3-(hydroxymethyl)-2-oxopyridin-1(2H)-yl]-3-methylphenyl}-2-oxo-1,3-oxazolidin-5-yl)methyl]thiophene-2-carboxamide

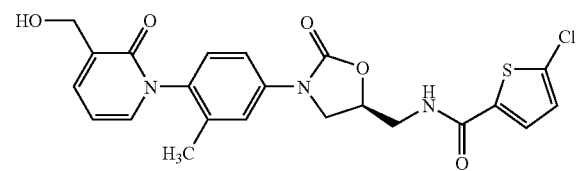 [SMILES: Cc1cc(N2C[C@H](CNC(=O)c3ccc(Cl)s3)OC2=O)ccc1-n1cccc(CO)c1=O]

530 mg (0.74 mmol) of the compound from Example 9A are dissolved in 9 ml THF. 1.5 ml of a 1 molar solution of tetrabutylammonium fluoride in THF are added, and the mixture is stirred at RT for 30 min. A little water is added, the mixture is concentrated and the product is purified by preparative HPLC. This gives 335 mg (93% of theory) of the desired product.

$^1$H-NMR (400 MHz, DMSO-d$_6$, δ/ppm): 9.00 (t, 1H), 7.70 (d, 1H), 7.55-7.49 (m, 3H), 7.39 (d, 1H), 7.23 (d, 1H), 7.20 (d, 1H), 6.36 (t, 1H), 5.14 (s, broad, 1H), 4.90-4.82 (m, 1H), 4.38-4.29 (m, 2H), 4.22 (t, 1H), 3.91-3.85 (m, 1H), 3.62 (t, 2H), 2.01 (s, 3H).

HPLC (method 3): R$_t$=1.66 min.
MS (ESIpos, m/z): 474/476 ($^{35}$Cl/$^{37}$Cl) (M+H)$^+$.

Example 11A

N-{[(5S)-3-{4-[3-(Bromomethyl)-2-oxopyridin-1(2H)-yl]-3-methylphenyl}-2-oxo-1,3-oxazolidin-5-yl]methyl}-5-chlorothiophene-2-carboxamide

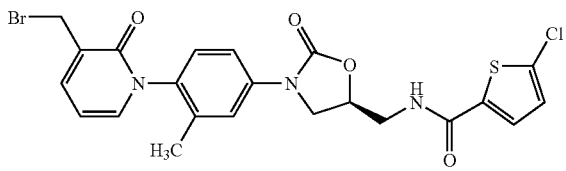 [SMILES: Cc1cc(N2C[C@H](CNC(=O)c3ccc(Cl)s3)OC2=O)ccc1-n1cccc(CBr)c1=O]

50 mg (0.11 mmol) of the product from Example 10A are dissolved in 1 ml of dichloromethane. 0.024 ml (0.32 mmol) of thionyl bromide is added, and the mixture is stirred at RT for 1.5 h. The mixture is diluted with 1 ml of methanol and 3 ml of dichloromethane, and the solvent is then removed under reduced pressure. The crude product is reacted further without further purification.

Example 12A

3-Bromo-1-(2-methyl-4-nitrophenyl)pyridin-2(1H)-one

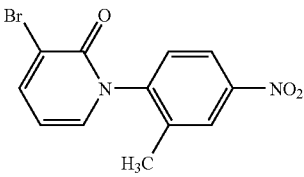 [SMILES: Cc1cc([N+](=O)[O-])ccc1-n1cccc(Br)c1=O]

44.5 g (280 mmol) of 3-bromopyridin-2(1H)-one are dissolved in 750 ml of anhydrous dimethyl sulphoxide, and 33.4 g (298 mmol) of potassium tert-butoxide are added a little at a time at room temperature. The suspension is stirred at this temperature for 1 h, 38.5 g (280 mmol) of 1-fluoro-2-methyl-4-nitrobenzene are then added and the reaction solution is heated at 80° C. for 20 h. The solution is allowed to cool and carefully diluted with water. The resulting crystalline precipitate is filtered off, washed with a little water and dried under reduced pressure. This gives 62 g (80% of theory) of the desired product.

$^1$H-NMR (400 MHz, DMSO-d$_6$, δ/ppm): δ=8.34 (d, 1H), 8.21 (dd, 1H), 8.10 (dd, 1H), 7.71-7.63 (m, 2H), 6.36 (t, 1H), 2.17 (s, 3H).

LC-MS (method 3): R$_t$=1.72 min
MS (ESIpos): m/z=309 (M+H)$^+$

Example 13A 1-(2-Methyl-4-nitrophenyl)-3-vinylpyridin-2(1H)-one

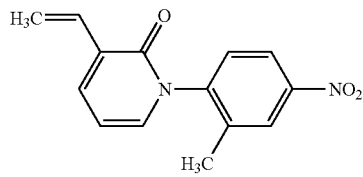

50 g (162 mmol) of the compound from Example 12A are dissolved in 700 ml of anhydrous dioxane, 62 g (194 mmol) of tributylvinyltin and 4.7 g (4 mmol) of tetrakis(triphenylphosphine)palladium are added and the mixture is heated at reflux for 15 h. The mixture is allowed to cool and filtered through kieselguhr. The filter cake is washed with ethyl acetate and the combined filtrates are evaporated to dryness under reduced pressure. The residue is applied to silica gel and chromatographed on 800 g of silica gel using a gradient of cyclohexane and ethyl acetate. This gives 27 g (62% of theory) of the desired product.

$^1$H-NMR (400 MHz, DMSO-d$_6$, δ/ppm): δ=8.35 (d, 1H), 8.2 (dd, 1H), 7.75 (dd, 1H), 7.60 (d, 1H), 7.55 (dd, 1H), 6.75 (dd, 1H), 6.45 (t, 1H), 6.15 (dd, 1H), 5.30 (dd, 1H), 2.17 (s, 3H).

LC-MS (method 4): R$_t$=1.86 min
MS (ESIpos): m/z=257 (M+H)$^+$

Example 14A 3-(2-Hydroxyethyl)-1-(2-methyl-4-nitrophenyl)pyridin-2(1H)-one

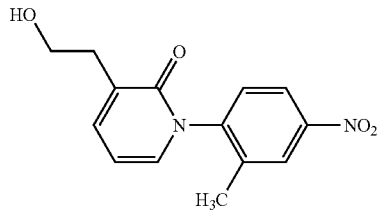 [SMILES: Cc1cc([N+](=O)[O-])ccc1-n1cccc(CCO)c1=O]

With ice-cooling, a solution of 40 g (326 mmol) of 9-borabicyclo[3.3.1]nonane in 650 ml of tetrahydrofuran is added over a period of 45 min to 38 g (148 mmol) of the compound from Example 13A. The mixture is stirred at this temperature for another hour, and a solution of 30 g (747 mmol) of sodium hydroxide in 740 ml of water is then added over a period of 15 min. 151 ml of a 30% strength hydrogen peroxide solution are added such that the temperature does not exceed 30° C. After the addition has ended, the cooling is removed and stirring is continued for a further 30 min. The mixture is repeatedly extracted with ethyl acetate, the combined organic phases are washed with a solution of 780 g (1.63 mol) of sodium disulphite, the organic phase is separated off and the aqueous phase is again extracted with ethyl acetate. The combined organic phases are washed with saturated sodium chloride solution, dried over magnesium sulphate and evaporated to dryness under reduced pressure. The residue is applied to silica gel and chromatographed using a gradient of cyclohexane and ethyl acetate. The product-containing fractions are combined and concentrated to dryness under reduced pressure. This gives 38 mg (93% of theory) of the desired product.

$^1$H-NMR (400 MHz, DMSO-d$_6$, δ/ppm): δ=8.33 (d, 1H), 8.18 (d, 1H), 7.57 (d, 1H), 7.48-7.40 (m, 2H), 6.33 (t, 1H), 4.58 (t, 1H), 3.62-3.50 (m, 2H), 2.62 (t, 2H), 2.15 (s, 3H).

LC-MS (method 6): R$_t$=1.57 min
MS (ESIpos): m/z=275 (M+H)$^+$

Example 15A 3-(2-{[tert-Butyl(diphenyl)silyl]oxy}ethyl)-1-(2-methyl-4-nitrophenyl)pyridin-2(1H)-one

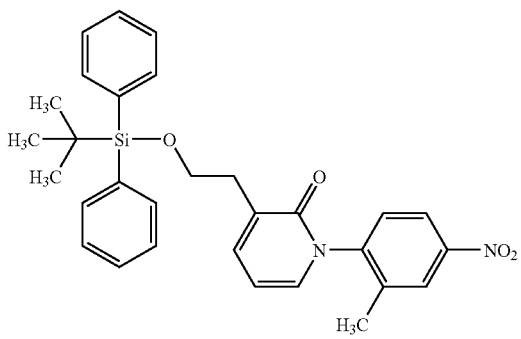

38 g (138 mmol) of the compound from Example 14A are dissolved in 200 ml of anhydrous N,N-dimethylformamide, and 12.2 g (198 mmol) of imidazole and, a little at a time, 46 g (135 mmol) of tert-butyl(chloro)diphenylsilane are added at 0° C. The mixture is stirred overnight and then diluted with water and extracted three times with ethyl acetate. The combined organic phases are washed twice with saturated sodium chloride solution, dried over magnesium sulphate, filtered and evaporated under reduced pressure. The residue is applied to silica gel and chromatographed using a gradient of cyclohexane and ethyl acetate. The product-containing fractions are combined and evaporated to dryness under reduced pressure. This gives 62 g (88% of theory) of the desired product.

LC-MS (method 5): $R_t$=3.18 min
MS (ESIpos): m/z=483 (M+H)$^+$

Example 16A 1-(4-Amino-2-methylphenyl)-3-(2-{[tert-butyl (diphenyl)silyl]oxy}ethyl)pyridin-2(1H)-one

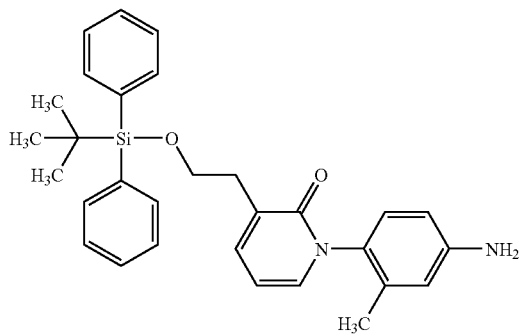 [SMILES: Cc1cc(N)ccc1-n1cccc(CCO[Si](c2ccccc2)(c2ccccc2)C(C)(C)C)c1=O]

62 g (121 mmol) of the compound from Example 15A are dissolved in 2 l of a 1:1 mixture of ethanol and ethyl acetate, and 46 g (726 mmol) of ammonium formate and 0.6 g of palladium on carbon are added. The mixture is heated at 80° C. After 45 min, the mixture is allowed to cool and filtered through silica gel. The filter cake is washed with ethyl acetate and the filtrate is evaporated to dryness under reduced pressure. This gives 36 g (61% of theory) of the desired product.

LC-MS (method 7): $R_t$=1.84 min
MS (ESIpos): m/z=221 (M+H)$^+$

Example 17A

N-[((5S)-3-{4-[3-(2-{[tert-Butyl(diphenyl)silyl] oxy}ethyl)-2-oxopyridin-1(2H)-yl]-3-methyl-phenyl}-2-oxo-1,3-oxazolidin-5-yl)methyl]-5-chlorothiophene-2-carboxamide

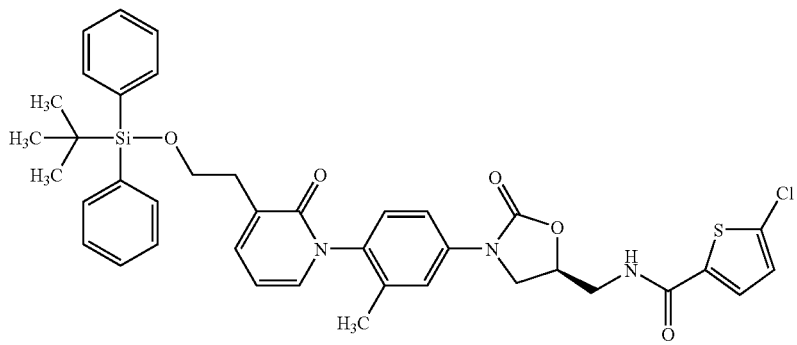 [SMILES: Cc1cc(N2C[C@H](CNC(=O)c3ccc(Cl)s3)OC2=O)ccc1-n1cccc(CCO[Si](c2ccccc2)(c2ccccc2)C(C)(C)C)c1=O]

35.6 g (74.1 mmol) of the compound from Example 16A are dissolved in 800 ml of anhydrous acetonitrile, and 19 g (89 mmol) of the compound from Example 1A are added at 0° C. 25 g (110 mmol) of magnesium perchlorate are added, the cooling is removed and the mixture is stirred at room temperature for 15 h. 24 mg (148 mmol) of 1,1-carbonyldiimidazole and 180 mg (1.4 mmol) of N,N-dimethylaminopyridine are added, and the mixture is heated at reflux for 2 h. The mixture is allowed to cool and the solvent is distilled off under reduced pressure. The residue is then taken up in ethyl acetate and washed with water and, three times, with saturated sodium chloride solution. After drying over magnesium sulphate, the mixture is filtered and evaporated to dryness under reduced pressure. The residue is applied to silica gel and chromatographed using a gradient of cyclohexane and ethyl acetate. The product-containing fractions are combined and evaporated to dryness under reduced pressure. This gives 46.4 g (84% of theory) of the desired product.

LC-MS (method 5): $R_t$=3.31 min
MS (ESIpos): m/z=700 (M+H)$^+$

Example 18A

5-Chloro-N-[((5S)-3-{4-[3-(2-hydroxyethyl)-2-oxopyridin-1(2H)-yl]-3-methylphenyl}-2-oxo-1,3-oxazolidin-5-yl)methyl]thiophene-2-carboxamide

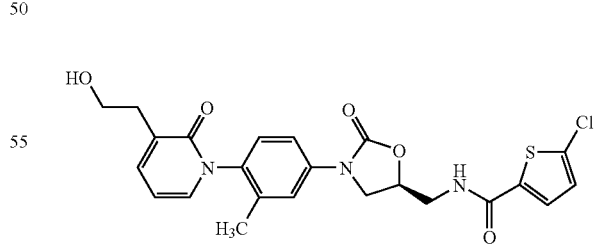

With ice-cooling, 400 ml of 1.25N hydrochloric acid in methanol are added to 43.8 g (60.3 mmol) of the compound from Example 17A. After 1 h, the mixture is diluted with dichloromethane, and the aqueous phase is then separated off. The organic phase is washed twice with water, dried over sodium sulphate and, after filtration, concentrated to dryness under reduced pressure. The residue is applied to silica gel and chromatographed using a gradient of cyclohexane and ethyl acetate. The product-containing fractions are combined and concentrated to dryness under reduced pressure. This gives 19.6 g (66% of theory) of the desired product.

$^1$H-NMR (400 MHz, DMSO-d$_6$, δ/ppm): δ=8.98 (t, 1H), 7.70 (d, 1H), 7.55-7.47 (m, 2H), 7.40 (dd, 1H), 7.35 (dd, 1H), 7.25-7.17 (m, 2H), 6.26 (t, 1H), 4.90-4.82 (m, 1H), 4.60 (t, 1H), 4.22 (t, 1H), 3.92-3.84 (m, 1H), 3.66-3.54 (m, 4H), 2.60 (t, 2H), 2.01 (s, 3H).

LC-MS (method 5): R$_t$=1.87 min
MS (ESIpos): m/z=488 (M+H)$^+$

Example 19A

3-Bromo-1-(2-methoxy-4-nitrophenyl)pyridin-2(1H)-one

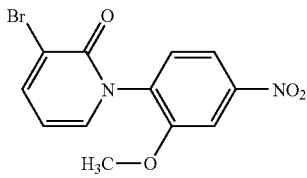 [SMILES: COc1cc([N+](=O)[O-])ccc1-n1cccc(Br)c1=O]

70 g (403 mmol) of 3-bromopyridin-2(1H)-one are dissolved in 1 l of anhydrous dimethyl sulphoxide, and 54 g (484 mmol) of potassium tert-butoxide are added at room temperature. The suspension is stirred at this temperature for 1 h. 69 g (403 mmol) of 1-fluoro-2-methoxy-4-nitrobenzene are added, and the reaction solution is heated at 80° C. for 20 h. Carefully, the mixture is diluted with 5 l of water. The precipitated solid is filtered off, washed with water and dried under reduced pressure. This gives 103 g (72% of theory) of the desired product.

$^1$H-NMR (400 MHz, DMSO-d$_6$, δ/ppm): δ=8.05 (dd, 1H), 8.1 (d, 1H), 7.95 (dd, 1H), 7.7 (d, 1H), 7.6 (dd, 1H), 6.3 (t, 1H), 3.9 (s, 3H).

MS (ESIpos): m/z=342 (M+NH$_4$)$^+$

Example 20A 1-(2-Methoxy-4-nitrophenyl)-3-vinylpyridin-2(1H)-one

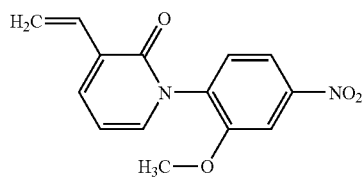 [SMILES: C=Cc1cccn(-c2ccc([N+](=O)[O-])cc2OC)c1=O]

100 g (308 mmol) of the compound from Example 19A are dissolved in 1.4 l of anhydrous dioxane, and 8.9 g (7.7 mmol) of tetrakis(triphenylphospine)palladium and 117 g (370 mmol) of tributylvinyltin are added. The mixture is heated at reflux for 16 h. The reaction solution is then allowed to cool and filtered through kieselguhr. The filtrates are concentrated to dryness under reduced pressure. The residue is chromatographed on silica gel using a gradient of cyclohexane and ethyl acetate. The product-containing fractions are combined and concentrated to dryness under reduced pressure. Petroleum ether is added until crystallization sets in. The crystals are filtered off and dried under reduced pressure. This gives 37 g (41% of theory) of the desired product.

$^1$H-NMR (400 MHz, DMSO-d$_6$, δ/ppm): δ=8.0 (m, 2H), 7.7 (m, 2H), 7.5 (dd, 1H), 6.7 (q, 1H), 6.4 (t, 1H), 6.1 (dd, 1H), 5.3 (dd, 1H), 3.9 (s, 3H).

MS (ESIpos): m/z=273 (M+H)$^+$

Example 21A 3-(2-Hydroxyethyl)-1-(2-methoxy-4-nitrophenyl)pyridin-2(1H)-one

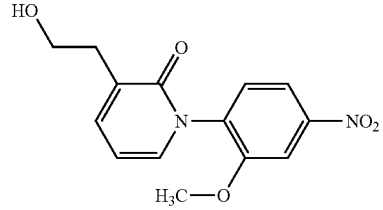 [SMILES: COc1cc([N+](=O)[O-])ccc1-n1cccc(CCO)c1=O]

At 0° C., a solution of 36 g (299 mmol) of 9-borabicyclo[3.3.1]nonane in 600 ml of tetrahydrofuran is added over a period of 45 min to 37 g (136 mmol) of the compound from Example 20A. After a further hour at this temperature, a solution of 27 g (680 mmol) of sodium hydroxide (1N in water) is added over the course of 15 min. The mixture is stirred for a further 5 min, and 125 ml of a 30% strength hydrogen peroxide solution are then added such that the temperature does not exceed 30° C. Cooling is removed, and the mixture is stirred for another 30 min. The mixture is extracted repeatedly with ethyl acetate, the combined organic phases are washed with a solution of 730 g (1.50 mol) of sodium disulphite, the organic phase is separated off and the aqueous phase is reextracted with ethyl acetate. The combined organic phases are washed with saturated sodium chloride solution, dried over magnesium sulphate and evaporated to dryness under reduced pressure. The residue is absorbed on silica gel and chromatographed using a gradient of cyclohexane and ethyl acetate. The product fractions are combined and evaporated to dryness under reduced pressure. For crystallization, tert-butyl methyl ether is added. The crystals are filtered off and dried under reduced pressure. This gives 24 g (60% of theory) of the desired product.

$^1$H-NMR (400 MHz, DMSO-d$_6$, δ/ppm): δ=8.0 (d, 1H), 7.95 (dd, 1H), 7.6 (d, 1H), 7.4 (d, 1H), 6.35 (t, 1H), 4.6 (t, 1H), 3.9 (s, 3H), 3.55 (m, 2H), 2.6 (m, 2H).

MS (ESIpos): m/z=291 (M+H)$^+$

Example 22A 3-(2-{[tert-Butyl(diphenyl)silyl]oxy}ethyl)-1-(2-methoxy-4-nitrophenyl)pyridin-2(1H)-one

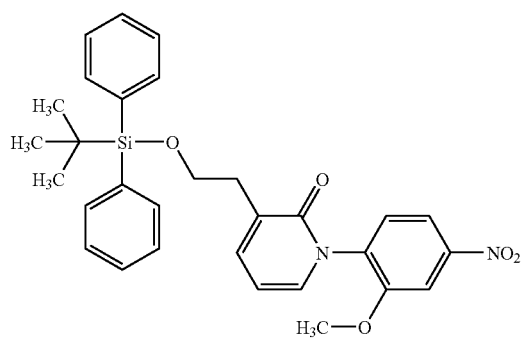 [SMILES: COc1cc([N+](=O)[O-])ccc1-n1cccc(CCO[Si](c2ccccc2)(c2ccccc2)C(C)(C)C)c1=O]

24 g (81 mmol) of the compound from Example 21A are dissolved in 200 ml of anhydrous N,N-dimethylformamide, and 7.2 g (106 mmol) of imidazole and 27 g (98 mmol) of tert-butyl(chloro)diphenylsilane are added. After 16 h, the mixture is diluted with 1.2 l of water and extracted three times with ethyl acetate. The combined organic phases are washed twice with water, dried over magnesium sulphate, filtered and concentrated under reduced pressure. For crystallization, tert-butyl methyl ether is added, and the resulting crystals are filtered off and dried under reduced pressure. This gives 30 g (67% of theory) of the desired product.

$^1$H-NMR (400 MHz, DMSO-d$_6$, S/ppm): δ=8.0 (d, 1H), 7.95 (dd, 1H), 7.6-7.5 (m, 5H), 7.5-7.4 (m, 8H), 6.35 (t, 1H), 3.8 (m, 5H), 2.7 (m, 2H), 1.0 (s, 9H).

Example 23A 1-(4-Amino-2-methoxyphenyl)-3-(2-{[tert-butyl(diphenyl)silyl]oxy}ethyl)pyridin-2(1H)-one

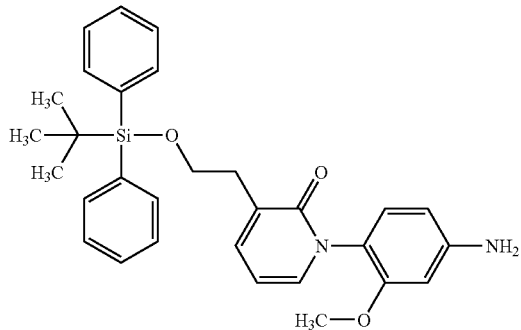

25 g (48 mmol) of the compound from Example 22A are dissolved in 800 ml of a 1:1 mixture of ethanol and ethyl acetate, and 18 g (286 mmol) of ammonium formate and 800 mg of palladium on carbon are added. The mixture is heated at 80° C. After 60 min, the mixture is allowed to cool and filtered through silica gel. The filter cake is washed with ethyl acetate, and the filtrate is concentrated to dryness under reduced pressure. This gives 27 g (98% of theory) of the desired product.

$^1$H-NMR (400 MHz, DMSO-d$_6$, δ/ppm): δ=7.6 (m, 4H), 7.4 (m, 6H), 7.3 (dd, 1H), 7.25 (dd, 1H), 6.75 (d, 1H), 6.3 (d, 1H), 6.2 (dd, 1H), 6.1 (t, 1H), 5.3 (b, 2H), 3.8 (m, 2H), 3.6 (s, 3H), 2.7 (m, 2H), 1.0 (s, 9H).

MS (ESIpos): m/z=499 (M+H)$^+$

Example 24A

N-{[(5S)-3-{4-[3-(2-{[tert-Butyl(diphenyl)silyl]oxy}ethyl)-2-oxopyridin-1(2H)-yl]-3-methoxy-phenyl}-2-oxo-1,3-oxazolidin-5-yl]methyl}-5-chlorothiophene-2-carboxamide

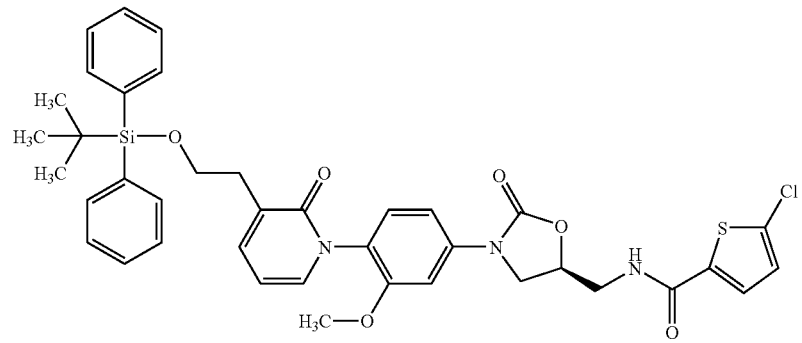 [SMILES: COc1cc(N2C[C@H](CNC(=O)c3ccc(Cl)s3)OC2=O)ccc1-n1cccc(CCO[Si](c2ccccc2)(c2ccccc2)C(C)(C)C)c1=O]

29 g (58 mmol) of the compound from Example 23A are dissolved in 600 ml of anhydrous acetonitrile, and 15 g (69 mmol) of the compound from Example 1A are added at 0° C. 19 g (87 mmol) of magnesium perchlorate are added, cooling is removed and the mixture is stirred at RT for 15 h. 19.0 g (116 mmol) of 1,1-carbonyldiimidazole and 141 mg (1.21 mmol) of N,N-dimethylaminopyridine are then added, and the mixture is heated at reflux. After 2 h, the mixture is allowed to cool and the solvent is distilled off under reduced pressure. The residue is taken up in ethyl acetate and washed with water and three times with saturated sodium chloride solution. After drying over magnesium sulphate, the mixture is filtered and evaporated to dryness under reduced pressure. The residue is chromatographed on silica gel using a gradient of cyclohexane and ethyl acetate. The product-containing fractions are combined and concentrated to dryness under reduced pressure. This gives 37 g (85% of theory) of the desired product.

$^1$H-NMR (400 MHz, DMSO-d$_6$): δ=9.0 (t, 1H), 7.7 (d, 1H), 7.6 (m, 4H), 7.5-7.3 (m, 9H), 7.2 (m, 2H), 7.1 (m, 1H), 6.2 (t, 1H), 4.8 (m, 1H), 4.4 (t, 1H), 3.9 (m, 1H), 3.8 (b, 2H), 3.7 (s, 3H), 3.65 (m, 2H), 2.7 (m, 2H), 1.0 (s, 9H).

LC-MS (method 8): R$_t$=4.53 min
MS (ESIpos): m/z=742 (M+H)$^+$

Example 25A

5-Chloro-N-{[(5S)-3-{4-[3-(2-hydroxyethyl)-2-oxopyridin-1(2H)-yl]-3-methoxyphenyl}-2-oxo-1,3-oxazolidin-5-yl]methyl}thiophene-2-carboxamide

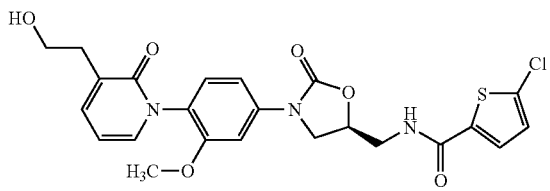 [SMILES: COc1cc(N2C[C@H](CNC(=O)c3ccc(Cl)s3)OC2=O)ccc1-n1cccc(CCO)c1=O]

At 0° C., 37 g (49 mmol) of the compound from Example 24A are dissolved in 313 ml of 1.25N hydrochloric acid in methanol. After 1 h, the solution is evaporated under reduced pressure and diluted with dichloromethane. The organic phase is washed twice with water, dried over magnesium sulphate and, after filtration, evaporated to dryness under reduced pressure. The residue is chromatographed on silica gel using a gradient of dichloromethane and methanol. The product fractions are combined and evaporated to dryness under reduced pressure. This gives 19 g (78% of theory) of the desired product.

$^1$H-NMR (400 MHz, DMSO-$d_6$, δ/ppm): δ=9.00 (t, 1H), 7.70 (d, 1H), 7.45 (d, 1H), 7.35 (dd, 1H), 7.30 (dd, 1H), 7.25 (d, 1H), 7.20 (d, 1H), 7.15-7.08 (m, 1H), 6.19 (t, 1H), 4.91-4.83 (m, 1H), 4.60 (t, 1H), 4.25 (t, 1H), 3.94-3.87 (m, 1H), 3.73 (s, 3H), 3.66-3.53 (m, 4H), 2.62-2.55 (m, 2H).

MS (ESIpos): m/z=504 (M+H)$^+$

Example 26A 2-(Bromomethyl)-1-fluoro-4-nitrobenzene

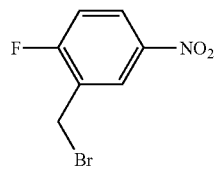 [SMILES: O=[N+]([O-])c1ccc(F)c(CBr)c1]

186 g (1.20 mol) of 2-fluoro-5-nitrotoluene are dissolved in 1.2 l of carbon tetrachloride, and 214 g (1.20 mol) of N-bromosuccinimide are added. 19.7 g (120 mmol) of azodiisobutyronitrile are added, and the mixture is heated under reflux. After 16 h, the mixture is allowed to cool, filtered and evaporated to dryness under reduced pressure. The residue is dissolved in 300 ml of dichloromethane, and 300 g of sea sand are added. Once more, the mixture is then concentrated to dryness under reduced pressure, and the residue is applied to a 1 kg silica gel column. The product is chromatographed using a 20:1 mixture of cyclohexane and ethyl acetate, and the product fractions are evaporated to dryness under reduced pressure. The residue is crystallized with cyclohexane and dried under reduced pressure. This gives 92 g (32% of theory) of the desired product.

$^1$H-NMR (400 MHz, DMSO-$d_6$, δ/ppm): δ=8.57-8.52 (m, 1H), 8.33-8.27 (m, 1H), 7.56 (t, 1H), 4.62 (s, 2H).

GC-MS (method 9): $R_t$=7.79 min
MS (ESIpos): m/z=154 (M−Br)$^+$

Example 27A

1-Fluoro-2-(methoxymethyl)-4-nitrobenzene

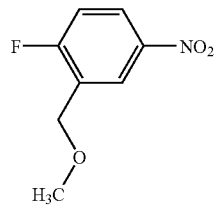

30 g (128 mmol) of the compound from Example 26A are dissolved in 1.3 l of anhydrous toluene, and 45 g (192 mmol) of silver(I) oxide and 24.6 g (769 mmol) of anhydrous methanol are added. The mixture is heated at 60° C. for 16 h. The mixture is then allowed to cool and filtered through silica gel. The product is eluted fractionally using a gradient of cyclohexane and cyclohexane/ethyl acetate 25:1. The product fractions are evaporated to dryness under reduced pressure and dried under reduced pressure. This gives 17 g (72% of theory) of the desired product.

$^1$H-NMR (400 MHz, DMSO-$d_6$, δ/ppm): δ=8.41-8.36 (m, 1H), 8.22-8.16 (m, 1H), 7.26 (t, 1H), 4.58 (s, 2H), 3.49 (s, 3H).

GC-MS (method 9): $R_t$=6.52 min
MS (ESIpos): m/z=154 (M−OCH$_3$)$^+$

Example 28A

3-Bromo-1-[2-(methoxymethyl)-4-nitrophenyl]pyridin-2(1H)-one

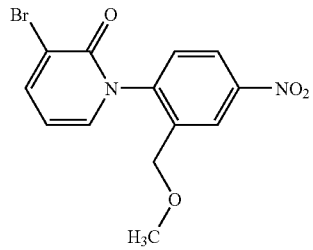 [SMILES: COCc1cc([N+](=O)[O-])ccc1-n1cccc(Br)c1=O]

38 g (391 mmol) of 3-bromo-2-hydroxypyridine are dissolved in 1250 ml of anhydrous dimethyl sulphoxide, and 53 g (469 mmol) of potassium tert-butoxide are added a little at a time. The mixture is stirred for another hour, and 72.4 g (391 mmol) of the compound from Example 27A are then added. After the addition has ended, the mixture is heated at 80° C. for 3 h. The mixture is then allowed to cool, and stirring is continued at room temperature for a further 16 h. The reaction solution is then cooled to 15° C., and at this temperature the pH is carefully adjusted with 1N hydrochloric acid to pH=3.4 1 of water are added, and the mixture is extracted three times with 2 l of ethyl acetate. The combined organic phases are washed with saturated sodium chloride solution and dried over magnesium sulphate. The solutions are then evaporated to dryness under reduced pressure, and tert-butyl methyl ether is added for crystallization. The crystals are filtered off and dried under reduced pressure. This gives 94 g (71% of theory) of the desired product.

$^1$H-NMR (400 MHz, DMSO-$d_6$, δ/ppm): δ=8.37 (d, 1H), 8.33 (dd, 1H), 8.10 (dd, 1H), 7.73-7.67 (m, 2H), 6.35 (t, 1H), 4.3 (q, 2H), 3.3 (s, 3H).

LC-MS (method 6): $R_t$=1.88 min
MS (ESIpos): m/z=339 (M+H$^+$)$^+$

Example 29A

1-[2-(Methoxymethyl)-4-nitrophenyl]-3-vinylpyridin-2(1H)-one

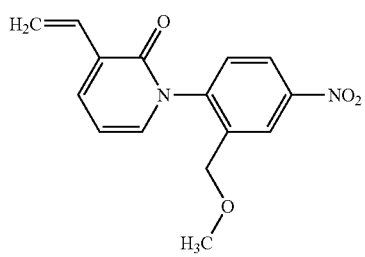 [SMILES: C=Cc1cccn(-c2ccc([N+](=O)[O-])cc2COC)c1=O]

94 g (277 mmol) of the compound from Example 28A are dissolved in 1.2 l of anhydrous dioxane, and 8 g (6.9 mmol) of tetrakis(triphenylphosphine)palladium(0) are added. At room temperature, 105 g (333 mmol) of tributylvinyltin are added slowly, and after the addition has ended, the mixture is heated at reflux for 21 h. The reaction solution is allowed to cool and filtered through kieselguhr. The filter cake is washed with ethyl acetate and the combined organic filtrates are concentrated to dryness under reduced pressure. The residue that remains is dissolved in dichloromethane and applied to kieselguhr. The product is chromatographed on 1.2 kg of silica gel using a gradient of cyclohexane and ethyl acetate. The product-containing fractions are combined and concentrated to dryness under reduced pressure. This gives 23 g (29% of theory) of the desired product.

$^1$H-NMR (400 MHz, DMSO-d$_6$, δ/ppm): δ=8.36 (d, 1H), 8.31 (dd, 1H), 7.77 (dd, 1H), 7.67 (d, 1H), 7.56 (dd, 1H), 6.80-6.71 (m, 1H), 6.45 (t, 1H), 6.14 (dd, 1H), 5.33 (dd, 1H), 4.37-4.22 (m, 2H), 3.26 (s, 3H).

LC-MS (method 6): R$_t$=2.07 min
MS (ESIpos): m/z=387 (M+H$^+$)$^+$

Example 30A 3-(2-Hydroxyethyl)-1-[2-(methoxymethyl)-4-nitrophenyl]pyridin-2(1H)-one

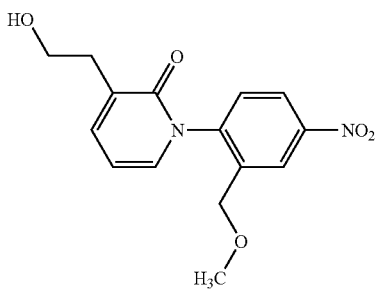 [SMILES: COCc1cc([N+](=O)[O-])ccc1-n1cccc(CCO)c1=O]

23 g (80 mmol) of the compound from Example 29A are dissolved in 80 ml of anhydrous tetrahydrofuran and cooled to 5° C. Over a period of 15 min, 21 g (176 mmol) of 9-borabicyclo[3.3.1]nonane (0.5M solution in tetrahydrofuran) are added. Cooling is removed, and the mixture is stirred at room temperature for another 2 h. The mixture is then again cooled to 5° C., and 400 ml of 1N aqueous sodium hydroxide solution are added. After the addition has ended, 81 ml of 30% strength hydrogen peroxide solution are added a little at a time at this temperature. After dilution with 500 ml of ethyl acetate, the mixture is washed with 32 ml of 40% strength sodium bisulphite solution to destroy the peroxides. The organic phase is separated off, and the aqueous phase is extracted four times with ethyl acetate. The combined organic phases are washed with saturated sodium chloride solution, dried over magnesium sulphate and, after filtration, concentrated to dryness under reduced pressure. The residue is chromatographed on silica gel using a gradient of cyclohexane and ethyl acetate. The product-containing fractions are combined and concentrated to dryness under reduced pressure. This gives 20 g (77% of theory) of the desired product.

$^1$H-NMR (400 MHz, DMSO-d$_6$, δ/ppm): δ=8.36 (d, 1H), 8.30 (dd, 1H), 7.62 (d, 1H), 7.45 (d, 1H), 6.33 (t, 1H), 4.60 (t, 1H), 4.35-4.20 (m, 2H), 3.62-3.55 (m, 2H), 3.32 (s, 3H), 2.62 (t, 2H).

LC-MS (method 8): R$_t$=1.60 min
MS (ESIpos): m/z=305 (M+H$^+$)$^+$

Example 31A 3-(2-{[tert-Butyl(diphenyl)silyl]oxy}ethyl)-1-[2-(methoxymethyl)-4-nitrophenyl]pyridin-2(1H)-one

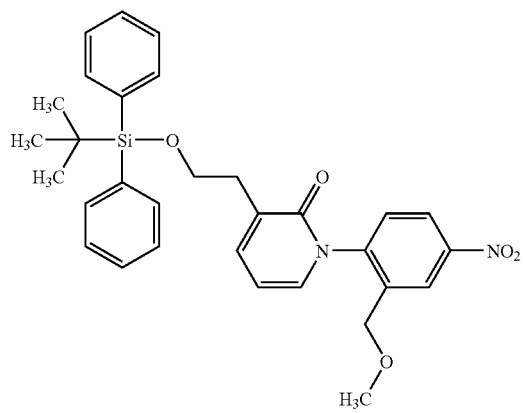

20 g (65 mmol) of the compound from Example 30A are dissolved in 75 ml of anhydrous N,N-dimethylformamide, and, with ice-cooling, first 5.3 g (78 mmol) of imidazole and then, a little at a time over a period of 3 min, 19 g (72 mmol) of tert-butyldiphenylchlorosilane are added. Cooling is removed, and the mixture is stirred at room temperature for a further 19 h. The reaction solution is diluted with ethyl acetate and washed three times with water and twice with saturated sodium chloride solution. The mixture is then dried over magnesium sulphate, filtered and concentrated to dryness under reduced pressure. tert-Butyl methyl ether is added to the residue, and the resulting crystals are filtered off and dried under reduced pressure. This gives 39 g (90% of theory) of the desired product.

$^1$H-NMR (400 MHz, DMSO-d$_6$, δ/ppm): δ=8.35 (d, 1H), 8.31 (dd, 1H), 7.65-7.35 (m, 13H), 6.35 (t, 1H), 4.32-4.14 (m, 2H), 3.92-3.80 (m, 2H), 3.32 (s, 3H), 2.78-2.71 (m, 2H), 0.97 (s, 9H).

LC-MS (method 8): R$_t$=4.59 min
MS (ESIpos): m/z=543 (M+H$^+$)$^+$

Example 32A

1-[4-Amino-2-(methoxymethyl)phenyl]-3-(2-{[tert-butyl(diphenyl)silyl]oxy}ethyl)pyridin-2(1H)-one

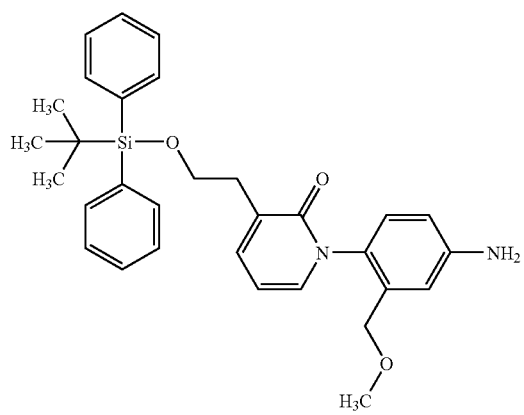 [SMILES: COCc1cc([N+](=O)[O-])ccc1-n1cccc(CCO[Si](c2ccccc2)(c2ccccc2)C(C)(C)C)c1=O]

25 g (48 mmol) of the compound from Example 31A are dissolved in 500 ml of ethyl acetate and 500 ml of ethanol. 18 g (286 mmol) of ammonium formate and 1 g of palladium on carbon are added, and the mixture is heated at reflux for 45 min. The reaction solution is then allowed to cool and filtered through silica gel. The filtrate is concentrated to dryness under reduced pressure. This gives 25 g (100% of theory) of the desired product.

$^1$H-NMR (400 MHz, DMSO-$d_6$, δ/ppm): δ=7.65-7.20 (m, 12H), 6.79 (d, 1H), 6.68 (d, 1H), 6.54 (dd, 1H), 6.20 (t, 1H), 5.46-5.25 (m, 2H), 4.04-3.91 (m, 2H), 3.87-3.77 (m, 2H), 3.07 (s, 3H), 2.75-2.68 (m, 2H), 0.95 (s, 9H).

LC-MS (method 6): $R_t$=3.22 min
MS (ESIpos): m/z=513 (M+H$^+$)$^+$

Example 33A

N-{[(5S)-3-{4-[3-(2-{[tert-Butyl(diphenyl)silyl]oxy}ethyl)-2-oxopyridin-1(2H)-yl]-3-(methoxymethyl)phenyl}-2-oxo-1,3-oxazolidin-5-yl]methyl}-5-chlorothiophene-2-carboxamide

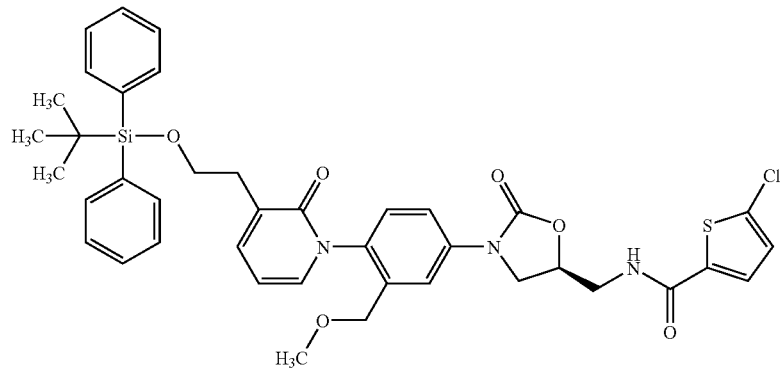 [SMILES: COCc1cc(N2C[C@H](CNC(=O)c3ccc(Cl)s3)OC2=O)ccc1-n1cccc(CCO[Si](c2ccccc2)(c2ccccc2)C(C)(C)C)c1=O]

25 g (47 mmol) of the compound from Example 32A are dissolved in 500 ml of anhydrous acetonitrile, and 15 g (61 mmol) of the compound from Example 1A and 16 g (71 mmol) of magnesium perchlorate are added. The mixture is stirred at room temperature for 5 h, and another 1 g (4.1 mmol) of the compound from Example 1A is then added. After 21 h, 15.3 g (95 mmol) of carbonyldiimidazole and 116 mg (0.65 mmol) of 4-dimethylaminopyridine are added, and the mixture is heated at reflux for 3.5 h. The solvent is then removed under reduced pressure, and the residue is taken up in 800 ml of ethyl acetate. The solution is washed with water and twice with saturated sodium chloride solution, dried over magnesium sulphate and then concentrated under reduced pressure. The residue is separated on silica gel using a gradient of cyclohexane and ethyl acetate. The product-containing fractions are combined and concentrated to dryness under reduced pressure. This gives 26.5 g (72% of theory) of the desired product.

$^1$H-NMR (400 MHz, DMSO-$d_6$, δ/ppm): δ=9.00 (t, 1H), 7.73-7.35 (m, 15H), 7.23 (d, 1H), 7.19 (d, 1H), 6.28 (t, 1H), 4.90-4.81 (m, 1H), 4.28-3.80 (m, 6H), 3.62 (t, 2H), 3.11 (s, 3H), 2.79-2.71 (m, 2H), 0.97 (s, 9H).

LC-MS (method 6): $R_t$=3.39 min
MS (ESIpos): m/z=756 (M+H$^+$)$^+$

Example 34A

N-{[(5S)-3-{4-[3-(2-{[tert-Butyl(diphenyl)silyl]oxy}ethyl)-2-oxopyridin-1(2H)-yl]-3-(methoxymethyl)phenyl}-2-oxo-1,3-oxazolidin-5-yl]methyl}-5-chlorothiophene-2-carboxamide

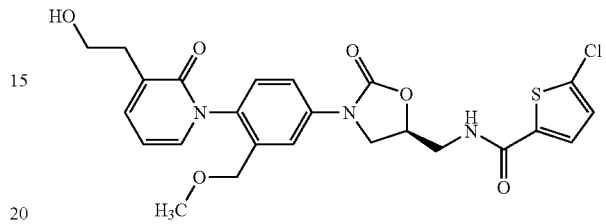

With ice-cooling, 135 ml of 1.25N hydrochloric acid in methanol are added to 27 g (34 mmol) of the compound from Example 33A. The mixture is stirred at this temperature for a further 45 min. With ice-cooling, the mixture is adjusted to pH 7 using 1N aqueous sodium hydroxide solution, and the cold solution is extracted repeatedly with dichloromethane. The combined organic phases are washed with saturated sodium chloride solution and dried over magnesium sulphate. The mixture is evaporated to dryness under reduced pressure, and the residue is chromatographed on silica gel using a gradient of dichloromethane and methanol. The product-containing fractions are combined and concentrated to dryness under reduced pressure. This gives 16.4 g (89% of theory) of the desired product.

$^1$H-NMR (400 MHz, DMSO-$d_6$, δ/ppm): δ=8.98 (t, 1H), 7.72-7.66 (m, 2H), 7.62-7.56 (m, 1H), 7.40 (dd, 1H), 7.36 (dd, 1H), 7.27 (d, 1H), 7.20 (d, 1H), 6.25 (t, 1H), 4.90-4.82 (m, 1H), 4.60 (t, 1H), 4.27-4.08 (m, 3H), 3.94-3.87 (m, 1H), 3.65-3.55 (m, 4H), 3.18 (s, 3H), 2.60 (t, 2H).

LC-MS (method 6): $R_t$=1.96 min
MS (ESIpos): m/z=518 (M+H$^+$)$^+$

Example 35A

3-Allyl-1-(2-methyl-4-nitrophenyl)pyridin-2(1H)-one

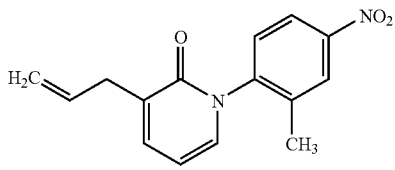 [SMILES: C=CCc1cccn(-c2ccc([N+](=O)[O-])cc2C)c1=O]

In a flask which had been dried by heating, 1.50 g (4.85 mmol) of the compound from Example 12A, 1.44 g (9.46 mmol) of caesium fluoride and 0.56 g (0.48 mmol) of tetrakis-(triphenylphosphine)palladium(0) are initially charged in 30 ml of degassed THF. A solution of 2.04 g (12.1 mmol) of 2-allyl-4,4,5,5-tetramethyl-1,3,2-dioxaborolane in 5 ml of degassed THF is added dropwise, and the mixture is heated at reflux overnight. The mixture is then diluted with dichloromethane, and water is added. After phase separation, the aqueous phase is extracted three times with dichloromethane. The combined organic phases are dried over sodium sulphate and concentrated. The product is purified by chromatography on silica gel, giving 1.18 g (62% of theory) of the title compound.

$^1$H-NMR (400 MHz, DMSO-d$_6$, δ/ppm): 8.31 (d, 1H), 8.18 (dd, 1H), 7.57 (d, 1H), 7.46 (dd, 1H), 7.44-7.38 (m, 1H), 6.35 (t, 1H), 5.96 (dddd, 1H), 5.16-5.06 (m, 2H), 3.20 (d, 2H), 2.15 (s, 3H).

HPLC (method 2): R$_t$=4.05 min.
MS (ESIpos, m/z): 271 (M+H)$^+$.

Example 36A 3-(3-Hydroxypropyl)-1-(2-methyl-4-nitrophenyl)pyridin-2(1H)-one

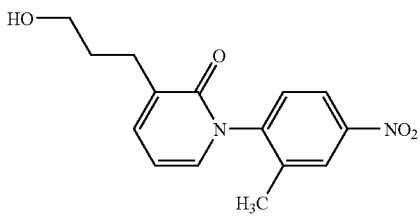 [SMILES: Cc1cc([N+](=O)[O-])ccc1-n1cccc(CCCO)c1=O]

At 0° C., 18.5 ml (9.25 mmol) of a 0.5 molar solution of 9-borabicyclo[3.3.1]nonane in THF are slowly added dropwise to 1.00 g (3.70 mmol) of the compound from Example 35A in 4 ml THF. After one hour at room temperature, the mixture is again cooled to 0° C., and 18.5 ml (18.5 mmol) of a 1 molar solution of sodium hydroxide in water are added dropwise. The mixture is stirred at 0° C. for a further 30 min, and 3.24 ml of a 30% strength hydrogen peroxide solution are then added such that the temperature does not exceed 30° C. The mixture is stirred with ice-cooling for 30 min, and ethyl acetate and then 11 g (40 mmol) of sodium bisulphite solution are then added. The organic phase is separated off, and the aqueous phase is extracted twice with ethyl acetate. The combined organic phases are washed with saturated aqueous sodium chloride solution. The organic phase is dried over sodium sulphate and then evaporated to dryness under reduced pressure. The residue is chromatographed on silica gel (cyclohexane/ethyl acetate 1:4). This gives 1.03 g (83% of theory) of the desired product.

$^1$H-NMR (400 MHz, DMSO-d$_6$, δ/ppm): δ=8.31 (d, 1H), 8.18 (dd, 1H), 7.66-7.51 (m, 1H), 7.47-7.38 (m, 2H), 6.33 (t, 1H), 4.46 (t, 1H), 3.46-3.38 (q, 2H), 2.52-2.45 (m, 2H), 2.15 (s, 3H), 1.73-1.62 (m, 2H).

HPLC (method 1): R$_t$=3.51 min.
MS (DCI, m/z)=289 (M+H)$^+$

Example 37A 1-(4-Amino-2-methylphenyl)-3-(3-hydroxypropyl)pyridin-2(1H)-one

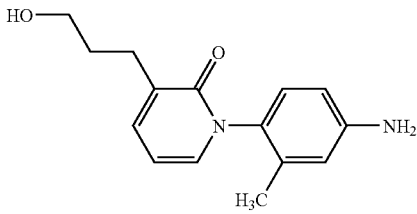 [SMILES: Cc1cc(N)ccc1-n1cccc(CCCO)c1=O]

475 mg (1.65 mmol) of the compound from Example 36A are dissolved in 48 ml of THF. 50 mg (0.05 mmol) of palladium on carbon are then added, and the mixture is hydrogenated at RT in a hydrogen atmosphere under atmospheric pressure. The mixture is then filtered, the filter cake is washed three times with THF and the filtrate is freed from the solvent. The reaction product is reacted further without further purification.

HPLC (method 1): R$_t$=2.82 min.
MS (DCI, m/z): 259 (M+H)$^+$.

Example 38A

5-Chloro-N-{[(5S)-3-{4-[3-(3-hydroxypropyl)-2-oxopyridin-1(2H)-yl]-3-methylphenyl}-2-oxo-1,3-oxazolidin-5-yl]methyl}thiophene-2-carboxamide

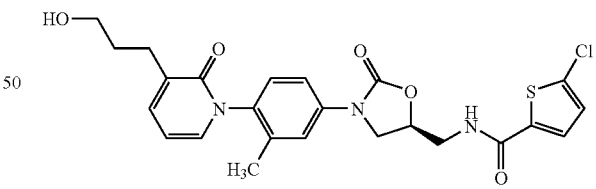

580 mg (2.24 mmol) of the compound from Example 37A are dissolved in 12.7 ml of anhydrous acetonitrile, and 538 mg (2.47 mmol) of the compound from Example 1A and 751 mg (3.37 mmol) of magnesium perchlorate are added. The mixture is stirred at room temperature for 3.5 h. 437 mg (2.69 mmol) of carbonyldiimidazole and 27 mg (0.23 mmol) of 4-dimethylaminopyridine are then added, and the mixture is heated at reflux for 18 h. The mixture is then added to 100 ml of water, and the mixture is extracted three times with 50 ml of ethyl acetate. The combined organic phases are then washed with saturated sodium chloride solution, dried over sodium sulphate and then concentrated under reduced pressure. The residue is purified by preparative HPLC. This gives 175 mg (16% of theory) of the desired product.

$^1$H-NMR (400 MHz, DMSO-d$_6$, δ/ppm): δ=8.99 (t, 1H), 7.70 (d, 1H), 7.57-7.47 (m, 2H), 7.40-7.31 (m, 2H), 7.23 (d, 1H), 7.20 (d, 1H), 6.26 (t, 1H), 4.90-4.81 (m, 1H), 4.46 (dd, 1H), 4.22 (t, 1H), 3.91-3.85 (m, 1H), 3.62 (t, 2H), 3.42 (ddd, 2H), 3.31 (s, 1H), 2.48-2.42 (m, 1H), 2.01 (s, 3H), 1.67 (ddd, 2H).

HPLC (method 2): R$_t$=3.92 min
MS (DCI, m/z)=502 (M+H)$^+$

Example 39A

3-Methoxy-1-(2-methyl-4-nitrophenyl)pyridin-2(1H)-one

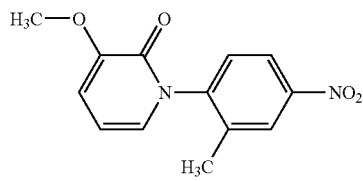

28.5 g (228 mol) of 3-methoxypyridin-2(1H)-one are dissolved in 850 ml of dimethyl sulphoxide, and 31 g (273 mmol) of potassium tert-butoxide are added at RT. The suspension is stirred at RT for 30 min, and 35 g (228 mmol) of 1-fluoro-2-methyl-4-nitrobenzene are then added, and the reaction solution is heated at 80° C. for 20 h. The solution is then carefully diluted with 1 l of water and adjusted to pH 1-2 using 1N hydrochloric acid. The solution is extracted repeatedly with dichloromethane. The combined organic extracts are washed with water and saturated sodium chloride solution, dried over sodium sulphate, filtered and evaporated under reduced pressure. The solid obtained is washed with a little tert-butyl methyl ether, filtered off and dried under reduced pressure. This gives 42.8 g (72% of theory) of the desired compound.

$^1$H-NMR (400 MHz, DMSO-d$_6$, δ/ppm): δ=8.35 (d, 1H), 8.18 (dd, 1H), 7.57 (d, 1H), 7.13 (dd, 1H), 6.95 (dd, 1H), 6.32 (t, 1H), 3.75 (s, 3H), 2.25 (s, 3H).

LC-MS (method 3): R$_t$=1.45 min
MS (ESIpos): m/z=261 (M+H)$^+$

Example 40A

3-Hydroxy-1-(2-methyl-4-nitrophenyl)pyridin-2(1H)-one

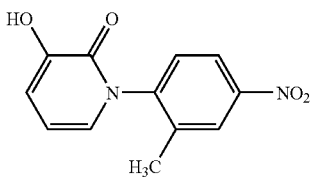 [SMILES: Cc1cc([N+](=O)[O-])ccc1-n1cccc(O)c1=O]

23.3 g (90 mmol) of Example 39A are dissolved in 730 ml of anhydrous dichloromethane and cooled to 0° C. Over a period of 10 minutes, 224 ml (224 mmol) of a 1N boron tribromide solution in dichloromethane are added dropwise, and the mixture is then stirred at this temperature for a further 1.5 h. 200 ml of water are added to the reaction, and the aqueous phase is extracted three times with dichloromethane. The combined organic phases are washed with saturated sodium chloride solution, dried over sodium sulphate and filtered off. The solvent is removed under reduced pressure, and the solid obtained is washed with tert-butyl methyl ether and filtered off. This gives 20.1 g (91% of theory) of the desired compound.

$^1$H-NMR (400 MHz, DMSO-d$_6$, δ/ppm): δ=9.50 (s, 1H), 8.42 (d, 1H), 8.20 (dd, 1H), 7.6 (d, 1H), 7.05 (d, 1H), 6.85 (dd, 1H), 6.25 (t, 1H), 2.25 (s, 3H).

LC-MS (method 3): R$_t$=1.45 min
MS (ESIpos): m/z=246 (M+H)$^+$

Example 41A

3-[(2-Methoxyethoxy)methoxy]-1-(2-methyl-4-nitrophenyl)pyridin-2(1H)-one

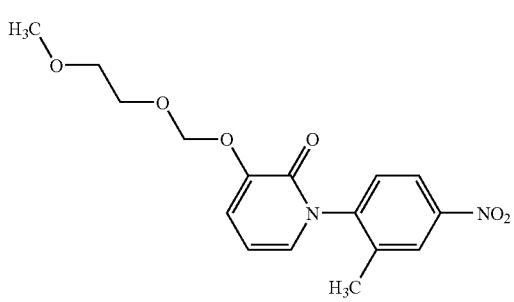

10.0 g (41 mmol) of Example 40A are dissolved in anhydrous dichloromethane, and 13.6 g (89 mmol) of 1,8-diazabicyclo(5.4.0)undec-7-ene are added. At 25° C., 8.6 g (69 mmol) of 1-(chloromethoxy)-2-methoxyethane are added slowly, a little at a time, to this solution. After a further hour, the solution is filtered through silica gel and evaporated to dryness under reduced pressure. This gives 20.1 g (91% of theory) of the desired compound.

$^1$H-NMR (400 MHz, DMSO-d$_6$, δ/ppm): δ=8.32 (d, 1H), 8.19 (dd, 1H), 7.6 (d, 1H), 7.22 (dd, 1H), 7.15 (dd, 1H), 6.3 (t, 1H), 5.25 (s, 2H), 3.78-3.72 (m, 2H), 3.51-3.45 (m, 2H), 3.23 (s, 3H), 2.15 (s, 3H).

LC-MS (method 3): R$_t$=1.79 min
MS (ESIpos): m/z=335 (M+H)$^+$

Example 42A 1-(4-Amino-2-methylphenyl)-3-[(2-methoxyethoxy)methoxy]pyridin-2(1H)-one

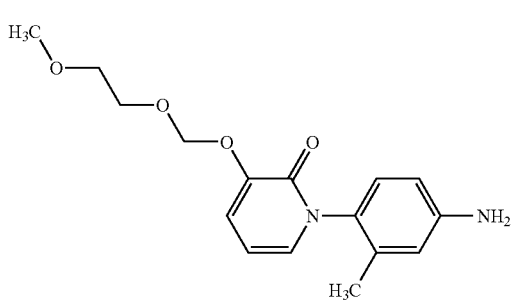 [SMILES: COCCOCOc1cccn(-c2ccc([N+](=O)[O-])cc2C)c1=O]

12 g (36 mmol) of Example 41A are dissolved in 1.2 l of a 1:1 mixture of ethyl acetate and ethanol, and 0.1 equivalent of palladium on carbon and 11.3 g (180 mmol) of ammonium formate are added. The mixture is heated at 80° C. for two hours. The mixture is allowed to cool and is filtered through silica gel, and the solvent is removed under reduced pressure. This gives 10.6 g (88% of theory) of the desired compound.

$^1$H-NMR (400 MHz, DMSO-$d_6$, δ/ppm): δ=7.12-7.05 (m, 1H), 6.80 (d, 1H), 6.51-6.42 (m, 2H), 6.17 (t, 1H), 5.21 (s, 2H), 3.76-3.71 (m, 2H), 3.49-3.45 (m, 2H), 3.23 (s, 3H), 1.85 (s, 3H).

LC-MS (method 3): $R_t$=1.10 min
MS (ESIpos): m/z=305 (M+H)$^+$

Example 43A

5-Chloro-N-[((5S)-3-{4-[3-[(2-methoxyethoxy)methoxy]-2-oxopyridin-1(2H)-yl]-3-methylphenyl}-2-oxo-1,3-oxazolidin-5-yl)methyl]thiophene-2-carboxamide

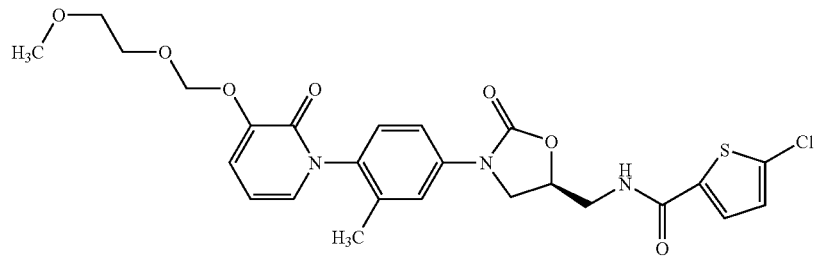 [SMILES: COCCOCOc1cccn(-c2ccc(N3C[C@H](CNC(=O)c4ccc(Cl)s4)OC3=O)cc2C)c1=O]

9.2 g (30 mmol) of Example 42A are dissolved in 580 ml of acetonitrile and cooled to 0° C. At this temperature, 7.3 g (34 mmol) of Example 1A are added, and the mixture is then stirred for a further 10 minutes. 10.2 g (46 mmol) of magnesium perchlorate are added, cooling is removed and the mixture is stirred for a further 17 h. 14.8 g (91 mmol) of carbonyldiimidazole and 0.37 g (3 mmol) of N,N-4-dimethylaminopyridine are then added, and the mixture is heated at 60° C. for 4 h. After cooling, the mixture is stirred at RT for a further 16 h and then evaporated to dryness under reduced pressure. 1N hydrochloric acid and ethyl acetate are added to the residue, and the mixture is stirred vigorously. After 15 min, the phases are separated, the aqueous phase is extracted three times with ethyl acetate and the organic phases are combined. After washing with saturated sodium chloride solution, the mixture is dried and evaporated to dryness under reduced pressure. This gives 17.2 g (95% of theory) of the desired compound.

$^1$H-NMR (400 MHz, DMSO-$d_6$, δ/ppm): δ=9.0 (t, 1H), 7.70 (d, 1H), 7.56-7.49 (m, 2H), 7.26 (d, 1H), 7.20 (d, 1H), 6.95 (dd, 1H), 6.80 (dd, 1H), 6.20 (t, 1H), 4.90-4.81 (m, 1H), 4.24 (t, 1H), 3.92-3.85 (m, 1H), 3.70-3.55 (m, 3H), 3.52-3.25 (m, 2H), 2.55 (s, 3H), 2.08-2.02 (m, 3H), 1.91 (s, 3H).

LC-MS (method 4): $R_t$=2.13 min
MS (ESIpos): m/z=548 (M+H)$^+$

Example 44A

5-Chloro-N-({(5S)-3-[4-(3-hydroxy-2-oxopyridin-1(2H)-yl)-3-methylphenyl]-2-oxo-1,3-oxazolidin-5-yl}methyl)thiophene-2-carboxamide

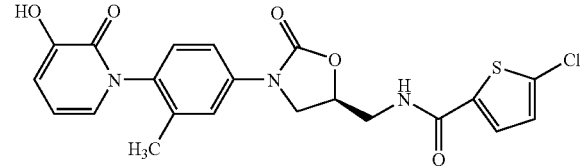 [SMILES: Cc1cc(N2C[C@H](CNC(=O)c3ccc(Cl)s3)OC2=O)ccc1-n1cccc(O)c1=O]

18 g (33 mmol) of Example 43A are dissolved in 50 ml of trifluoroacetic acid and stirred for 3 h, and the mixture is then evaporated to dryness under reduced pressure. The residue (22.3 g) is, in portions of 2 g each, dissolved in each case in 8.5 ml of dimethyl sulphoxide and purified by preparative HPLC using a water/acetonitrile gradient. The product fractions are combined and freed from acetonitrile, and the crystals formed are filtered off. The filtrate is extracted with ethyl acetate, and the ethyl acetate phases are combined, washed with saturated sodium chloride solution, dried and evaporated under reduced pressure. The residue is combined with the crystals and dried under reduced pressure. This gives 9.95 g (65% of theory) of the desired compound.

$^1$H-NMR (400 MHz, DMSO-$d_6$, δ/ppm): δ=9.2 (br. s, 1H), 9.00 (t, 1H), 7.70 (d, 1H), 7.56-7.48 (m, 2H), 7.26 (d, 1H), 7.20 (d, 1H), 6.95 (dd, 1H), 6.86 (dd, 1H), 6.2 (t, 1H), 4.92-4.80 (m, 1H), 4.22 (t, 1H), 3.92-3.82 (m, 1H), 3.62 (t, 2H), 2.04 (s, 3H).

LC-MS (method 4) $R_t$=2.09 min
MS (ESIpos): m/z=460 (M+H)$^+$

Example 45A

5-Chloro-N-[((5S)-3-{4-[3-(2-hydroxyethoxy)-2-oxopyridin-1(2H)-yl]-3-methylphenyl}-2-oxo-1,3-oxazolidin-5-yl)methyl]thiophene-2-carboxamide

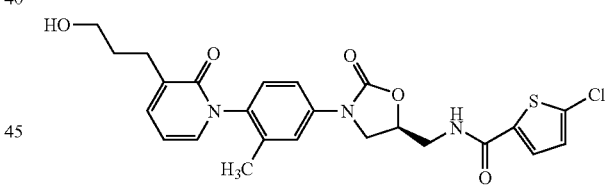

2.0 g (4.35 mmol) of Example 44A are dissolved in 9 ml of anhydrous N,N-dimethylformamide, 3.6 g (26.1 mmol) of potassium carbonate are added and the mixture is stirred for 30 min. The mixture is diluted with a further 3 ml of anhydrous N,N-dimethylformamide, 3.1 g (13.05 mmol) of (2-bromoethoxy)(tert-butyl)dimethylsilane are added and the mixture is heated at 60° C. for 7 h. The mixture is allowed to cool, filtered and purified by preparative HPLC using a water/acetonitrile gradient. The product fractions are evaporated to dryness under reduced pressure, and the residue is dried under reduced pressure. This gives 1.17 g (53% of theory) of the desired compound.

$^1$H-NMR (400 MHz, DMSO-$d_6$, δ/ppm): δ=9.00 (t, 1H), 7.70 (d, 1H), 7.55-7.48 (m, 2H), 7.25-7.18 (m, 2H), 7.05 (dd, 1H), 6.93 (dd, 1H), 6.22 (t, 1H), 4.91 (t, 1H), 4.89-4.82 (m, 1H), 4.22 (t, 1H), 4.00-3.85 (m, 3H), 3.75-3.70 (m, 2H), 3.61 (t, 2H), 2.0 (s, 3H).

LC-MS (method 5): $R_t$=1.93 min
MS (ESIpos): m/z=504 (M+H)$^+$

Example 46A

5-Chloro-N-{[(5S)-3-{4-[3-(2-chloroethoxy)-2-oxopyridin-1(2H)-yl]-3-methylphenyl}-2-oxo-1,3-oxazolidin-5-yl]methyl}thiophene-2-carboxamide

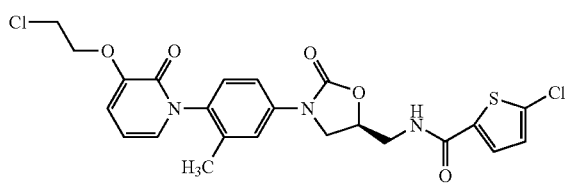 [SMILES: Cc1cc(N2C[C@H](CNC(=O)c3ccc(Cl)s3)OC2=O)ccc1-n1cccc(OCCCl)c1=O]

4.5 g (7.5 mmol) of Example 44A and 1.4 g (9.8 mmol) of 2-chloroethyl bromide are dissolved in 45 ml of absolute N,N-dimethylformamide, and 3.1 g (22.6 mmol) of potassium carbonate are added. The reaction is divided into three reaction vials and stirred at 80° C. in a microwave oven (300 W) for 40 minutes. In three portions, a total of 1.4 g (9.8 mmol) of 2-chloroethyl bromide is added to the cooled reaction vials, and the mixtures are stirred at 80° C. in a microwave oven (300 W) for a further 60 minutes. Water is added to the reaction, the mixture is extracted with dichloromethane and the separated organic phase is washed with 1N hydrochloric acid and saturated sodium chloride solution. The dichloromethane phase is dried over sodium sulphate, the drying agent is filtered off and the solvent is distilled off on a rotary evaporator. The residue is then chromatographed on silica gel 60 using the mobile phase dichloromethane/acetonitrile 10/1, rinsing with dichloromethane/methanol 10/1. The product-containing fraction is concentrated to dryness. Fine-purification by preparative RP-HPLC using an acetonitrile/water mixture gives 1.4 g of product (35% of theory).

$^1$H-NMR (400 MHz, DMSO-$d_6$, δ/ppm): 8.96 (t, 1H), 7.69 (d, 1H), 7.55-7.46 (m, 2H), 7.23 (d, 1H), 7.20 (d, 1H), 7.12 (d, 1H), 6.98 (d, 1H), 6.23 (t, 1H), 4.86 (m, 1H), 4.32-4.17 (m, 3H), 3.97 (m, 2H), 3.92-3.84 (m, 1H), 3.62 (t, 2H), 2.01 (s, 3H).

LC-MS (method 6): $R_t$=2.31 min, 2.36 min
MS (ESIpos): m/z=522 (M+H)$^+$

Example 47A (2-Fluoro-5-nitrobenzyl)(triphenyl)phosphonium bromide

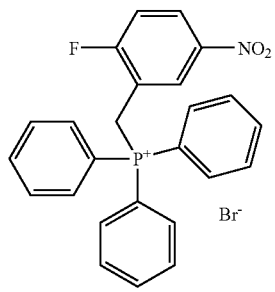 [SMILES: O=[N+]([O-])c1ccc(F)c(C[P+](c2ccccc2)(c2ccccc2)c2ccccc2)c1 ; [Br-]]

20 g (85.5 mmol) of the compound from Example 26A are dissolved in 250 ml of anhydrous toluene, and 22.4 g (85.5 mmol) of triphenylphosphine are added. The solution is heated under reflux for 16 h, resulting in the formation of a precipitate. The mixture is allowed to cool, and the precipitate is filtered off. After washing with diethyl ether, the precipitate is dried under reduced pressure. This gives 39 g (92% of theory) of the desired product.

$^1$H-NMR (400 MHz, DMSO-$d_6$, δ/ppm): δ=8.30-8.23 (m, 1H), 7.98-7.88 (m, 4H), 7.81-7.70 (m, 12H), 7.45 (t, 1H), 5.32 (d, 2H).

Example 48A

1-Fluoro-4-nitro-2-[prop-1-en-1-yl]benzene

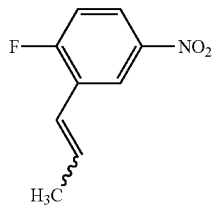

At 10° C., 5.99 g (32.7 mmol) sodium bis(trimethylsilyl)amide are added dropwise to a solution of 13.5 g (27.3 mmol) of the compound from Example 47A in 145 ml of dioxane. The mixture is stirred at this temperature for 1 h. A solution of 2.40 g (54.5 mmol) of acetaldehyde in 5 ml of dioxane is then added, and the reaction is stirred at RT for 1 h. 400 ml of water are then added, the mixture is extracted three times with dichloromethane and the combined organic phases are washed twice with saturated aqueous sodium chloride solution. After drying over sodium sulphate and subsequent filtration, the solvent is removed under reduced pressure. The product is purified by chromatography on silica gel (mobile phase: cyclohexane/ethyl acetate=40:1). This gives 5.2 g (100% of theory) of the desired product as an E/Z isomer mixture.

$^1$H-NMR (400 MHz, DMSO-$d_6$, δ/ppm): δ=8.47-8.05 (m, 2H), 7.58-7.42 (m, 1H), 6.70-6.05 (m, 2H), 1.90-1.78 (m, 3H).

GC-MS (method 10): $R_t$=2.64 and 2.70 min
MS (ESIpos): m/z=181 (M+H$^+$)$^+$

Example 49A

3-Methoxy-1-{4-nitro-2-[prop-1-en-1-yl]phenyl}pyridin-2(1H)-one

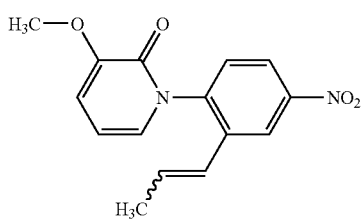

14.0 g (111.9 mmol) of 3-methoxypyridin-2(1H)-one are dissolved in 350 ml of dimethyl sulphoxide, 15.4 g (134.3 mmol) of potassium tert-butoxide are added and the suspension is stirred at room temperature for 30 minutes. 20.2 g (111.9 mmol) of Example 48A are added to the reaction mixture. The mixture is heated to 80° C. and stirred at this temperature for 12 hours. Using 150 ml of 1N hydrochloric acid and slight cooling, the reaction is adjusted to pH 3, the mixture is diluted with 800 ml of water and extracted with dichloromethane and the organic phase is washed successively with water and saturated sodium chloride solution. The dichloromethane phase is then dried over sodium sulphate, the drying agent is filtered off and the solvent is removed completely on a rotary evaporator. The residue gives, after recrystllization with tert-butyl methyl ether, 17.9 g of product (45% of theory).

¹H-NMR (400 MHz, DMSO-d₆, δ/ppm): 8.50 (d, 0.75H), 8.17 (dd, 0.25H), 8.22-8.13 (m, 1H), 7.17 (d, 0.25H), 7.57 (d, 0.75H), 7.09 (dd, 1H), 6.96 (dd, 0.75H) 6.91 (d, 0.25H), 6.59 (m, 0.75H), 6.35-6.23 (m, 1H), 6.09-5.85 (m, 1.25H), 3.78 (s, 2.25H), 3.75 (s, 0.75H), 1.81 (dd, 2.25H), 1.73 (dd, 0.75H).

LC-MS (method 3): $R_t$=2.75 min, 2.79 min
MS (ESIpos): m/z=273 (M+H)⁺

Example 50A

3-Hydroxy-1-{4-nitro-2-[prop-1-en-1-yl]phenyl}pyridin-2(1H)-one

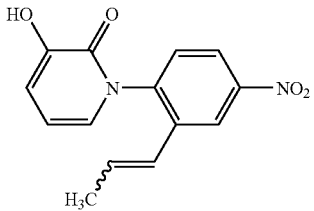

17.8 g (50.6 mmol) of Example 49A are dissolved in 300 ml of dichloromethane. 31.7 g (126.5 mmol) of boron tribromide, dissolved in 100 ml of dichloromethane, are added dropwise to the ice-cooled solution, and the mixture is stirred at 0° C. for 1.5 hours. Ice is added to the stirred reaction. The mixture is then diluted with water and subsequently extracted repeatedly with dichloromethane/methanol 10/1 and chloroform. The combined organic phases are dried over sodium sulphate, the drying agent is filtered off and the solvent is distilled off on a rotary evaporator. The residue gives, after recrystallization with tert-butyl methyl ether/dichloromethane (10/1), 9.4 g of product (67% of theory).

¹H-NMR (400 MHz, DMSO-d₆, δ/ppm): 9.43 (br. s, 1H), 8.50 (d, 0.75H), 8.27 (dd, 0.25H), 8.22-8.13 (m, 1H), 7.19 (d, 0.25H), 7.59 (d, 0.75H), 6.99 (dd, 1H), 6.85 (d, 0.75H) 6.81 (d, 0.25H), 6.58 (m, 0.75H), 6.31-6.19 (m, 1H), 6.11-5.85 (m, 1.25H), 1.81 (dd, 2.25H), 1.73 (dd, 0.75H).

LC-MS (method 3): $R_t$=1.78 min
MS (ESIpos): m/z=287 (M+H)⁺

Example 51A

3-[(2-Methoxyethoxy)methyl]-1-{4-nitro-2-[prop-1-en-1-yl]phenyl}pyridin-2(1H)-one

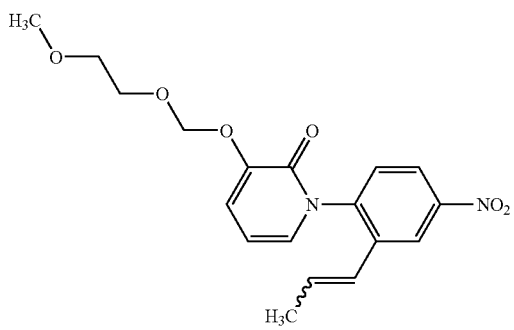

15.0 g (48.9 mmol) of Example 50A are dissolved in 700 ml of dichloromethane, and 16.4 g (107 mmol) of 1,8-diazabicyclo[5.4.0]undec-7-ene are added. A solution of 100 ml of dichloromethane and 10.4 g (83.2 mmol) of 1-(chloromethoxy)-2-methoxyethane is added dropwise to the water-cooled mixture, and the mixture is stirred at room temperature for 4 hours. For work-up, the reaction solution is applied directly to silica gel 60 and chromatographed using a mobile phase gradient of cyclohexane and ethyl acetate (2/1→1/2). This gives 9.6 g (43% of theory) of product.

¹H-NMR (400 MHz, DMSO-d₆, δ/ppm): 8.50 (d, 0.5H), 8.27 (dd, 0.5H), 8.22-8.13 (m, 1H), 7.19 (d, 0.5H), 7.59 (d, 0.5H), 7.23-7.10 (m, 2H), 6.58 (m, 0.5H) 6.85-6.25 (m, 1H), 6.60-5.85 (m, 1.5H), 5.28 (s, 1H), 5.23 (s, 1H), 3.75 (m, 2H), 3.48 (m, 2H), 3.25 (s, 3H), 1.80 (dd, 1.5H), 1.72 (dd, 1.5H).

LC-MS (method 6): $R_t$=2.09 min
MS (ESIpos): m/z=361 (M+H)⁺

Example 52A 1-(4-Amino-2-propylphenyl)-3-[(2-methoxyethoxy)methoxy]pyridin-2(1H)-one

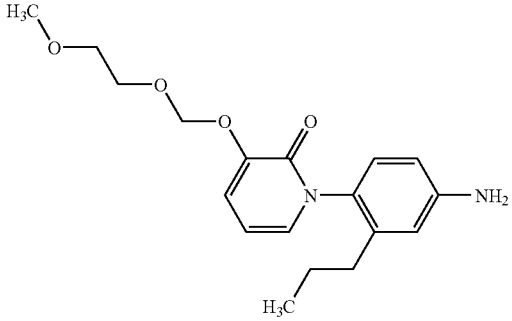 [SMILES: CCCc1cc(N)ccc1-n1cccc(OCOCCOC)c1=O]

2.9 g (7.0 mmol) of Example 51A are dissolved in a mixture of 56 ml of ethyl acetate and 35 ml of ethanol, and 2.2 g (35.0 mmol) of ammonium formate and a catalytic amount of 10% palladium on carbon are added successively. The reaction is stirred at 80° C. for 2 hours. For work-up, the cooled suspension is filtered through silica gel 60, the filter cake is washed with ethanol and the filtrate is concentrated to dryness on a rotary evaporator. The residue is dissolved in a mixture of 56 ml of ethyl acetate and 35 ml of ethanol, and 2.2 g (35.0 mmol) of ammonium formate and a catalytic amount of 10% palladium on carbon are added. After a reaction time of 24 hours and at a temperature of 80° C., the starting material is reduced completely. The cooled suspension is again filtered through silica gel 60 eluting with ethanol, and the solvent is removed completely on a rotary evaporator. This gives 3.0 g of crude product.

LC-MS (method 6): $R_t$=1.73 min, 1.81 min
MS (ESIpos): m/z=333 (M+H)⁺

Example 53A

5-Chloro-N-({(5S)-3-[4-(3-hydroxy-2-oxopyridin-1(2H)-yl)-3-propylphenyl]-2-oxo-1,3-oxazolidin-5-yl}methyl)thiophene-2-carboxamide

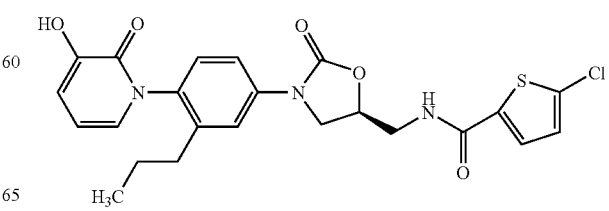

3.0 g (9.0 mmol) of Example 52A are dissolved in 125 ml of acetonitrile. 2.6 g (9.9 mmol) of Example 1A are added to the ice-cooled solution, the mixture is stirred for 10 min and 3.0 g (13.5 mmol) of magnesium perchlorate are then added a little at a time. The mixture is stirred at room temperature overnight, and 4.4 g (27.1 mmol) of 1,1-carbonyl diimidazole and 0.1 g (0.9 mmol) of 4-dimethylaminopyridine are then added. After 4 hours at 60° C., the suspension is filtered, the filter residue is washed with acetonitrile and the filtrate is concentrated to dryness on a rotary evaporator. The residue is taken up in ethyl acetate and extracted with 50 ml of 1N hydrochloric acid, the aqueous acidic phase is extracted repeatedly with ethyl acetate and the combined organic phases are washed with saturated sodium chloride solution. The ethyl acetate phase is then dried over sodium sulphate, the drying agent is filtered off and the solvent is removed completely on a rotary evaporator. Fine-purification by preparative RP-HPLC using an acetonitrile/water mixture gives 1.1 g (19% of theory) of product.

LC-MS (method 11): $R_t$=3.26 min
MS (ESIpos): m/z=488 (M+H)$^+$

Example 54A

5-Chloro-N-{[(5S)-3-{4-[3-(2-chloroethoxy)-2-oxopyridin-1(2H)-yl]-3-propylphenyl}-2-oxo-1,3-oxazolidin-5-yl]methyl}thiophene-2-carboxamide

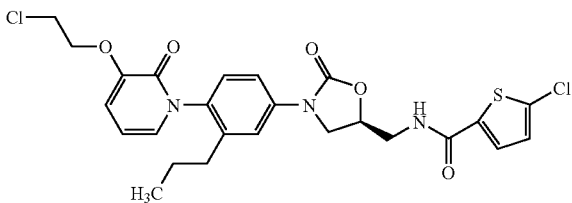 [SMILES: CCCc1cc(N2C[C@H](CNC(=O)c3ccc(Cl)s3)OC2=O)ccc1-n1cccc(OCCCl)c1=O]

241 mg (0.50 mmol) of Example 53A and 270 mg (1.4 mmol) of 1-chloro-2-iodoethane are dissolved in 9 ml of N,N-dimethylformamide, and 131 mg (0.90 mmol) of potassium carbonate are added. The reaction is stirred at 60° C. for 4 hours. For work-up, water is added to the suspension, and the mixture is extracted with dichloromethane. The separated organic phase is washed successively with 1N hydrochloric acid and saturated sodium chloride solution and then dried over sodium chloride, the drying agent is filtered off and the solvent is removed completely on a rotary evaporator. Drying of the residue under reduced pressure gives 30 mg (12% of theory) of the product.

LC-MS (method 6): $R_t$=2.36 min
MS (ESIpos): m/z=550 (M+H)$^+$

Example 55A 1-(4-Amino-2-propylphenyl)-3-methoxypyridin-2(1H)-one

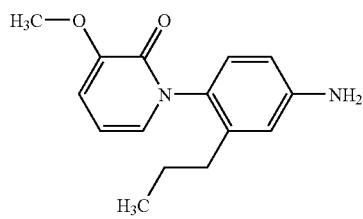 [SMILES: CCCc1cc(N)ccc1-n1cccc(OC)c1=O]

27.0 g (87.7 mmol) of Example 49A are dissolved in 702 ml of ethyl acetate and 441 ml of ethanol, 16.6 g (263 mmol) of ammonium formate and 0.093 g (0.09 mmol) of palladium/carbon (10%) are added and the mixture is stirred at 80° C. for 16 h. Because of incomplete conversion, 5.5 g (87 mmol) of ammonium formate and 0.03 g (0.03 mmol) of palladium/carbon (10%) are added. After a further 16 h of stirring at 80° C., the same amounts are added, and the mixture is stirred at 80° C. for 16 h. For work-up, the reaction solution is brought to room temperature and passed through a silica gel frit. The filter cake is washed with ethanol, the filtrate is concentrated under reduced pressure and the residue is chromatographed on silica gel 60 using a gradient of dichloromethane and methanol (100/1→30/1). This gives 17.3 g of product; however, the $^1$H-NMR spectrum of this product still contains signals for the intermediate, which contains a double bond. Accordingly, the impure material is dissolved in 360 ml of ethyl acetate and 226 ml of ethanol, 12.8 g (202 mmol) of ammonium formate and 0.072 g (0.07 mmol) of palladium/carbon (10%) are added, and the mixture is stirred at 80° C. for 36 h. After cooling, the mixture is filtered through a silica gel frit, the filter cake is washed with ethanol and the filtrate is concentrated under reduced pressure. The residue is chromatographed on silica gel 60 using a gradient of dichloromethane and methanol (100/1→10/1). This gives 8.35 g of product (47% of theory).

$^1$H-NMR (400 MHz, DMSO-d$_6$, δ/ppm): 6.97 (dd, 1H), 6.85 (dd, 1H), 6.75 (d, 1H), 6.50 (d, 1H), 6.45 (dd, 1H), 6.15 (t, 1H), 5.22 (s, 2H) 3.71 (s, 3H), 2.12 (t, 2H), 1.45-1.30 (m, 2H), 0.76 (t, 3H).

LC-MS (method 6): $R_t$=1.53 min
MS (ESIpos): m/z=259 (M+H)$^+$.

Example 56A

5-Chloro-N-({(5S)-3-[4-(3-methoxy-2-oxopyridin-1(2H)-yl)-3-propyl phenyl]-2-oxo-1,3-oxazolidin-5-yl}methyl)thiophene-2-carboxamide

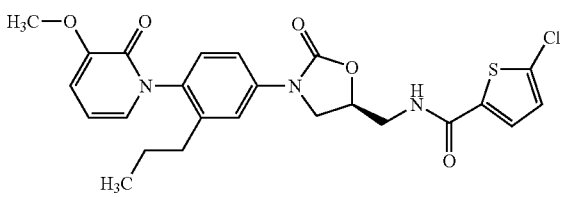 [SMILES: CCCc1cc(N2C[C@H](CNC(=O)c3ccc(Cl)s3)OC2=O)ccc1-n1cccc(OC)c1=O]

1.00 g (3.87 mmol) of Example 55A is dissolved in 23.5 ml of anhydrous acetonitrile, and 926 mg (4.26 mmol) of Example 1A and 1.30 g (5.81 mmol) of magnesium perchlorate are added. The mixture is stirred at room temperature for 3.5 h. 1.57 g (9.68 mmol) of carbonyldiimidazole and 47 mg (0.38 mmol) of 4-dimethylaminopyridine are then added, and the mixture is stirred at 60° C. for 4 h and then at RT for 18 h. The mixture is then diluted with 300 ml of water and 150 ml of ethyl acetate, and the aqueous phase is extracted twice with 150 ml of ethyl acetate. The combined organic phases are dried over sodium sulphate and concentrated under reduced pressure, and the residue obtained is purified by chromatography on silica gel (dichloromethane/methanol 20:1). This gives 1.81 g (92% of theory) of the desired product.

$^1$H-NMR (400 MHz, DMSO-d$_6$, δ/ppm): δ=8.99 (t, 1H), 7.70 (d, 1H), 7.58-7.47 (m, 2H), 7.26-7.15 (m, 2H), 7.04 (dd, 1H), 6.90 (dd, 1H), 6.23 (dd, 1H), 4.91-4.81 (m, 1H), 4.23

(dd, 1H), 3.93-3.85 (m, 1H), 3.74 (s, 3H), 3.62 (dd, 2H), 2.31-2.23 (m, 2H), 1.50-1.36 (m, 2H), 0.78 (t, 3H).
HPLC (method 2): R$_t$=4.19 min
MS (ESI pos, m/z)=502 (M+H)$^+$ Example 57A 5-Chloro-N-({(5S)-3-[4-(3-hydroxy-2-oxopyridin-1(2H)-yl)-3-propyl phenyl]-2-oxo-1,3-oxazolidin-5-yl}methyl)thiophene-2-carboxamide

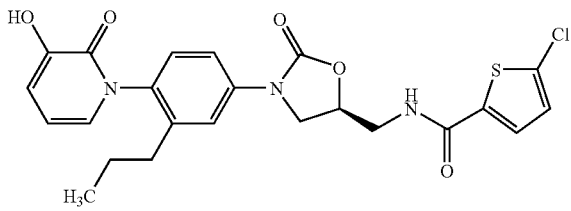

1.79 g (3.56 mmol) of Example 56A are dissolved in 104 ml of anhydrous dichloromethane and cooled to −78° C. At this temperature, 28.5 ml (28.5 mmol) of a 1N boron tribromide solution in dichloromethane are added such that the temperature does not exceed −65° C. The mixture is stirred at −78° C. for 2 h and then at RT for 1 h and then carefully added to 200 ml of saturated aqueous sodium bicarbonate solution. After phase separation, the aqueous phase is extracted three times with dichloromethane, and the combined organic phases are washed with saturated sodium chloride solution, dried over sodium sulphate, filtered and evaporated to dryness under reduced pressure. This gives 1.75 g (97% of theory) of the desired compound.
$^1$H-NMR (400 MHz, DMSO-d$_6$, δ/ppm): δ=9.21 (s, 1H), 8.99 (t, 1H), 7.70 (d, 1H), 7.56-7.47 (m, 2H), 7.29-7.15 (m, 2H), 6.94 (dd, 1H), 6.80 (dd, 1H), 6.19 (dd, 1H), 4.91-4.81 (m, 1H), 4.23 (dd, 1H), 3.93-3.85 (m, 1H), 3.62 (dd, 2H), 2.35-2.26 (m, 2H), 1.50-1.36 (m, 2H), 0.78 (t, 3H).
HPLC (method 2): R$_t$=4.21 min
MS (DCI): m/z=488 (M+H)$^+$ Example 58A 5-Chloro-N-{[(5S)-3-{4-[3-(2-chloroethoxy)-2-oxopyridin-1(2H)-yl]-3-propylphenyl}-2-oxo-1,3-oxazolidin-5-yl]methyl}thiophene-2-carboxamide

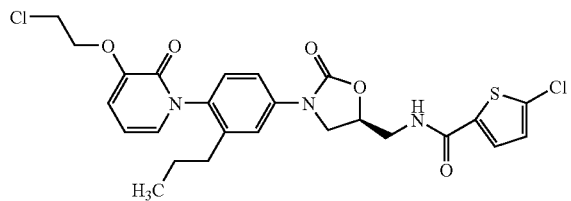 [SMILES: CCCc1cc(N2C[C@H](CNC(=O)c3ccc(Cl)s3)OC2=O)ccc1-n1cccc(OCCCl)c1=O]

1.70 g (3.48 mmol) of Example 57A and 2.49 g (17.4 mmol) of 1-bromo-2-chloroethane are dissolved in 55 ml of 1-methyl-2-pyrrolidone. 2.27 g (6.96 mmol) of caesium carbonate are added to the solution, and the mixture is stirred at 60° C. for 2 hours. 500 ml of water, 100 ml of saturated aqueous sodium chloride solution and 200 ml of tert-butyl methyl ether and 200 ml of ethyl acetate are then added. After phase separation, the aqueous phase is extracted twice with 200 ml of ethyl acetate. The combined organic phases are washed successively with 1N sodium hydroxide solution and saturated sodium chloride solution and then dried over sodium sulphate, the drying agent is filtered off and the solvent is removed completely on a rotary evaporator. The residue is purified by chromatography on silica gel (dichloromethane/ethanol 40:1). This gives 1.78 g (85% of theory) of the desired product.
$^1$H-NMR (400 MHz, DMSO-d$_6$, δ/ppm): δ=8.99 (t, 1H), 7.70 (d, 1H), 7.56-7.47 (m, 2H), 7.29-7.13 (m, 2H), 7.12 (dd, 1H), 6.99 (dd, 1H), 6.22 (dd, 1H), 4.91-4.82 (m, 1H), 4.30-4.14 (m, 1H), 3.98-3.85 (m, 1H), 3.61 (dd, 2H), 2.35-2.26 (m, 2H), 2.18 (t, 2H), 1.95-1.85 (m, 2H), 1.50-1.36 (m, 2H), 0.78 (t, 3H).
HPLC (method 2): R$_t$=4.44 min
MS (ESIpos): m/z=550 (M+H)$^+$ Example 59A 3-Bromo-1-(2,6-dimethyl-4-nitrophenyl)pyridin-2(1H)-one

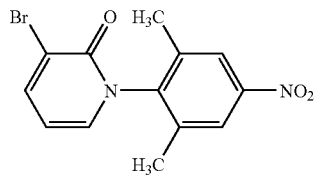

2.81 g (16.1 mmol) of 3-bromopyridin-2(1H)-one (O. S. Tee, M. Pavent, J. Am. Chem. Soc. 1982, 104, 4142-4146.) are dissolved in 100 ml of DMF. The mixture is cooled to 0° C., and 2.71 g (24.2 mmol) of potassium tert-butoxide are added. The ice bath is removed, and the mixture is stirred at room temperature for 30 min. 3.00 g (17.7 mmol) of 1-fluoro-2,5-dimethyl-4-nitrobenzene are added, and the mixture is stirred at 80° C. for 18 h, at 100° C. for 36 h and at 120° C. for 18 h. The mixture is then added to water and extracted three times with ethyl acetate. The combined organic phases are dried over sodium sulphate. The residue is purified by chromatography on silica gel (cyclohexane/ethyl acetate 4:1). This gives 2.04 g (38% of theory) of the desired compound.
$^1$H-NMR (400 MHz, DMSO-d$_6$, δ/ppm): δ=8.19 (s, 2H), 8.14 (dd, 1H), 7.62 (dd, 1H), 6.43 (t, 1H), 2.11 (s, 6H).
HPLC (method 1): R$_t$=4.13 min.
MS (ESIpos, m/z): 323 (M+H)$^+$.
Alternative Synthesis:
150 g (750 mmol) of 3-bromopyridin-2(1H)-one (O. S. Tee, M. Pavent, J. Am. Chem. Soc. 1982, 104, 4142-4146.) and 207 g (1.50 mol) of potassium carbonate are dissolved in 2.9 l of dimethyl sulphoxide and heated to 120° C. At this temperature, a solution of 317 g (750 mmol) of 1-fluoro-2,5-dimethyl-4-nitrobenzene in 700 ml of dimethyl sulphoxide is added dropwise over a period of 60 min, and the mixture is stirred at 120° C. for 3.5 h. After cooling, the reaction solution is stirred into a water/hydrochloric acid mixture. The mixture is extracted with ethyl acetate, the phases are separated and the aqueous phase is once more extracted with ethyl acetate. The combined organic phases are then washed with water. The phases are separated, and the organic phase is dried over sodium sulphate. After concentration under reduced pressure, the residue is purified by chromatography on silica gel (dichloromethane, then ethyl acetate/dichloromethane 1:20). The product-containing fractions are combined, the solvents are removed and the residue is triturated with diethyl ether. This gives 112 g (46% of theory) of the desired compound.

$^1$H-NMR (400 MHz, DMSO-d$_6$, δ/ppm): δ=8.19 (s, 2H), 8.14 (dd, 1H), 7.62 (dd, 1H), 6.43 (t, 1H), 2.11 (s, 6H).

HPLC (method 13): R$_t$=1.59 min.

MS (ESIpos, m/z): 323 (M+H)$^+$.

Example 60A 1-(2,6-Dimethyl-4-nitrophenyl)-3-vinylpyridin-2(1H)-one

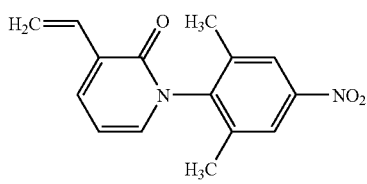 [SMILES: C=Cc1cccn(-c2c(C)cc([N+](=O)[O-])cc2C)c1=O]

2.00 g (6.19 mmol) of the compound from Example 59A are dissolved in 31 ml of anhydrous dioxane, and 2.36 g (7.42 mmol) of tributylvinyltin and 143 mg (0.124 mmol) of tetrakis(triphenylphosphine)palladium are added and the mixture is stirred at 100° C. for 5 h. The mixture is allowed to cool and filtered through kieselguhr. The filter cake is washed three times with ethyl acetate, and the combined filtrates are concentrated to dryness under reduced pressure. The residue is purified by chromatography on silica gel (cyclohexane/ethyl acetate 4:1). This gives 846 mg (51% of theory) of the desired product.

$^1$H-NMR (400 MHz, DMSO-d$_6$, δ/ppm): δ=8.17 (s, 2H), 7.78 (dd, 1H), 7.48 (dd, 1H), 6.75 (dd, 1H), 6.48 (dd, 1H), 6.14 (dd, 1H), 5.33 (dd, 1H), 2.10 (s, 6H).

HPLC (method 1): R$_t$=4.25 min

MS (ESIpos): m/z=271 (M+H)$^+$

Alternative Synthesis:

132 g (408 mmol) of the compound from Example 59A (alternative synthesis) are dissolved in 1.27 l of anhydrous dioxane, 136 g (428 mmol) of tributylvinyltin and 9.44 g (8.17 mmol) of tetrakis(triphenylphosphine)palladium are added and the mixture is stirred at 100° C. for 4 h. The mixture is allowed to cool and filtered through kieselguhr. The mixture is concentrated to dryness under reduced pressure. The residue is dissolved in dichloromethane and purified by chromatography on silica gel (petroleum ether/ethyl acetate 9:1, then 8:2, then 7:3). The product-containing fractions are combined, the solvents are removed and the residue is triturated with petroleum ether/diethyl ether (10:1). This gives 83 g (75% of theory) of the desired product.

$^1$H-NMR (400 MHz, DMSO-d$_6$, δ/ppm): δ=8.17 (s, 2H), 7.78 (dd, 1H), 7.48 (dd, 1H), 6.75 (dd, 1H), 6.48 (dd, 1H), 6.14 (dd, 1H), 5.33 (dd, 1H), 2.10 (s, 6H).

HPLC (method 13): R$_t$=1.70 min

MS (ESIpos): m/z=271 (M+H)$^+$

Example 61A 1-(2,6-Dimethyl-4-nitrophenyl)-3-(2-hydroxyethyl)pyridin-2(1H)-one

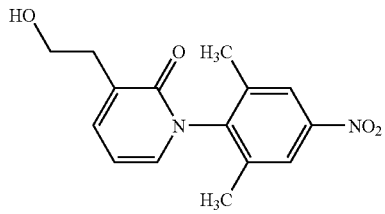 [SMILES: Cc1cc([N+](=O)[O-])cc(C)c1-n1cccc(CCO)c1=O]

With ice-cooling, a solution of 902 mg (7.40 mmol) of 9-borabicyclo[3.3.1]nonane in 14.8 ml tetrahydrofuran is added to 800 mg (2.96 mmol) of the compound from Example 60A. The mixture is stirred at room temperature for 3 h and then cooled to 0° C., and an aqueous solution of 591 mg (14.8 mmol) of sodium hydroxide is added over a period of 15 min. 2.60 ml of a 30% strength hydrogen peroxide solution are added such that the temperature does not exceed 30° C. After the addition has ended, the mixture is stirred at 0° C. for 30 min. With ice-cooling, a solution of 8.73 g (32.6 mol) of sodium bisulphite in 12 ml of water is added to the reaction mixture. The mixture is diluted with 50 ml of ethyl acetate, the organic phase is removed and the aqueous phase is extracted twice with ethyl acetate. The combined organic phases are washed with saturated sodium chloride solution, dried over sodium sulphate and evaporated to dryness under reduced pressure. The residue is purified by chromatography on silica gel (cyclohexane/ethyl acetate 1:2). This gives 765 mg (89% of theory) of the desired product.

$^1$H-NMR (400 MHz, DMSO-d$_6$, δ/ppm): δ=8.15 (s, 2H), 7.46 (dd, 1H), 7.35 (dd, 1H), 6.37 (dd, 1H), 4.62 (dd, 1H), 4.25 (d, 1H), 2.62 (dd, 2H), 2.08 (s, 6H).

HPLC (method 1): R$_t$=3.59 min

MS (ESIpos): m/z=289 (M+H)$^+$

Alternative Synthesis:

With ice-cooling, 1.15 l (575 mmol) of a 0.5 molar solution of 9-borabicyclo[3.3.1]nonane in tetrahydrofuran are added to 70.7 g (262 mmol) of the compound from Example 60A (alternative synthesis) such that the internal temperature does not exceed 10-15° C. The mixture is then warmed to RT and stirred at room temperature for 1.5 h. The mixture is then cooled and, at 0° C.-5° C., 653 ml (1.31 mol) of a 2-molar aqueous solution of sodium hydroxide are added. The mixture is stirred briefly, and 296 g (2.51 mol) of a 30% strength hydrogen peroxide solution are then added such that the temperature does not exceed 30° C. and does not fall below 25° C. After the addition has ended, the mixture is stirred for another 30 min. Water and ethyl acetate are added to the reaction mixture. After phase separation, the aqueous phase is once more extracted with ethyl acetate. The combined organic phases are washed with an aqueous sodium bisulphite solution. The organic phase is removed and evaporated to dryness under reduced pressure. The residue is dissolved in dichloromethane and purified by chromatography on silica gel (cyclohexane/ethyl acetate 1:2, then ethyl acetate). This gives 66.5 g (88% of theory) of the desired product.

$^1$H-NMR (400 MHz, CDCl$_3$, S/ppm): δ=8.07 (s, 2H), 7.43 (dd, 1H), 6.98 (ddd, 1H), 6.38 (dd, 1H), 3.88 (ddd, 2H), 3.55 (dd, 1H), 2.89 (dd, 2H), 2.19 (s, 6H).

HPLC (method 14): R$_t$=0.83 min

MS (ESIpos): m/z=289 (M+H)$^+$

Example 62A 3-(2-{[tert-Butyl(diphenyl)silyl]oxy}ethyl)-1-(2,6-dimethyl-4-nitrophenyl)pyridin-2(1H)-one

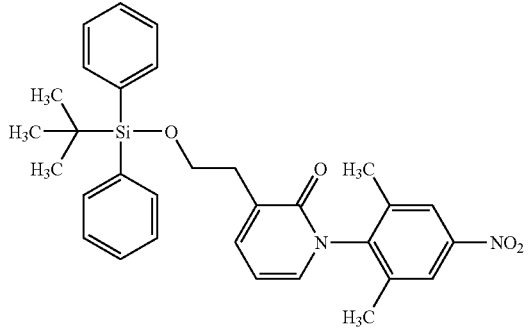 [SMILES: Cc1cc([N+](=O)[O-])cc(C)c1-n1cccc(CCO[Si](c2ccccc2)(c2ccccc2)C(C)(C)C)c1=O]

760 mg (2.64 mmol) of the compound from Example 61A and 0.55 ml (3.9 mmol) of triethylamine are dissolved in 7 ml of anhydrous N,N-dimethylformamide. 16 mg (0.13 mmol) of 4-dimethylaminopyridine and 1.09 g (3.95 mmol) of tert-butyl(chloro)diphenylsilane are added, and the mixture is stirred at RT for 2 h. The mixture is then added to water and, after phase separation, extracted three times with ethyl acetate. The combined organic phases are washed twice with water, dried over sodium sulphate, filtered, and evaporated under reduced pressure. The residue is purified by chromatography on silica gel (cyclohexane/ethyl acetate 5:1). This gives 971 mg (58% of theory) of the desired product.

HPLC (method 2): $R_t$=5.97 min
MS (ESIpos): m/z=527 (M+H)$^+$

Alternative Synthesis:

100 g (346 mmol) of the compound from Example 61A (alternative synthesis) and 30.7 g (450 mmol) of imidazole are dissolved in 1 l of anhydrous N,N-dimethylformamide. A solution of 117 g (416 mmol) of tert-butyl(chloro)diphenylsilane in 150 ml of N,N-dimethylformamide is added dropwise, and the mixture is stirred at RT for 3 h. Water and ethyl acetate are then added, the phases are separated and the organic phase is washed with water, dried over sodium sulphate, filtered and evaporated under reduced pressure. The residue is triturated with petroleum ether/diethyl ether (10:1). After filtration, the residue is washed with petroleum ether and then air-dried. This gives 150 g (82% of theory) of the desired product.

$^1$H-NMR (400 MHz, CDCl$_3$, S/ppm): δ=8.04 (s, 2H), 7.68-7.62 (m, 4H), 7.46-7.33 (m, 7H), 6.92 (dd, 1H), 6.30 (dd, 1H), 3.95 (dd, 2H), 2.86 (dd, 2H), 2.16 (s, 6H), 1.02 (s, 9H).

HPLC (method 13): $R_t$=2.98 min
MS (ESIpos): m/z=527 (M+H)$^+$

Example 63A 1-(4-Amino-2,6-dimethylphenyl)-3-(2-{[tert-butyl(diphenyl)silyl]oxy}ethyl)pyridin-2(1H)-one

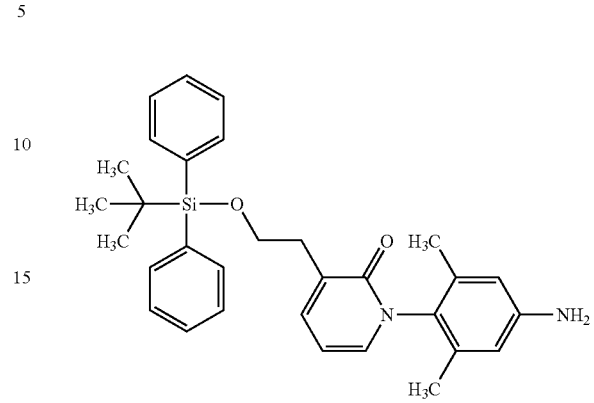

970 mg (1.84 mmol) of the compound from Example 62A are dissolved in 20 ml of THF. 200 mg of palladium on carbon are then added, and the mixture is hydrogenated at RT in a hydrogen atmosphere under atmospheric pressure. The mixture is then filtered through kieselguhr, the filter cake is washed three times with THF and the filtrate is freed from the solvent. The reaction product (1.00 g) is reacted further without further purification.

HPLC (method 2): $R_t$=4.99 min
MS (ESIpos): m/z=497 (M+H)$^+$

Alternative Synthesis:

143 g (271 mmol) of the compound from Example 62A (alternative synthesis) are dissolved in 1.43 l of tetrahydrofuran and flushed with argon. 17 g of palladium on carbon (50%, moistened with water) are added, and the mixture is then hydrogenated at RT in a hydrogen atmosphere under atmospheric pressure. The mixture is then filtered through kieselguhr, the filter cake is washed with tetrahydrofuran and the filtrate is freed from the solvent. The reaction product (134 g) is reacted further without further purification.

HPLC (method 6): $R_t$=3.11 min
MS (ESIpos): m/z=497 (M+H)$^+$

Example 64A

N-[((5S)-3-{4-[3-(2-{[tert-Butyl(diphenyl)silyl]oxy}ethyl)-2-oxopyridin-1(2H)-yl]-3,5-dimethylphenyl}-2-oxo-1,3-oxazolidin-5-yl)methyl]-5-chlorothiophene-2-carboxamide

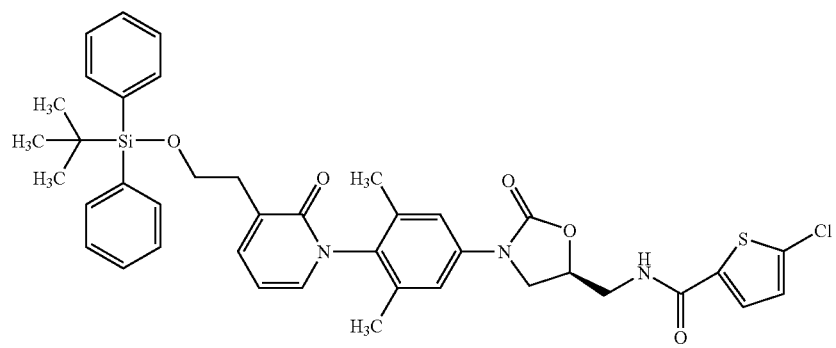 [SMILES: Cc1cc(N2C[C@H](CNC(=O)c3ccc(Cl)s3)OC2=O)cc(C)c1-n1cccc(CCO[Si](c2ccccc2)(c2ccccc2)C(C)(C)C)c1=O]

800 mg (1.61 mmol) of the compound from Example 63A are dissolved in 15 ml of anhydrous acetonitrile, and 385 g (1.77 mmol) of the compound from Example 1A and 539 mg (2.41 mmol) of magnesium perchlorate are added. The mixture is stirred at room temperature for 5.5 h. 652 mg (4.03 mmol) of 1,1-carbonyldiimidazole and 19 mg (0.16 mmol) of N,N-dimethylaminopyridine are then added, and the mixture is heated at reflux for 18 h. The mixture is allowed to cool and added to 100 ml of water and 100 ml of ethyl acetate. After phase separation, the aqueous phase is extracted twice with ethyl acetate and the combined organic phases are dried over sodium sulphate. After filtration, the mixture is evaporated to dryness under reduced pressure. The residue is purified by chromatography on silica gel (cyclohexane/ethyl acetate 1:2). This gives 664 mg (55% of theory) of the desired product.

$^1$H-NMR (400 MHz, DMSO-$d_6$, δ/ppm): δ=8.99 (t, 1H), 7.70 (d, 1H), 7.63-7.45 (m, 4H), 7.48-7.31 (m, 9H), 7.28 (dd, 1H), 7.20 (d, 1H), 6.32 (t, 1H), 4.90-4.81 (m, 1H), 4.22 (dd, 1H), 3.89-3.82 (m, 3H), 3.62 (t, 2H), 2.76 (dd, 2H), 1.94 (s, 6H), 0.95 (s, 9H).

HPLC (method 2): $R_t$=5.92 min
MS (ESIpos): m/z=740 (M+H)$^+$

Alternative Synthesis:

102 g (171 mmol) of the compound from Example 68A are dissolved in 1.45 l of dichloromethane, and 44.7 ml (257 mmol) of N,N-diisopropylethylamine are added. A solution of 37.1 g (205 mmol) of 5-chlorothiophene-2-carbonyl chloride in a little dichloromethane is slowly added dropwise, and the mixture is stirred at room temperature for one hour. Water is then added, the phases are separated and the organic phase is dried over sodium sulphate. After filtration, the filtrate is evaporated to dryness under reduced pressure. The residue is reacted further without further purification.

HPLC (method 6): $R_t$=3.33 min
MS (ESIpos): m/z=740 (M+H)$^+$

Example 65A

5-Chloro-N-[((5S)-3-{4-[3-(2-hydroxyethyl)-2-oxopyridin-1(2H)-yl]-3,5-dimethylphenyl}-2-oxo-1,3-oxazolidin-5-yl)methyl]thiophene-2-carboxamide

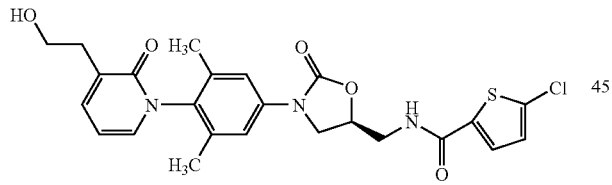

660 mg (0.891 mmol) of the compound from Example 64A are dissolved in 20 ml of THF, and 512 mg (1.96 mmol) of tetrabutylammonium fluoride are added. After 1 h, the mixture is concentrated to dryness under reduced pressure. The residue is purified by chromatography on silica gel (dichloromethane/methanol 10:1; 1% triethylamine). This gives 396 mg (85% of theory) of the desired product.

$^1$H-NMR (400 MHz, DMSO-$d_6$, δ/ppm): δ=8.98 (t, 1H), 7.69 (d, 1H), 7.42 (dd, 1H), 7.38 (d, 1H), 7.25 (dd, 1H), 7.19 (d, 1H), 6.29 (t, 1H), 4.90-4.81 (m, 1H), 4.60 (t, 1H), 4.20 (t, 1H), 3.86 (dd, 1H), 3.64-3.52 (m, 4H), 2.62 (t, 2H), 1.95 (s, 6H).

HPLC (method 1): $R_t$=3.92 min
MS (ESIpos): m/z=502 (M+H)$^+$

Alternative Synthesis:

157 g (174 mmol) of the compound from Example 64A (alternative synthesis) are dissolved in 1.44 l of dichloromethane. At 15-20° C., 453 ml (5.32 mol) of concentrated hydrochloric acid are added dropwise, and the mixture is stirred at room temperature for 1 h. The phases are separated, the organic phase is discarded. The aqueous phase is washed twice with dichloromethane. Dichloromethane is then added to the aqueous phase, and the mixture is adjusted with cooling to pH=10 using 1:1 dilute aqueous sodium hydroxide solution. The phases are separated, and the organic phase is washed twice with water and then dried over sodium sulphate. After filtration, the filtrate is concentrated to dryness under reduced pressure. The residue is triturated with acetone, cooled to 10° C., filtered off at this temperature and washed with cold acetone. Drying gives 75 g (85% of theory) of the desired product.

$^1$H-NMR (400 MHz, DMSO-$d_6$, δ/ppm): δ=8.98 (t, 1H), 7.69 (d, 1H), 7.42 (dd, 1H), 7.42-7.38 (m, 2H), 7.25 (dd, 1H), 7.19 (d, 1H), 6.29 (t, 1H), 4.90-4.81 (m, 1H), 4.60 (t, 1H), 4.20 (t, 1H), 3.86 (dd, 1H), 3.64-3.52 (m, 4H), 2.62 (t, 2H), 1.95 (s, 6H).

HPLC (method 6): $R_t$=1.93 min
MS (ESIpos): m/z=502 (M+H)$^+$

Example 66A

2-[(2R)-3-({4-[3-(2-{[tert-Butyl(diphenyl)silyl]oxy}ethyl)-2-oxopyridin-1(2H)-yl]-3,5-dimethylphenyl}amino)-2-hydroxypropyl]-1H-isoindole-1,3(2H)-dione

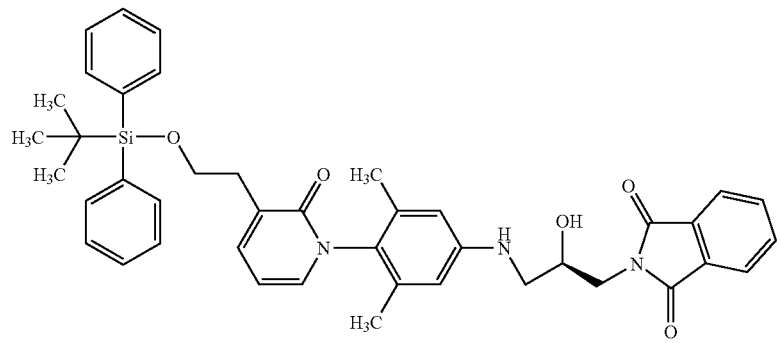 [SMILES: Cc1cc(NC[C@@H](O)CN2C(=O)c3ccccc3C2=O)cc(C)c1-n1cccc(CCO[Si](c2ccccc2)(c2ccccc2)C(C)(C)C)c1=O]

65 g (131 mmol) of the compound from Example 63A (alternative synthesis) are dissolved in 1.3 l of acetonitrile, and 27.9 g (137 mmol) of (S)-epoxyphthalimide and 43.8 g (196 mmol) of magnesium perchlorate are added. The mixture is stirred at room temperature for 15 h. Water and dichloromethane are then added, the phases are separated and the organic phase is dried over sodium sulphate. After filtration, the mixture is evaporated to dryness under reduced pressure. The residue is reacted further without further purification.

HPLC (method 14): $R_t$=1.73 min
MS (ESIpos): m/z=701 (M+H)$^+$

Example 67A

2-{[(5S)-3-{4-[3-(2-{[tert-Butyl(diphenyl)silyl]oxy}ethyl)-2-oxopyridin-1(2H)-yl]-3,5-dimethylphenyl}-2-oxo-1,3-oxazolidin-5-yl]methyl}-1H-isoindole-1,3(2H)-dione

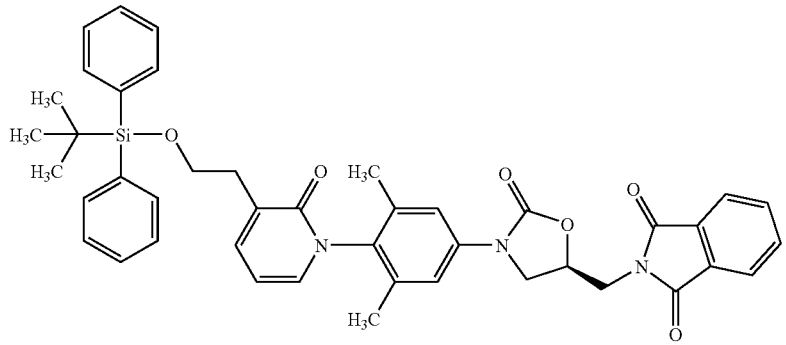 [SMILES: Cc1cc(N2C[C@H](CN3C(=O)c4ccccc4C3=O)OC2=O)cc(C)c1-n1cccc(CCO[Si](c2ccccc2)(c2ccccc2)C(C)(C)C)c1=O]

190 g (204 mmol) of the compound from Example 66A are dissolved in 1.0 l l of toluene. 66.0 g (407 mmol) of 1,1'-carbonyldiimidazole are then added, and the mixture is heated at reflux for one hour. The mixture is then cooled to room temperature, and water and dichloromethane are added. The phases are separated and the organic phase is dried over sodium sulphate. After filtration, the mixture is evaporated to dryness under reduced pressure. The residue is triturated with methanol, and the solid which remains is filtered off and washed with methanol. This gives 130 g (87% of theory) of the desired product.

$^1$H-NMR (400 MHz, DMSO-d$_6$, δ/ppm): δ=7.99-7.82 (m, 4H), 7.65-7.56 (m, 4H), 7.48-7.28 (m, 10H), 6.32 (t, 1H), 5.03-4.93 (m, 1H), 4.24 (dd, 1H), 4.00 (dd, 1H), 3.97-3.88 (m, 2H), 3.85 (t, 2H), 2.76 (t, 2H), 1.94 (s, 6H), 0.95 (s, 9H).
HPLC (method 14): $R_t$=1.74 min
MS (ESIpos): m/z=726 (M+H)$^+$ Example 68A 1-{4-[(5S)-5-(Aminomethyl)-2-oxo-1,3-oxazolidin-3-yl]-2,6-dimethylphenyl}-3-(2-{[tert-butyl-(diphenyl)silyl]oxy}ethyl)pyridin-2(1H)-one

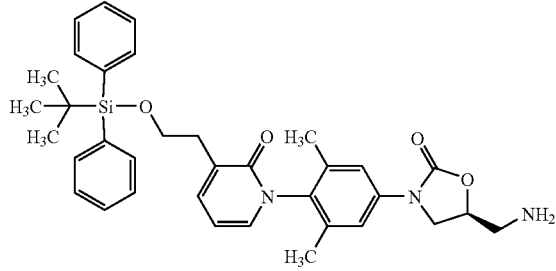 [SMILES: Cc1cc(N2C[C@H](CN)OC2=O)cc(C)c1-n1cccc(CCO[Si](c2ccccc2)(c2ccccc2)C(C)(C)C)c1=O]

130 g (179 mmol) of the compound from Example 67A are dissolved in 650 ml of ethanol, 193 ml (2.68 mol) of a 40% strength aqueous methanamine solution are added and the mixture is heated at 50-55° C. for one hour. After cooling to room temperature, water and dichloromethane are added, the phases are separated and the organic phase is dried over sodium sulphate. After filtration, the mixture is evaporated to dryness under reduced pressure. The residue (117 g, 89% of theory) is reacted further without further purification.

HPLC (method 6): $R_t$=2.05 min
MS (ESIpos): m/z=597 (M+H)$^+$

Example 69A 1-(2,6-Dimethyl-4-nitrophenyl)-3-methoxypyridin-2(1H)-one

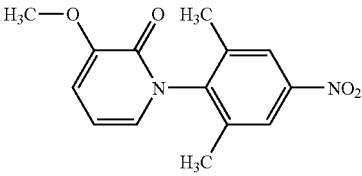

At 0° C., 452 mg (4.03 mmol) of potassium tert-butoxide are added to 336 mg (2.69 mmol) of 3-methoxypyridinone in 10 ml of DMF, and the mixture is stirred at room temperature for 30 min. 500 mg (2.96 mmol) of 1-fluoro-2,5-dimethyl-4-nitrobenzene are added, and the mixture is stirred at 80° C. After 22 h, the mixture is heated at 120° C. and stirred for a further 20 h. The mixture is then cooled and added to 100 ml of water and 15 ml of saturated aqueous sodium chloride solution. The mixture is extracted three times with in each case 300 ml of ethyl acetate, and the combined organic phases are dried over sodium sulphate. After filtration, the solvents are removed under reduced pressure and the residue is purified by chromatography on silica gel (cyclohexane/ethyl acetate 1:1). This gives 383 mg (52% of theory) of the desired compound.

$^1$H-NMR (300 MHz, DMSO-d$_6$, S/ppm): δ=8.16 (s, 2H), 7.04 (dd, 1H), 6.97 (dd, 1H), 6.38 (dd, 1H), 3.77 (s, 3H), 2.08 (s, 6H).
HPLC (method 1): $R_t$=2.84 min.
MS (DCI, m/z): 275 (M+H)$^+$.

Example 70A 1-(4-Amino-2,6-dimethylphenyl)-3-methoxypyridin-2(1H)-one 2.05 g (7.47 mmol) of the compound from Example 69A are dissolved in 70 ml of ethyl acetate and 70 ml of ethanol, 2.35 g (37.4 mmol) of ammonium formate and 0.39 g (0.37 mmol) of palladium/carbon (10%) are added and the mixture is stirred at 80° C. for 2 h. For work-up, the reaction solution is brought to room temperature and passed through a silica gel frit. The filter cake is washed with ethanol and the filtrate is concentrated under reduced pressure. The reaction product (1.65 g) is reacted without further purification.

$^1$H-NMR (300 MHz, DMSO-d$_6$, δ/ppm): δ=6.93-6.83 (m, 2H), 6.33 (s, 2H), 6.19 (dd, 1H), 5.12 (br.s, 2H), 3.72 (s, 3H), 1.78 (s, 6H).

LC-MS (method 1): R$_t$=2.90 min.

MS (DCI, m/z): 245 (M+H)$^+$.

Example 71A

5-Chloro-N-({(5S)-3-[4-(3-methoxy-2-oxopyridin-1(2H)-yl)-3,5-dimethylphenyl]-2-oxo-1,3-oxazolidin-5-yl}methyl)thiophene-2-carboxamide

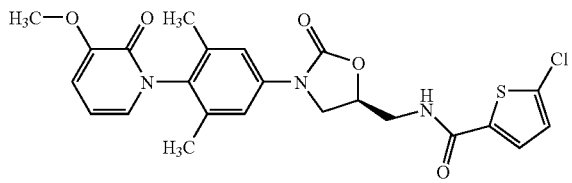 [SMILES: COc1cccn(-c2c(C)cc(N3C[C@H](CNC(=O)c4ccc(Cl)s4)OC3=O)cc2C)c1=O]

544 mg (2.50 mmol) of the compound from Example 1A are added to a solution of 555 mg (2.27 mmol) of the compound from Example 70A in 28 ml of acetonitrile. 761 mg (3.41 mmol) of magnesium perchlorate are added, and the suspension is then stirred at RT for 5.5 h. 736 mg (4.54 mmol) of 1,1'-carbonyldiimidazole and 28 mg (0.23 mmol) of DMAP are then added, and the mixture is heated at 60° C. After 18 h, another 28 mg (0.23 mmol) of DMAP are added. After 2 h at 70° C., the mixture is cooled and diluted with 100 ml of water. The aqueous phase is extracted three times with in each case 100 ml of ethyl acetate, and the combined organic phases are dried over sodium sulphate. After filtration, the filtrate is freed from the solvent and the residue is purified by chromatography on silica gel (dichloromethane/ethanol 20:1). Removal of the solvents gives 840 mg (69% of theory) of the desired product.

$^1$H-NMR 300 MHz, DMSO-d$_6$, S/ppm): δ=8.98 (t, 1H), 7.69 (d, 1H), 7.42-7.32 (m, 2H), 7.20 (dd, 1H), 7.00-6.88 (m, 2H), 6.28 (dd, 1H), 4.91-4.80 (m, 1H), 4.20 (dd, 1H), 3.90-3.82 (m, 1H), 3.75 (s, 3H), 3.60 (dd, 2H), 1.95 (s, 6H).

HPLC (method 14): R$_t$=1.02 min.

MS (ESIpos, m/z): 488 (M+H)$^+$.

Example 72A

5-Chloro-N-({(5S)-3-[4-(3-hydroxy-2-oxopyridin-1(2H)-yl)-3,5-dimethylphenyl]-2-oxo-1,3-oxazolidin-5-yl}methyl)thiophene-2-carboxamide

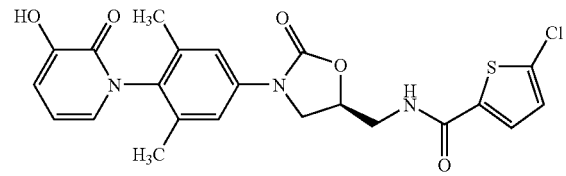 [SMILES: Cc1cc(N2C[C@H](CNC(=O)c3ccc(Cl)s3)OC2=O)cc(C)c1-n1cccc(O)c1=O]

830 mg (1.70 mmol) of the compound from Example 71A are dissolved in 50 ml of anhydrous dichloromethane and cooled to −78° C. At this temperature, 3.40 ml (3.40 mmol) of a 1 normal boron tribromide solution in dichloromethane are added dropwise such that the temperature does not exceed −65° C. The mixture is stirred at −78° C. for 2 h and then at RT for 2.5 h and kept at −20° C. for 15 h. At room temperature, the solution is carefully added to a saturated aqueous sodium bicarbonate solution. After phase separation, the aqueous phase is extracted three times with dichloromethane, and the combined organic phases are washed with saturated sodium chloride solution, dried over sodium sulphate, filtered and evaporated to dryness under reduced pressure. This gives 907 mg (69% of theory, purity according to LC-MS 61%) of the desired compound.

LC-MS (method 6): R$_t$=2.09 min.

MS (ESIpos, m/z): 474 (M+H)$^+$

Example 73A

5-Chloro-N-{[(5S)-3-{4-[3-(2-chloroethoxy)-2-oxopyridin-1(2H)-yl]-3,5-dimethylphenyl}-2-oxo-1,3-oxazolidin-5-yl]methyl}thiophene-2-carboxamide

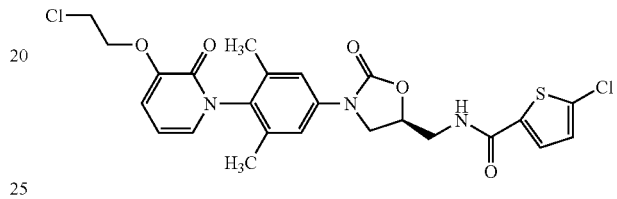

900 mg (1.89 mmol) of the compound from Example 72A and 1.36 g (9.49 mmol) of 1-bromo-2-chloroethane are dissolved in 30 ml of 1-methyl-2-pyrrolidone. 1.55 g (4.75 mmol) of caesium carbonate are added to the solution, and the mixture is stirred at 60° C. for 15 hours. Water is then added, and, after phase separation, the aqueous phase is extracted three times with tert-butyl methyl ether and three times with dichloromethane. The combined organic phases are washed successively with 1N aqueous sodium hydroxide solution and saturated sodium chloride solution and then dried over sodium sulphate. The drying agent is filtered off and the solvent is removed completely on a rotary evaporator. The residue is purified by chromatography on silica gel (cyclohexane/ethyl acetate 1:5). This gives 464 mg (45% of theory, purity according to LC-MS 74%) of the desired product.

HPLC (method 6): R$_t$=2.26 min

MS (ESIpos): m/z=536 (M+H)$^+$

WORKING EXAMPLES

Example 1

5-Chloro-N-{[(5S)-3-{4-[3-{[(2-hydroxyethyl)amino]methyl}-2-oxopyridin-1(2H)-yl]-3-methylphenyl}-2-oxo-1,3-oxazolidin-5-yl]methyl}thiophene-2-carboxamide

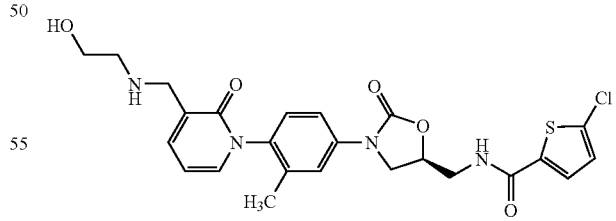

At −10° C., 38 mg (0.63 mmol) of aminoethanol are added to a solution of 56 mg (0.11 mmol) of the compound from Example 11A in 1 ml of DMF. After 30 min at −10° C., the mixture is added to water and then extracted three times with ethyl acetate. The organic phases are combined and then freed from the solvent under reduced pressure. The product is purified by preparative HPLC using an acetonitrile/water mixture. This gives 14.5 mg (26% of theory) of the desired product.

¹H-NMR (400 MHz, DMSO-d$_6$, δ/ppm): 9.00 (t, 1H), 8.28-8.15 (m, 2H), 7.70 (d, 1H), 7.60-7.48 (m, 3H), 7.45 (d, 1H), 7.23 (d, 1H), 7.20 (d, 1H), 6.35 (dd, 1H), 4.90-4.82 (m, 1H), 4.22 (dd, 1H), 3.88 (dd, 1H), 3.71-3.45 (m, 6H), 2.68 (dd, 2H), 2.02 (s, 3H).
HPLC (method 2): R$_t$=3.71 min.
MS (ESIpos, m/z): 517/519 ($^{35}$Cl/$^{37}$Cl) (M+H)$^+$.

Example 2

5-Chloro-N-{[(5S)-3-{3-methyl-4-[3-(2-morpholin-4-ylethyl)-2-oxopyridin-1(2H)-yl]phenyl}-2-oxo-1,3-oxazolidin-5-yl]methyl}thiophene-2-carboxamide

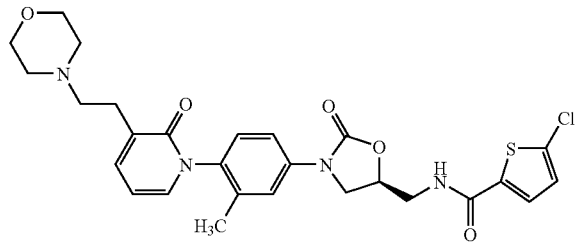 [SMILES: Cc1cc(N2C[C@H](CNC(=O)c3ccc(Cl)s3)OC2=O)ccc1-n1cccc(CCN2CCOCC2)c1=O]

100 mg (0.21 mmol) of Example 18A are dissolved in 5 ml of anhydrous dichloromethane and cooled to −78° C. At this temperature, 66 mg (0.62 mmol) of 2,6-dimethylpyridine and 69 mg (0.25 mmol) of trifluoromethanesulphonic anhydride are added, and the mixture is stirred for a further 10 min. 179 mg (2.05 mmol) of morpholine are then added, after 5 min, cooling is removed and the mixture is stirred at room temperature for 16 h. The solvent is removed under reduced pressure, and the residue is dissolved in a little methanol and purified by preparative HPLC using a gradient of acetonitrile and water. The product-containing fractions are combined and concentrated to dryness under reduced pressure. This gives 104 mg (91% of theory) of the desired compound.

¹H-NMR (400 MHz, DMSO-d$_6$, δ/ppm): δ=9.0 (t, 1H), 7.7 (d, 1H), 7.5 (m, 2H), 7.45 (dd, 1H), 7.35 (dd, 1H), 7.2 (m, 2H), 6.25 (t, 1H), 4.85 (m, 1H), 4.2 (t, 1H), 3.9 (m, 1H), 3.65 (t, 2H), 3.55 (m, 4H), 2.3-2.7 (m, 8H), 2.0 (s, 3H).

LC-MS (method 3): R$_t$=1.30 min
MS (ESIpos): m/z=556 (M+H$^+$)$^+$

Using the appropriate amine, the examples of the table below are prepared analogously to Example 2.

| Example | Structure | Characterization |
|---|---|---|
| 3 | 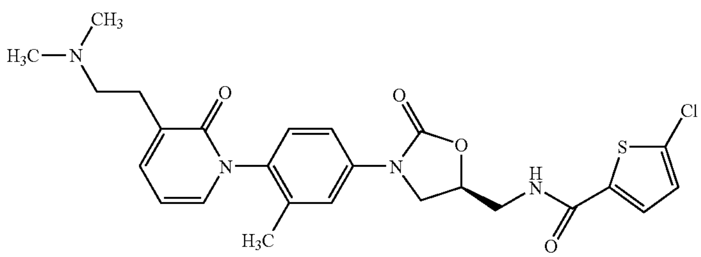 [SMILES: Cc1cc(N2C[C@H](CNC(=O)c3ccc(Cl)s3)OC2=O)ccc1-n1cccc(CCN(C)C)c1=O] | LC-MS (method 6): R$_t$ = 1.42 min<br>MS (ESIpos): m/z = 515 (M + H$^+$)$^+$<br>¹H-NMR (400 MHz, DMSO-d$_6$, δ/ppm): δ = 9.0 (t, 1H), 7.7 (d, 1H), 7.5 (m, 2H), 7.45 (dd, 1H), 7.35 (dd, 1H), 7.2 (m, 2H), 6.25 (t, 1H), 4.85 (m, 1H), 4.2 (t, 1H), 3.9 (m, 1H), 3.65 (t, 2H), 2.45 (m, 4H), 2.15 (s, 6H), 2.0 (s, 3H). |
| 4 | 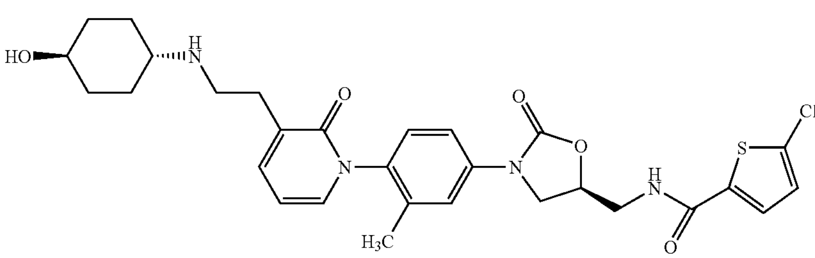 [SMILES: Cc1cc(N2C[C@H](CNC(=O)c3ccc(Cl)s3)OC2=O)ccc1-n1cccc(CCN[C@H]2CC[C@H](O)CC2)c1=O] | LC-MS (method 6): R$_t$ = 1.44 min<br>MS (ESIpos): m/z = 585 (M + H$^+$)$^+$<br>¹H-NMR (400 MHz, DMSO-d$_6$, δ/ppm): δ = 9.0 (t, 1H), 8.3 (s, 1H), 7.7 (d, 1H), 7.3-7.55 (m, 4H), 7.2 (m, 2H), 6.3 (t, 1H), 4.85 (m, 1H), 4.2 (t, 1H), 3.9 (m, 1H), 3.65 (t, 2H), 3.3 (m, 1H), 2.9 (t, 2H), 2.7 (m, 4H), 2.0 (s, 3H), 1.7-1.9 (m, 4H), 1.2 (m, 4H). |
| 5 | 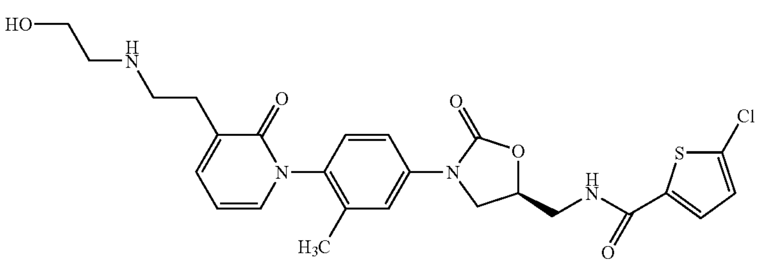 [SMILES: Cc1cc(N2C[C@H](CNC(=O)c3ccc(Cl)s3)OC2=O)ccc1-n1cccc(CCNCCO)c1=O] | LC-MS (method 11): R$_t$ = 1.80 min<br>MS (ESIpos): m/z = 531 (M + H$^+$)$^+$<br>¹H-NMR (400 MHz, DMSO-d$_6$, δ/ppm): δ = 9.0 (t, 1H), 8.3 (s, 1H), 7.7 (d, 1H), 7.55 (m, 2H), 7.45 (dd, 1H), 7.4 (dd, 1H), 7.2 (m, 2H), 6.3 (t, 1H), 4.85 (m, 1H), 4.2 (t, 1H), 3.9 (m, 1H), 3.65 (t, 2H), 3.55 (t, 2H), 2.95 (m, 2H), 2.8 (t, 2H), 2.75 (m, 2H), 2.0 (s, 3H). |

Example 6

5-Chloro-N-{[(5S)-3-{4-[3-{2-[(trans-4-hydroxycyclohexyl)amino]ethyl}-2-oxopyridin-1(2H)-yl]-3-methoxyphenyl}-2-oxo-1,3-oxazolidin-5-yl]methyl}thiophene-2-carboxamide

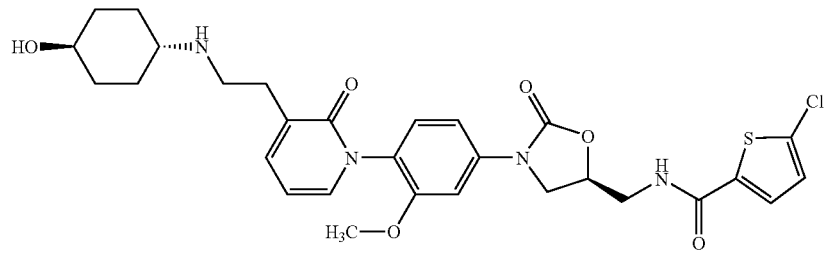 [SMILES: COc1cc(N2C[C@H](CNC(=O)c3ccc(Cl)s3)OC2=O)ccc1-n1cccc(CCN[C@H]2CC[C@H](O)CC2)c1=O]

19 g (38 mmol) of Example 25A are dissolved in 1000 ml of anhydrous dichloromethane and cooled to −78° C. At this temperature, 12.3 g (115 mmol) of 2,6-dimethylpyridine and 16 g (57 mmol) of trifluoromethanesulphonic anhydride are added. The mixture is stirred at −78° C. for 1.5 h, and 44 g (383 mmol) of trans-4-aminocyclohexanol, dissolved in 250 ml of dichloromethane and 50 ml of N,N-dimethylformamide, are then added. Cooling is removed, the mixture is stirred at room temperature for 16 h and the solvent is then removed under reduced pressure. The residue is dissolved in a little methanol and purified by preparative HPLC using a gradient of acetonitrile and water. The product-containing fractions are combined and concentrated to dryness under reduced pressure. This gives 15.2 g (73% of theory) of the desired compound.

$^1$H-NMR (400 MHz, CDCl$_3$, S/ppm): δ=7.72-7.52 (m, 1H), 7.50-7.37 (m, 2H), 7.32 (dd, 1H), 7.21 (d, 1H), 7.10 (dd, 1H), 6.92-6.84 (m, 2H), 6.20 (t, 1H), 4.81-4.66 (m, 1H), 4.10-3.95 (m, 1H), 3.87-3.66 (m, 6H), 3.64-3.50 (m, 2H), 2.95-2.84 (m, 2H), 2.78-2.68 (m, 2H), 2.52-2.41 (m, 1H), 1.98-1.78 (m, 5H), 1.33-1.05 (m, 4H).

LC-MS (method 6): R$_t$=1.40 min
MS (ESIpos): m/z=602 (M+H$^+$)$^+$

Using the appropriate amine, the examples of the table below are prepared analogously to Example 6.

| Example | Structure | Characterization |
|---|---|---|
| 7 | (morpholine-ethyl analog) | LC-MS (method 6): R$_t$ = 1.41 min<br>MS (ESIpos): m/z = 573 (M + H$^+$)$^+$<br>$^1$H-NMR (400 MHz, DMSO-d$_6$, δ/ppm): δ = 9.0 (t, 1H), 7.7 (d, 1H), 7.45 (d, 1H), 7.35 (dd, 1H), 7.3 (dd, 1H), 7.25 (d, 1H), 7.2 (d, 1H), 7.1 (d, 1H), 6.2 (t, 1H), 4.85 (m, 1H), 4.25 (t, 1H), 3.9 (m, 1H), 3.75 (s, 3H), 3.65 (t, 2H), 3.5 (m, 4H), 2.4-2.6 (m, 6H), 2.4 (m, 2H). |
| 8 | (N,N-dimethylamino-ethyl analog) | LC-MS (method 6): R$_t$ = 1.40 min<br>MS (ESIpos): m/z = 531 (M + H$^+$)$^+$<br>$^1$H-NMR (400 MHz, DMSO-d$_6$, δ/ppm): δ = 9.0 (t, 1H), 7.7 (d, 1H), 7.45 (d, 1H), 7.35 (dd, 1H), 7.3 (dd, 1H), 7.25 (d, 1H), 7.2 (d, 1H), 7.1 (d, 1H), 6.2 (t, 1H), 4.85 (m, 1H), 4.25 (t, 1H), 3.9 (m, 1 H), 3.75 (s, 3H), 3.65 (t, 2H), 2.4-2.6 (m, 4H), 2.1 (s, 6H). |

Example 9

5-Chloro-N-{[(5S)-3-{4-[3-{2-[(2-hydroxyethyl)amino]ethyl}-2-oxopyridin-1(2H)-yl]-3-(methoxymethyl)phenyl}-2-oxo-1,3-oxazolidin-5-yl]methyl}thiophene-2-carboxamide

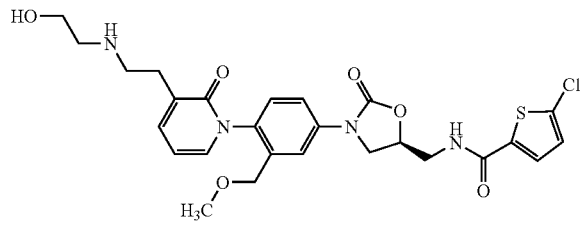 [SMILES: COCc1cc(N2C[C@H](CNC(=O)c3ccc(Cl)s3)OC2=O)ccc1-n1cccc(CCNCCO)c1=O]

14 g (27 mmol) of Example 34A are dissolved in 660 ml of anhydrous dichloromethane and cooled to −78° C. At this temperature, 8.7 g (81 mmol) of 2,6-dimethylpyridine and 13 g (46 mmol) of trifluoromethanesulphonic anhydride are added. After 10 min at −78° C., 8.2 g (135 mmol) of 2-aminoethanol are added, after a further 5 min cooling is removed, and the mixture is then stirred at room temperature for 16 h. The solvent is removed under reduced pressure, and the residue is dissolved in a little methanol and purified by preparative HPLC using a gradient of acetonitrile and water. The product-containing fractions are combined and concentrated to dryness under reduced pressure. This gives 11.1 g (73% of theory) of the desired compound.

$^1$H-NMR (400 MHz, DMSO-$d_6$, δ/ppm): δ=8.98 (t, 1H), 7.71-7.65 (m, 2H), 7.62-7.55 (m, 1H), 7.40 (dd, 1H), 7.35 (dd, 1H), 7.28 (d, 1H), 7.20 (d, 1H), 6.25 (t, 1H), 4.90-4.82 (m, 1H), 4.42 (t, 1H), 4.27-4.08 (m, 3H), 3.94-3.88 (m, 1H), 3.63 (t, 2H), 3.45 (dt, 2H), 3.18 (s, 3H), 2.75-2.68 (m, 2H), 2.61-2.43 (m, 4H).

LC-MS (method 6): $R_t$=1.34 min
MS (ESIpos): m/z=561 (M+H$^+$)$^+$

Example 10

5-Chloro-N-{[(5S)-3-{4-[3-{2-[(trans-4-hydroxycyclohexyl)amino]ethyl}-2-oxopyridin-1(2H)-yl]-3-(methoxymethyl)phenyl}-2-oxo-1,3-oxazolidin-5-yl]methyl}thiophene-2-carboxamide

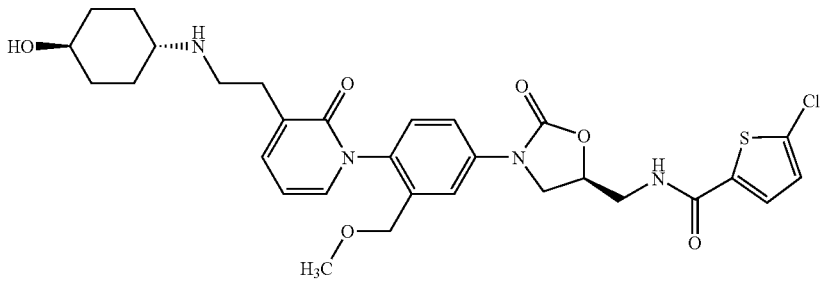 [SMILES: COCc1cc(N2C[C@H](CNC(=O)c3ccc(Cl)s3)OC2=O)ccc1-n1cccc(CCN[C@H]2CC[C@H](O)CC2)c1=O]

900 mg (1.7 mmol) of Example 34A are dissolved in 42 ml of anhydrous dichloromethane and cooled to −78° C. 560 mg (5.2 mmol) of 2,6-dimethylpyridine and 833 mg (2.9 mmol) of trifluoromethanesulphonic anhydride are added, and the mixture is stirred at −78° C. for 1.5 h. 1 g (8.7 mmol) of trans-4-aminocyclohexanol is added, cooling is removed after 5 min and the mixture is then stirred at room temperature for 18 h. The mixture is diluted with water and dichloromethane, and the organic phase is separated off, dried over sodium sulphate, filtered and evaporated under reduced pressure. The residue is taken up in a little methanol and purified by preparative HPLC using a gradient of acetonitrile and water. The product-containing fractions are combined and concentrated to dryness under reduced pressure. This gives 655 mg (61% of theory) of the desired compound.

$^1$H-NMR (400 MHz, DMSO-$d_6$, δ/ppm): δ=8.98 (t, 1H), 7.71-7.65 (m, 2H), 7.62-7.55 (m, 1H), 7.40 (dd, 1H), 7.35 (dd, 1H), 7.27 (d, 1H), 7.20 (d, 1H), 6.25 (t, 1H), 4.90-4.82 (m, 1H), 4.44 (d, 1H), 4.27-4.07 (m, 3H), 3.93-3.83 (m, 1H), 3.62 (t, 2H), 3.18 (s, 3H), 2.76-2.65 (m, 2H), 2.57-2.48 (m, 2H), 2.36-2.27 (m, 2H), 1.84-1.72 (m, 4H), 1.19-1.06 (m, 2H), 1.03-0.91 (m, 2H).

LC-MS (method 6): $R_t$=1.68 min
MS (ESIpos): m/z=615 (M+H$^+$)$^+$

Using the appropriate amine, the examples of the table below are prepared analogously to Example 10.

| Example | Structure | Characterization |
|---|---|---|
| 11 | 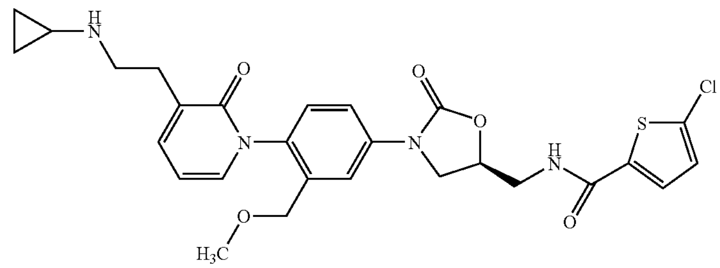 [SMILES: COCc1cc(N2C[C@H](CNC(=O)c3ccc(Cl)s3)OC2=O)ccc1-n1cccc(CCNC2CC2)c1=O] | LC-MS (method 11): $R_t$ = 1.94 min<br>MS (ESIpos): m/z = 557 $(M + H^+)^+$<br>$^1$H-NMR (400 MHz, DMSO-$d_6$, δ/ppm): δ = 9.0 (t, 1H), 7.7 (m, 2H), 7.6 (m, 1H), 7.4 (dd, 1H), 7.35 (dd, 1H), 7.25 (d, 1H), 7.2 (d, 1H), 6.25 (t, 1H), 4.85 (m, 1H), 4.2 (m, 2H), 4.1 (d, 1H), 3.9 (m, 1H), 3.6 (t, 2H), 3.3 (m, 2H), 3.2 (s, 3H), 2.8 (m, 2H), 2.1 (m, 2H), 0.45 (m, 2H), 0.2 (m, 2H). |
| 12 | 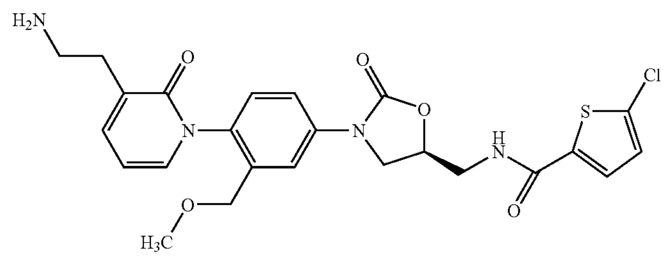 [SMILES: COCc1cc(N2C[C@H](CNC(=O)c3ccc(Cl)s3)OC2=O)ccc1-n1cccc(CCN)c1=O] | LC-MS (method 11): $R_t$ = 1.86 min<br>MS (ESIpos): m/z = 517 $(M + H^+)^+$<br>$^1$H-NMR (400 MHz, DMSO-$d_6$, δ/ppm): δ = 9.0 (t, 1H), 7.7 (m, 2H), 7.6 (m, 1H), 7.4 (m, 2H), 7.25 (d, 1H), 7.2 (d, 1H), 6.25 (t, 1H), 4.85 (m, 1H), 4.2 (m, 2H), 4.1 (d, 1H), 3.9 (m, 1H), 3.6 (t, 2H), 3.2 (s, 3H), 2.8 (m, 2H), 2.55 (m, 2H). |
| 13 | 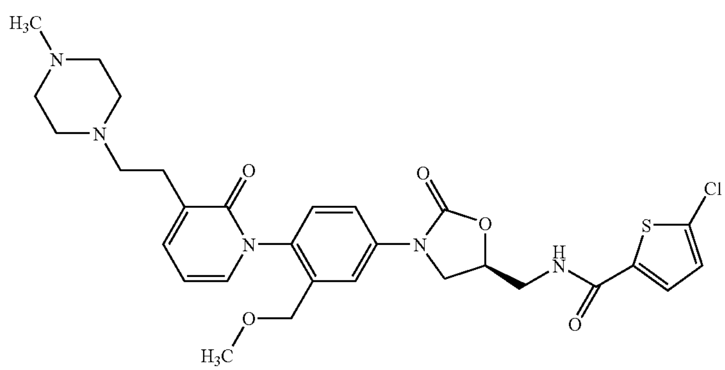 [SMILES: COCc1cc(N2C[C@H](CNC(=O)c3ccc(Cl)s3)OC2=O)ccc1-n1cccc(CCN2CCN(C)CC2)c1=O] | LC-MS (method 11): $R_t$ = 1.69 min<br>MS (ESIpos): m/z = 600 $(M + H^+)^+$<br>$^1$H-NMR (400 MHz, DMSO-$d_6$, δ/ppm): δ = 9.0 (t, 1H), 7.7 (m, 2H), 7.6 (m, 1H), 7.4 (dd, 1H), 7.35 (dd, 1H), 7.25 (d, 1H), 7.2 (d, 1H), 6.25 (t, 1H), 4.85 (m, 1H), 4.2 (m, 2H), 4.1 (d, 1H), 3.9 (m, 1H), 3.6 (t, 2H), 3.2 (s, 3H), 2.2-2.8 (m, 12H), 2.15 (s, 3H). |
| 14 | 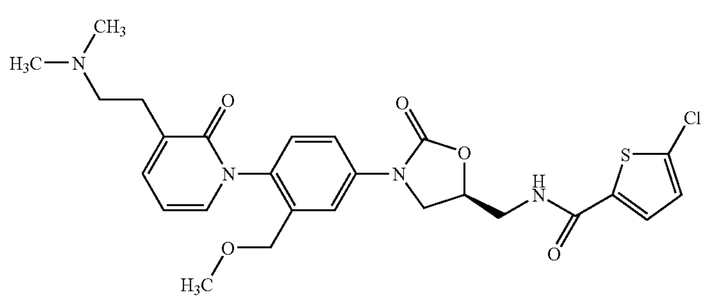 [SMILES: COCc1cc(N2C[C@H](CNC(=O)c3ccc(Cl)s3)OC2=O)ccc1-n1cccc(CCN(C)C)c1=O] | LC-MS (method 11): $R_t$ = 1.91 min<br>MS (ESIpos): m/z = 545 $(M + H^+)^+$<br>$^1$H-NMR (400 MHz, DMSO-$d_6$, δ/ppm): δ = 9.0 (t, 1H), 7.7 (m, 2H), 7.6 (m, 1H), 7.4 (m, 2H), 7.25 (d, 1H), 7.2 (d, 1H), 6.25 (t, 1H), 4.85 (m, 1H), 4.2 (m, 2H), 4.1 (d, 1H), 3.9 (m, 1H), 3.6 (t, 2H), 3.2 (s, 3H), 2.3-2.7 (m, 4H), 2.15 (s, 6H). |
| 15 | 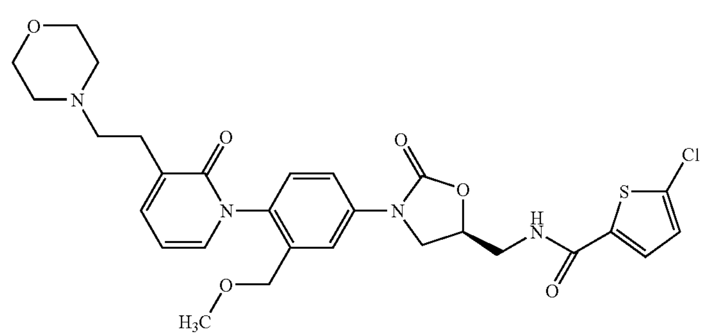 [SMILES: COCc1cc(N2C[C@H](CNC(=O)c3ccc(Cl)s3)OC2=O)ccc1-n1cccc(CCN2CCOCC2)c1=O] | LC-MS (method 11): $R_t$ = 1.87 min<br>MS (ESIpos): m/z = 587 $(M + H^+)^+$<br>$^1$H-NMR (400 MHz, DMSO-$d_6$, δ/ppm): δ = 9.0 (t, 1H), 7.7 (m, 2H), 7.6 (m, 1H), 7.4 (dd, 1H), 7.35 (dd, 1H), 7.25 (d, 1H), 7.2 (d, 1H), 6.25 (t, 1H), 4.85 (m, 1H), 4.2 (m, 2H), 4.1 (d, 1H), 3.9 (m, 1H), 3.6 (t, 2H), 3.55 (m, 4H), 3.2 (s, 3H), 2.3-2.8 (m, 8H). |

| Example | Structure | Characterization |
|---|---|---|
| 16 | 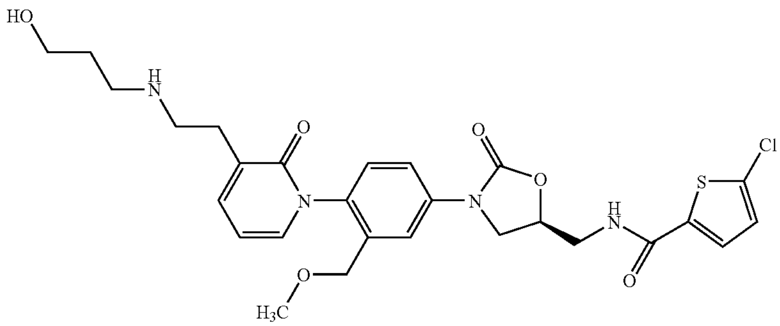 [SMILES: COCc1cc(N2C[C@H](CNC(=O)c3ccc(Cl)s3)OC2=O)ccc1-n1cccc(CCNCCCO)c1=O] | LC-MS (method 11): $R_t$ = 1.89 min<br>MS (ESIpos): m/z = 575 $(M + H^+)^+$<br>$^1$H-NMR (400 MHz, DMSO-$d_6$, δ/ppm): δ = 9.0 (t, 1H), 7.7 (m, 2H), 7.6 (m, 1H), 7.4 (dd, 1H), 7.35 (dd, 1H), 7.25 (d, 1H), 7.2 (d, 1H), 6.25 (t, 1H), 4.85 (m, 1H), 4.2 (m, 2H), 4.1 (d, 1H), 3.9 (m, 1H), 3.6 (t, 2H), 3.45 (t, 2H), 3.2 (s, 3H), 2.7 (t, 2H), 2.4-2.6 (m, 6H), 1.5 (m, 2H). |
| 17 | 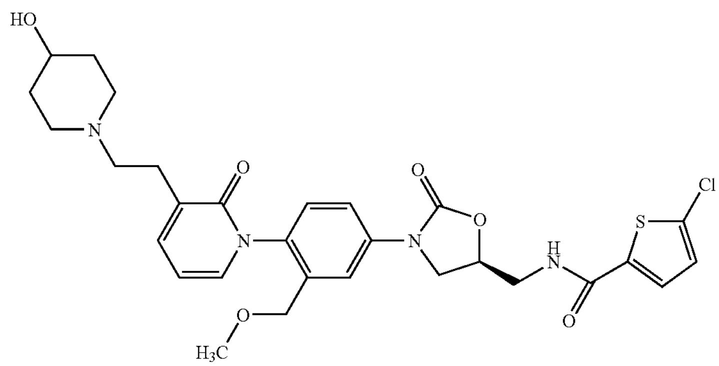 [SMILES: COCc1cc(N2C[C@H](CNC(=O)c3ccc(Cl)s3)OC2=O)ccc1-n1cccc(CCN2CCC(O)CC2)c1=O] | LC-MS (method 11): $R_t$ = 1.89 min<br>MS (ESIpos): m/z = 601 $(M + H^+)^+$<br>$^1$H-NMR (400 MHz, DMSO-$d_6$, δ/ppm): δ = 9.0 (t, 1H), 7.7 (m, 2H), 7.6 (m, 1H), 7.4 (dd, 1H), 7.35 (dd, 1H), 7.25 (d, 1H), 7.2 (d, 1H), 6.25 (t, 1H), 4.85 (m, 1H), 4.2 (m, 2H), 4.1 (d, 1H), 3.9 (m, 1H), 3.6 (t, 2H), 3.45 (m, 1H), 3.2 (s, 3H), 2.7 (m, 2H), 2.3-2.6 (m, 4H), 2.0 (t, 2H), 1.7 (m, 2H), 1.3 (m, 2H). |

Example 18

5-Chloro-N-{[(5S)-3-{4-[3-{3-[(trans-4-hydroxycyclohexyl)amino]propyl}-2-oxopyridin-1(2H)-yl]-3-methylphenyl}-2-oxo-1,3-oxazolidin-5-yl]methyl}thiophene-2-carboxamide

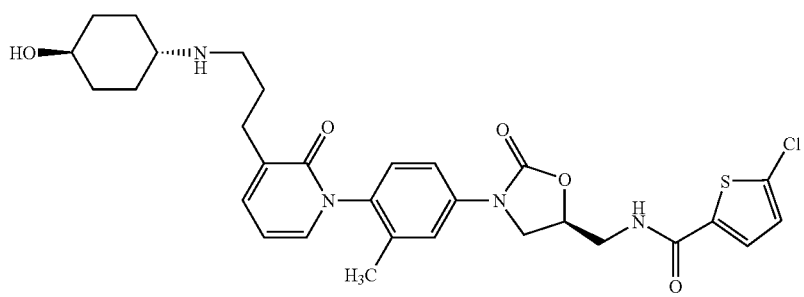 [SMILES: Cc1cc(N2C[C@H](CNC(=O)c3ccc(Cl)s3)OC2=O)ccc1-n1cccc(CCCN[C@H]2CC[C@H](O)CC2)c1=O]

92.4 mg (0.18 mmol) of Example 38A are dissolved in 4.5 ml of anhydrous dichloromethane and cooled to −78° C., and 67 mg (0.55 mmol) of 2,6-dimethylpyridine and 78 mg (0.28 mmol) of trifluoromethanesulphonic anhydride are added. After 1 h at −78° C., 106 mg (0.920 mmol) of trans-4-aminocyclohexanol are added, cooling is removed and the mixture is stirred at room temperature for 72 h. After addition of 2.5 ml of methanol, the mixture is stirred for 5 min and the solvent is then removed under reduced pressure. The residue is purified by preparative HPLC using a gradient of acetonitrile and 0.2% strength trifluoromethanesulphonic acid in water. This gives 7.5 mg (7% of theory) of the desired compound.

$^1$H-NMR (400 MHz, DMSO-$d_6$, δ/ppm): δ=8.99 (t, 1H), 8.37-8.21 (m, 2H), 7.70 (d, 1H), 7.58-7.47 (m, 2H), 7.45-7.36 (m, 2H), 7.22 (d, 1H), 7.20 (d, 1H), 6.32 (dd, 1H), 4.92-4.78 (m, 1H), 4.21 (dd, 1H), 4.00-3.48 (m, 4H), 3.41-3.30 (m, 1H), 2.98-2.85 (m, 2H), 2.02 (s, 3H), 2.00-1.91 (m, 2H), 1.88-1.80 (m, 4H), 1.37-1.15 (m, 6H).

LC-MS (method 6): $R_t$=1.45 min
MS (ESIpos): m/z=601 (M+H)$^+$

Example 19

5-Chloro-N-{[(5S)-3-{4-[3-{3-[(2-hydroxyethyl)amino]propyl}-2-oxopyridin-1(2H)-yl]-3-methyl-phenyl}-2-oxo-1,3-oxazolidin-5-yl]methyl}thiophene-2-carboxamide

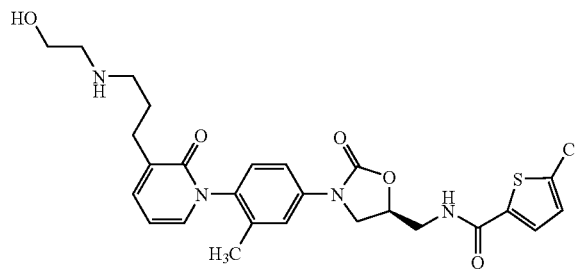 [SMILES: Cc1cc(N2C[C@H](CNC(=O)c3ccc(Cl)s3)OC2=O)ccc1-n1cccc(CCCNCCO)c1=O]

92.4 mg (0.18 mmol) of Example 38A are dissolved in 4.5 ml of anhydrous dichloromethane and cooled to −78° C., and 67 mg (0.55 mmol) of 2,6-dimethylpyridine and 78 mg (0.28 mmol) of trifluoromethanesulphonic anhydride are added. After 1 h at −78° C., 112 mg (1.84 mmol) of aminoethanol are added, cooling is removed and the mixture is stirred at room temperature for 72 h. After addition of 2.5 ml of methanol, the mixture is stirred for 5 min and the solvent is then removed under reduced pressure. The residue is purified by preparative HPLC using a gradient of acetonitrile and 0.2% strength trifluoromethanesulphonic acid in water. This gives 14 mg (14% of theory) of the desired compound.

$^1$H-NMR (400 MHz, DMSO-$d_6$, δ/ppm): δ=8.99 (t, 1H), 8.51-8.37 (m, 2H), 7.70 (d, 1H), 7.58-7.47 (m, 2H), 7.45-7.38 (m, 2H), 7.22 (d, 1H), 7.20 (d, 1H), 6.32 (dd, 1H), 4.91-4.82 (m, 1H), 4.22 (dd, 1H), 3.95-3.50 (m, 7H), 3.05-2.89 (m, 4H), 2.02 (s, 3H), 1.93-1.82 (m, 2H).

LC-MS (method 6): $R_t$=1.45 min
MS (ESIpos): m/z=546 (M+H)$^+$

Example 20

5-Chloro-N-{[(5S)-3-{3-methyl-4-[2-oxo-3-{2-[(tetrahydrofuran-2-ylmethyl)amino]ethoxy}pyridin-1(2H)-yl]phenyl}-2-oxo-1,3-oxazolidin-5-yl]methyl}thiophene-2-carboxamide

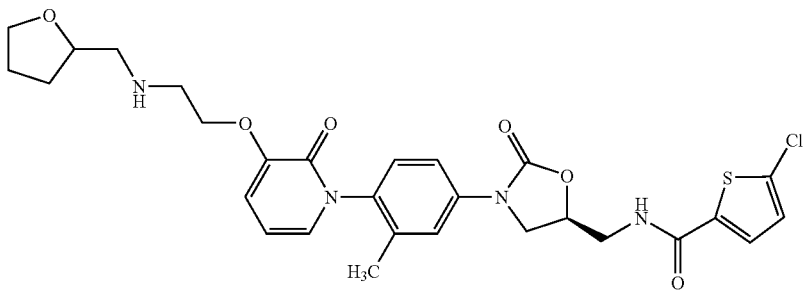 [SMILES: Cc1cc(N2C[C@H](CNC(=O)c3ccc(Cl)s3)OC2=O)ccc1-n1cccc(OCCNCC2CCCO2)c1=O]

80.0 mg (153 µmol) of Example 46A, 23 mg (153 µmol) of sodium iodide and 105 µl (77.4 mg, 766 µmol) of 1-(tetrahydrofuran-2-yl)methanamine in 2 ml of absolute 1,2-dimethoxyethane are stirred at 90° C. for 8 hours. For work-up, the concentrated reaction solution is subjected to fine purification by preparative RP-HPLC using an acetonitrile/water mixture. This gives 60 mg (67% of theory) of product.

$^1$H-NMR (400 MHz, DMSO-$d_6$, δ/ppm): 8.97 (t, 1H), 7.69 (d, 1H), 7.55-7.46 (m, 2H), 7.25-7.18 (m, 2H), 7.04 (d, 1H), 6.93 (d, 1H), 6.21 (t, 1H), 4.87 (m, 1H), 4.22 (dd, 1H), 3.97 (m, 2H), 3.90-3.81 (m, 2H), 3.72 (m, 2H), 3.66-3.55 (m, 3H), 2.90 (m, 2H), 2.62 (d, 2H), 2.01 (s, 3H), 1.95-1.80 (m, 3H), 1.57-1.96 (m, 1H).

LC-MS (method 3): $R_t$=1.45 min
MS (ESIpos): m/z=587 (M+H)$^+$

Example 21

5-Chloro-N-{[(5S)-3-{4-[3-{2-[(trans-4-hydroxycyclohexyl)amino]ethoxy}-2-oxopyridin-1(2H)-yl]-3-methylphenyl}-2-oxo-1,3-oxazolidin-5-yl]methyl}thiophene-2-carboxamide

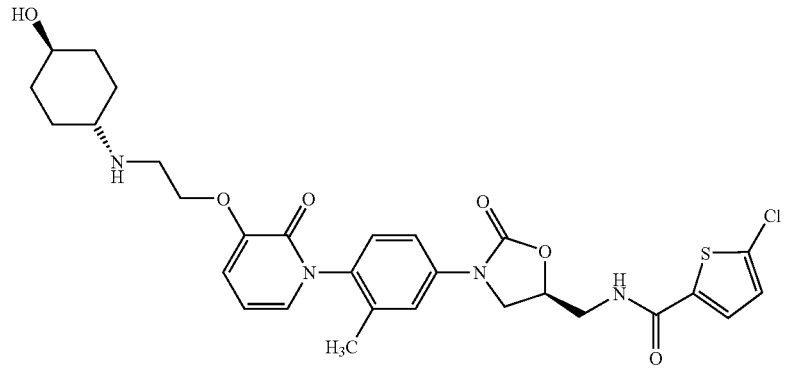

70.0 mg (134 µmol) of Example 46A, 20.0 mg (134 µmol) of sodium iodide and 77.2 mg (670 µmol) of trans-4-aminocyclohexanol in 1.75 ml of absolute 1,2-dimethoxyethane are stirred at 90° C. for 8 hours. For work-up, the concentrated reaction solution is subjected to fine purification by preparative RP-HPLC using an acetonitrile/water mixture. This gives 57 mg (69% of theory) of product.

$^1$H-NMR (400 MHz, DMSO-$d_6$, δ/ppm): 8.97 (t, 1H), 7.69 (d, 1H), 7.53-7.50 (m, 2H), 7.23-7.18 (m, 2H), 7.04 (d, 1H), 6.92 (d, 1H), 6.22 (t, 1H), 4.89-4.81 (m, 1H), 4.44 (d, 1H), 4.22 (t, 1H), 3.99-3.82 (m, 3H), 3.62 (t, 3H), 2.87 (t, 2H), 2.41-2.31 (m, 1H), 2.01 (s, 3H), 1.80 (t, 4H), 1.53 (bs, 1H), 1.19-0.93 (m, 4H).

LC-MS (method 3): $R_t$=1.41 min

MS (ESIpos): m/z=601 (M+H)$^+$.

Using the appropriate amine, the examples of the table below are prepared analogously to Example 21.

| Example | Structure | Characterization |
|---|---|---|
| 22 | (pyrrolidinyl-ethoxy pyridone · HCl salt variant) | LC-MS (method 3): $R_t$ = 1.56 min, MS (ESIpos): m/z = 557 (M + H)$^+$ $^1$H-NMR (400 MHz, DMSO-$d_6$, δppm): 10.67 (broad s, 1H), 9.06 (t, 1H), 7.73 (d, 1H), 7.58-7.48 (m, 2H), 7.28-7.13 (m, 3H), 7.10 (d, 1H), 6.28 (t, 1H), 4.86 (m, 1H), 4.32 (m, 2H), 4.22 (t, 1H), 3.90 (m, 1H), 3.68-3.53 (m, 5H), 3.10 (m, 2H), 2.08-1.93 (m, 5H, darin 2.01 (s, 3H)), 1.92-1.80 (m, 2H). |
| 23 | (cyclobutylamino-ethoxy pyridone variant) | LC-MS (method 11): $R_t$ = 2.13 min, MS (ESIpos): m/z = 557 (M + H)$^+$ $^1$H-NMR (400 MHz, DMSO-$d_6$, δ/ppm): 8.97 (t, 1H), 7.69 (d, 1H), 7.55-7.46 (m, 2H), 7.25-7.18 (m, 2H), 7.04 (d, 1H), 6.92 (d, 1H), 6.21 (t, 1H), 4.87 (m, 1H), 4.22 (dd, 1H), 3.97-3.83 (m, 3H), 3.60 (t, 2H), 3.20 (m, 1H), 2.80 (t, 2H), 2.16-2.05 (m, 2H), 2.01 (s, 3H), 1.72-1.48 (m, 4H). |

-continued

| Example | Structure | Characterization |
|---|---|---|
| 24 | 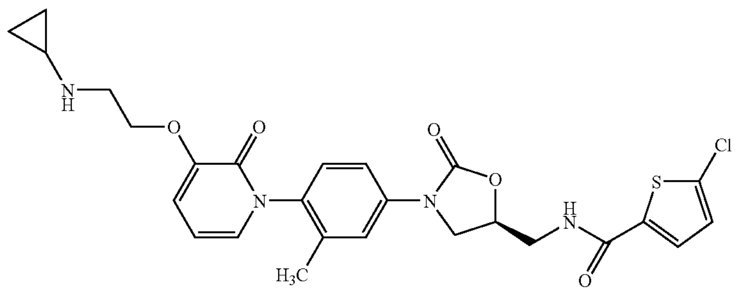 [SMILES: Cc1cc(N2C[C@H](CNC(=O)c3ccc(Cl)s3)OC2=O)ccc1-n1cccc(OCCNC2CC2)c1=O] | LC-MS (method 11): $R_t$ = 2.03 min, MS (ESIpos): m/z = 543 $(M + H)^+$ $^1$H-NMR (400 MHz, DMSO-d$_6$, δ/ppm): 8.97 (t, 1H), 7.69 (d, 1H), 7.55-7.46 (m, 2H), 7.25-7.18 (m, 2H), 7.04 (d, 1H), 6.21 (d, 1H), 6.72 (t, 1H), 4.87 (m, 1H), 4.22 (dd, 1H), 3.98 (m, 2H), 3.89 (m, 1H), 3.60 (t, 2H), 2.94 (t, 2H), 2.14 (m, 1H), 2.01 (s, 3H), 0.38 (m, 2H), 0.22 (m, 2H). |
| 25 | 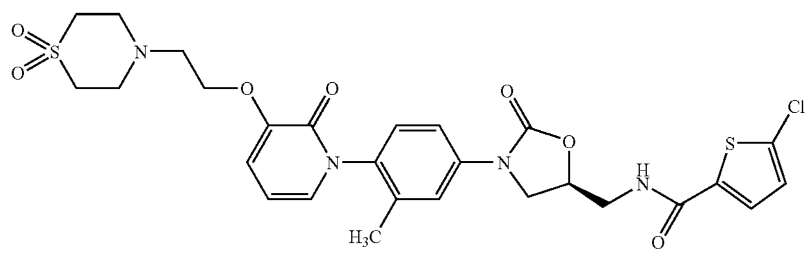 [SMILES: Cc1cc(N2C[C@H](CNC(=O)c3ccc(Cl)s3)OC2=O)ccc1-n1cccc(OCCN2CCS(=O)(=O)CC2)c1=O] | LC-MS (method 11): $R_t$ = 2.03 min, MS (ESIpos): m/z = 621 $(M + H)^+$ $^1$H-NMR (400 MHz, DMSO-d$_6$, δ/ppm): 8.97 (broad s, 1H), 7.70 (d, 1H), 7.55-7.46 (m, 2H), 7.25-7.18 (m, 2H), 7.06 (d, 1H), 6.95 (d, 1H), 6.21 (t, 1H), 4.86 (m, 1H), 4.22 (dd, 1H), 4.03 (m, 2H), 3.78 (m, 1H), 3.61 (t, 2H), 3.12-2.98 (m, 8H), 2.93 (t, 2H), 2.01 (s, 3H). |
| 26 | 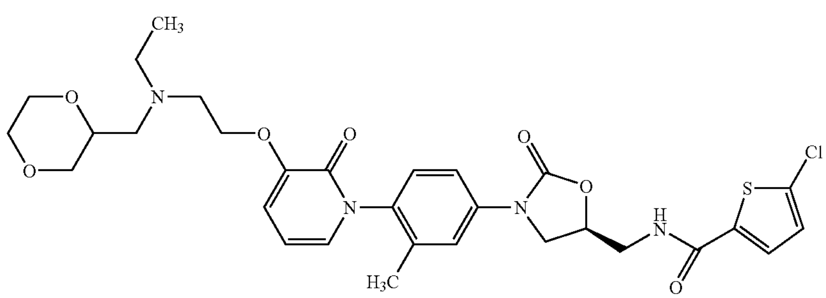 | LC-MS (method 11): $R_t$ = 2.03 min, MS (ESIpos): m/z = 621 $(M + H)^+$ $^1$H-NMR (400 MHz, DMSO-d$_6$, δ/ppm): 8.96 (t, 1H), 7.70 (d, 1H), 7.55-7.46 (m, 2H), 7.25-7.18 (m, 2H), 7.06 (d, 1H), 6.92 (d, 1H), 6.70 (t, 1H), 4.86 (m, 1H), 4.22 (dd, 1H), 3.95 (m, 2H), 3.88 (m, 1H), 3.78-3.50 (m, 7H), 3.41 (td, 1H), 3.18 (t, 1H), 2.82 (m, 2H), 2.65-2.45 (m, 4H), 2.02 (s, 3H), 0.95 (t, 3H). |
| 27 | 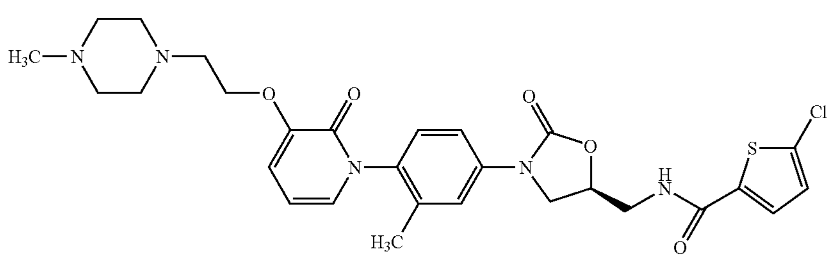 [SMILES: Cc1cc(N2C[C@H](CNC(=O)c3ccc(Cl)s3)OC2=O)ccc1-n1cccc(OCCN2CCN(C)CC2)c1=O] | LC-MS (method 6): $R_t$ = 1.41 min, MS (ESIpos): m/z = 586 $(M + H)^+$ $^1$H-NMR (400 MHz, DMSO-d$_6$, δ/ppm): 8.97 (t, 1H), 7.70 (d, 1H), 7.55-7.46 (m, 2H), 7.25-7.18 (m, 2H), 7.06 (d, 1H), 6.95 (d, 1H), 6.22 (t, 1H), 4.86 (m, 1H), 4.22 (dd, 1H), 4.03 (m, 2H), 3.88 (m, 1H), 3.61 (t, 2H), 2.68 (t, 2H), 2.48 (m, 4H), 2.29 (m, 4H), 2.15 (s, 3H), 2.01 (s, 3H). |
| 28 | 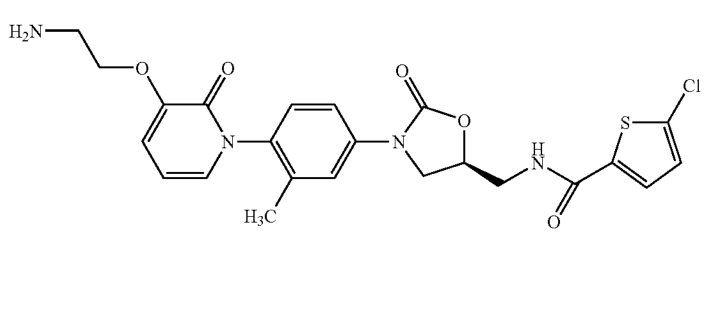 [SMILES: Cc1cc(N2C[C@H](CNC(=O)c3ccc(Cl)s3)OC2=O)ccc1-n1cccc(OCCN)c1=O] | LC-MS (method 6): $R_t$ = 1.43 min, MS (ESIpos): m/z = 503 $(M + H)^+$ $^1$H-NMR (400 MHz, DMSO-d$_6$, δ/ppm): 8.97 (t, 1H), 7.70 (d, 1H), 7.55-7.46 (m, 2H), 7.25-7.18 (m, 2H), 7.06 (d, 1H), 6.92 (d, 1H), 6.21 (t, 1H), 4.86 (m, 1H), 4.22 (dd, 1H), 3.93-3.80 (m, 3H), 3.61 (t, 2H), 2.88 (t, 2H), 2.02 (s, 3H). |

| Example | Structure | Characterization |
|---|---|---|
| 29 | 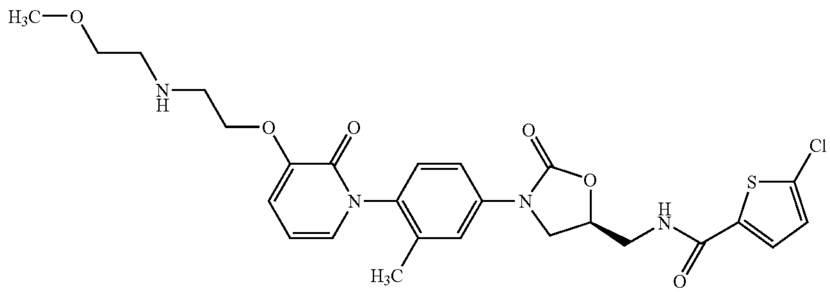 [SMILES: COCCNCCOc1cccn(-c2ccc(N3C[C@H](CNC(=O)c4ccc(Cl)s4)OC3=O)cc2C)c1=O] | LC-MS (method 6): R$_t$ = 1.44 min, MS (ESIpos): m/z = 561 (M + H)$^+$ $^1$H-NMR (400 MHz, DMSO-d$_6$, δ/ppm): 8.96 (t, 1H), 7.69 (d, 1H), 7.56-7.44 (m, 2H), 7.26-7.15 (m, 2H), 7.05 (d, 1H), 6.92 (d, 1H), 6.22 (t, 1H), 4.86 (m, 1H), 4.21 (dd, 1H), 3.97 (m, 2H), 3.88 (m, 1H), 3.61 (t, 2H), 3.38 (t, 2H), 3.22 (s, 3H), 2.88 (t, 2H), 2.72 (t, 2H), 2.02 (s, 3H). |
| 30 | 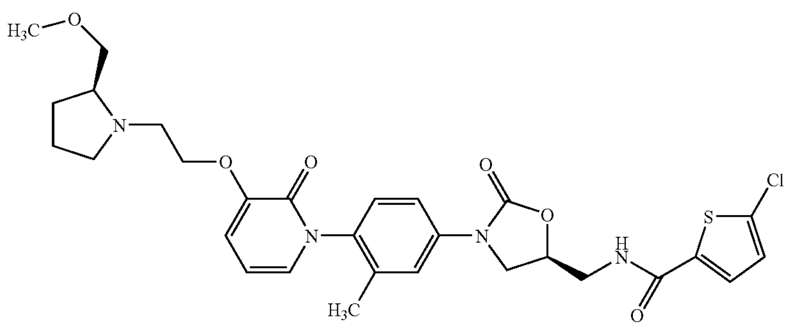 [SMILES: COC[C@@H]1CCCN1CCOc1cccn(-c2ccc(N3C[C@H](CNC(=O)c4ccc(Cl)s4)OC3=O)cc2C)c1=O] | LC-MS (method 11): R$_t$ = 2.14 min, MS (ESIpos): m/z = 601 (M + H)$^+$ $^1$H-NMR (400 MHz, DMSO-d$_6$, δ/ppm): 8.96 (t, 1H), 7.69 (d, 1H), 7.56-7.47 (m, 2H), 7.26-7.15 (m, 2H), 7.04 (d, 1H), 6.92 (d, 1H), 6.21 (t, 1H), 4.86 (m, 1H), 4.21 (dd, 1H), 4.07-3.83 (m, 3H), 3.61 (t, 2H), 3.38-3.13 (m, 5H: darin 3.26 (s, 3H)), 3.09 (m, 1H), 2.65 (m, 2H), 2.28 (m, 1H), 2.02 (s, 3H), 1.38-1.75 (m, 1H), 1.72-1.57 (m, 2H), 1.49-1.39 (m, 1H). |
| 31 | 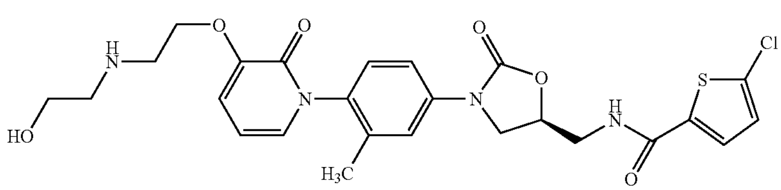 [SMILES: Cc1cc(N2C[C@H](CNC(=O)c3ccc(Cl)s3)OC2=O)ccc1-n1cccc(OCCNCCO)c1=O] | LC-MS (method 3): R$_t$ = 1.40 min, MS (ESIpos): m/z = 547 (M + H)$^+$ $^1$H-NMR (400 MHz, DMSO-d$_6$, δ/ppm): 8.98 (t, 1H), 7.70 (d, 1H), 7.55-7.46 (m, 2H), 7.25-7.17 (m, 2H), 7.05 (d, 1H), 6.97 (d, 1H), 6.24 (t, 1H), 4.86 (m, 1H), 4.61 (m, 1H), 4.22 (dd, 1H), 4.02 (m, 2H), 3.88 (m, 1H), 3.61 (t, 2H), 3.48 (m, 2H), 2.98 (m, 2H), 2.72 (t, 2H), 2.02 (s, 3H). |
| 32 | 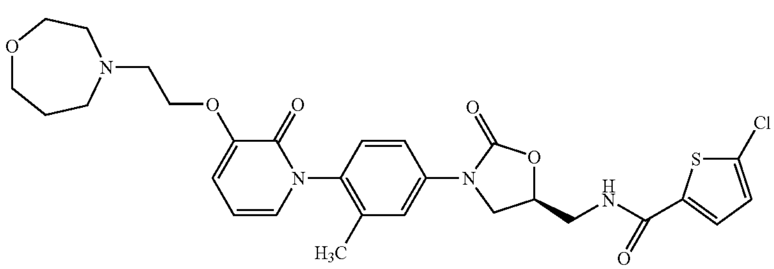 [SMILES: Cc1cc(N2C[C@H](CNC(=O)c3ccc(Cl)s3)OC2=O)ccc1-n1cccc(OCCN2CCCOCC2)c1=O] | LC-MS (method 3): R$_t$ = 1.33 min, MS (ESIpos): m/z = 587 (M + H)$^+$ $^1$H-NMR (400 MHz, DMSO-d$_6$, δ/ppm): 8.97 (t, 1H), 7.70 (d, 1H), 7.54-7.47 (m, 2H), 7.25-7.17 (m, 2H), 7.05 (d, 1H), 6.93 (d, 1H), 6.21 (t, 1H), 4.86 (m, 1H), 4.22 (dd, 1H), 4.02 (m, 2H), 3.70-3.57 (m, 6H), 2.89 (t, 2H), 2.75 (m, 4H), 2.02 (s, 3H), 1.78 (m, 2H). |

-continued

| Example | Structure | Characterization |
|---|---|---|
| 33 | 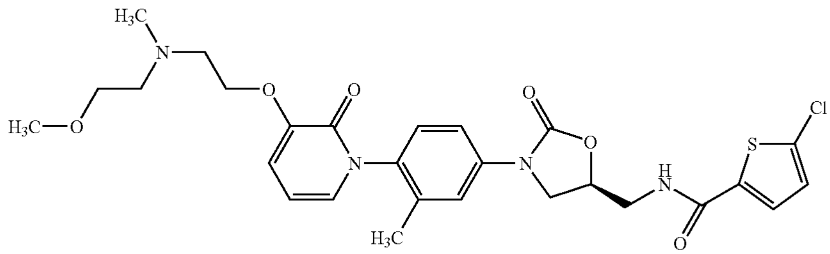 [SMILES: COCCN(C)CCOc1cccn(-c2ccc(N3C[C@H](CNC(=O)c4ccc(Cl)s4)OC3=O)cc2C)c1=O] | LC-MS (method 6): R$_t$ = 1.46 min, MS (ESIpos): m/z = 575 (M + H)$^+$ $^1$H-NMR (400 MHz, DMSO-d$_6$, δ/ppm). 8.96 (t, 1H), 7.69 (d, 1H), 7.55-7.46 (m, 2H), 7.25-7.17 (m, 2H), 7.05 (d, 1H), 6.93 (d, 1H), 6.21 (t, 1H), 4.86 (m, 1H), 4.22 (dd, 1H), 4.02 (m, 2H), 3.88 (m, 1H), 3.62 (t, 3H), 3.41 (t, 2H), 3.25 (s, 3H), 2.75 (m, 2H), 2.58 (t, 2H), 2.28 (s, 3H), 2.02 (s, 3H). |

Example 34

5-Chloro-N-{[(5S)-3-(4-{3-[2-(4-hydroxypiperidin-1-yl)ethoxy]-2-oxopyridin-1(2H)-yl}-3-methylphenyl)-2-oxo-1,3-oxazolidin-5-yl]methyl}thiophene-2-carboxamide

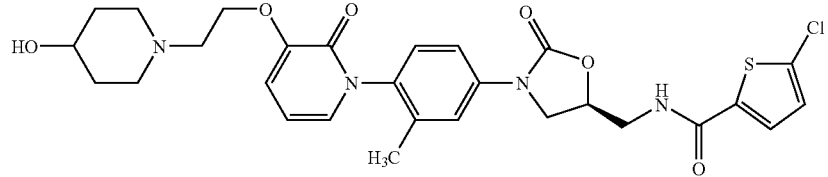 [SMILES: Cc1cc(N2C[C@H](CNC(=O)c3ccc(Cl)s3)OC2=O)ccc1-n1cccc(OCCN2CCC(O)CC2)c1=O]

88.0 mg (175 μmol) of Example 45A are dissolved in 5 ml of anhydrous dichloromethane and cooled to −78° C., and 42 μl (69.7 mg, 244 μmol) of trifluoromethanesulphonic anhydride and 56 mg (524 μmol) of 2,6-dimethylpyridine are added. After one hour of stirring at −78° C., another 15 μl (24.7 mg, 88 μmol) of trifluoromethanesulphonic anhydride are added dropwise, and the mixture is stirred at this temperature for another half an hour. At −78° C., 180 mg (1.74 mmol) of 4-hydroxypiperidine are then added to the reaction, and the mixture is stirred for 5 minutes, warmed to room temperature and stirred at this temperature overnight. For work-up, the reaction is concentrated on a rotary evaporator and the residue is purified twice by preparative RP-HPLC using an acetonitrile/water mixture. This gives 30.0 mg (29% of theory) of the desired product.

$^1$H-NMR (400 MHz, DMSO-d$_6$, δ/ppm): 8.96 (t, 1H), 8.15 (s, 1H), 7.69 (d, 1H), 7.55-7.46 (m, 2H), 7.25-7.15 (m, 2H), 7.04 (d, 1H), 6.93 (d, 1H), 6.21 (t, 1H), 4.86 (m, 1H), 4.22 (dd, 1H), 4.01 (m, 2H), 3.92-3.84 (m, 1H), 3.62 (t, 2H), 3.45 (m, 1H), 2.80 (m, 2H), 2.70 (t, 2H), 2.17 (m, 2H), 2.01 (s, 3H), 1.75-1.64 (m, 2H), 1.45-1.32 (m, 2H).

LC-MS (method 3): R$_t$=1.38 min
MS (ESIpos): m/z=587 (M+H)$^+$

Example 35

5-Chloro-N-{[(5S)-3-{4-[3-{2-[(trans-4-hydroxycyclohexyl)amino]ethoxy}-2-oxopyridin-1(2H)-yl]-3-propylphenyl}-2-oxo-1,3-oxazolidin-5-yl]methyl}thiophene-2-carboxamide

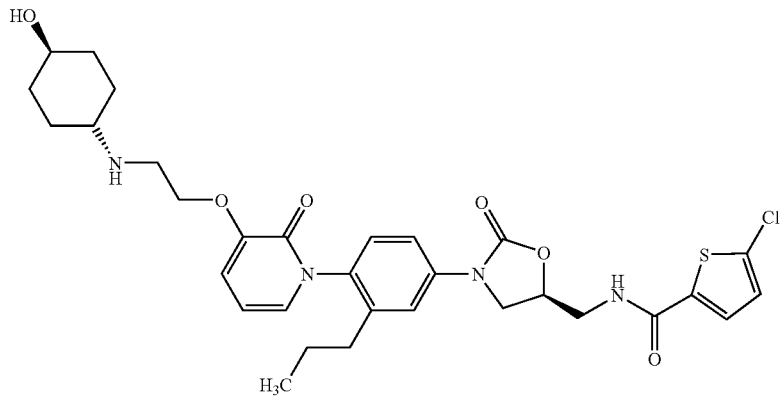

30 mg (54 µmol) of Example 58A, 8.2 mg (54 µmol) of sodium iodide and 31.4 mg (272 µmol) of trans-4-aminohexanol are initially charged in 750 µl of 1,2-dimethoxyethane. The reaction is stirred at 90° C. for 8 hours. For work-up, the reaction solution is concentrated completely on a rotary evaporator and subjected to fine purification by preparative RP-HPLC using an acetonitrile/water mixture. This gives 15.0 mg (41% of theory) of the product.

$^1$H-NMR (400 MHz, methanol-$d_4$, δ/ppm): 7.61 (dd, 1H), 7.52 (m, 2H), 7.20 (d, 1H), 7.07 (d, 2H), 7.01 (d, 1H), 6.92 (t, 1H), 6.42 (t, 1H), 4.27 (t, 1H), 4.08 (m, 2H), 3.98 (m, 1H), 3.73 (m, 2H), 3.58-3.45 (m, 1H), 3.02 (m, 2H), 2.50 (m, 1H), 2.35 (m, 2H), 1.97 (m, 4H), 1.50 (m, 2H), 1.38-1.11 (m, 5H), 0.83 (t, 3H).

LC-MS (method 8): $R_t$=2.06 min
MS (ESIpos): m/z=629 (M+H)$^+$

Example 36

5-Chloro-N-{[(5S)-3-{4-[3-{2-[(2-hydroxyethyl)amino]ethoxy}-2-oxopyridin-1(2H)-yl]-3-propylphenyl}-2-oxo-1,3-oxazolidin-5-yl]methyl}thiophene-2-carboxamide

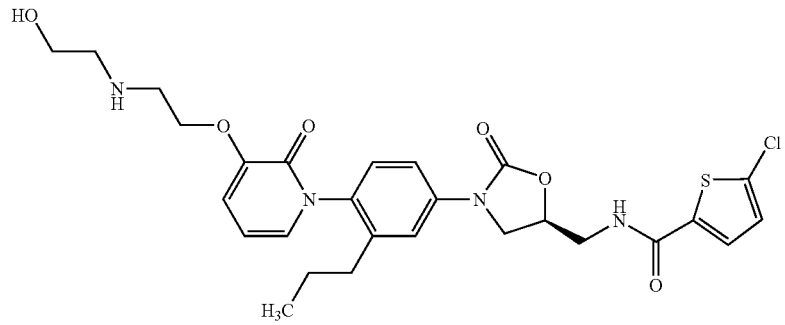 [SMILES: CCCc1cc(N2C[C@H](CNC(=O)c3ccc(Cl)s3)OC2=O)ccc1-n1cccc(OCCNCCO)c1=O]

500 mg (0.908 mmol) of Example 58A, 142 mg (0.954 mmol) of sodium iodide and 277 mg (4.54 mmol) of 2-aminoethanol are dissolved in 8 ml of 1,2-dimethoxyethane and stirred at 90° C. for 4 hours. The reaction solution is concentrated and then taken up in 100 ml of dichloromethane and water and stirred at RT for 1 h. The phases are separated, and the aqueous phase is extracted with dichloromethane. The combined organic phases are washed with saturated sodium chloride solution and then dried over sodium sulphate. The drying agent is filtered off, and the solvent is removed completely on a rotary evaporator. The residue is purified by chromatography on silica gel (dichloromethane/ethanol 5:1; addition of 0.1% by volume of ethyldimethylamine). This gives 241 mg (46% of theory) of the desired product.

$^1$H-NMR (400 MHz, DMSO-$d_6$, δ/ppm): δ=9.01 (t, 1H), 7.70 (d, 1H), 7.58-7.45 (m, 2H), 7.23-7.17 (m, 2H), 7.06 (dd, 1H), 6.95 (dd, 1H), 6.22 (dd, 1H), 4.91-4.82 (m, 1H), 4.65-4.55 (m, 1H), 4.24 (dd, 1H), 4.10-3.85 (m, 3H), 3.62 (dd, 2H), 3.52-3.43 (m, 2H), 2.93 (t, 2H), 2.68 (t, 2H), 2.35-2.20 (m, 2H), 1.50-1.35 (m, 2H), 0.78 (t, 3H).

HPLC (method 2): $R_t$=4.00 min
MS (ESIpos): m/z=575 (M+H)$^+$

Example 37

5-Chloro-N-{[(5S)-3-{4-[3-{2-[(2-hydroxyethyl)amino]ethyl}-2-oxopyridin-1(2H)-yl]-3,5-dimethylphenyl}-2-oxo-1,3-oxazolidin-5-yl]methyl}thiophene-2-carboxamide

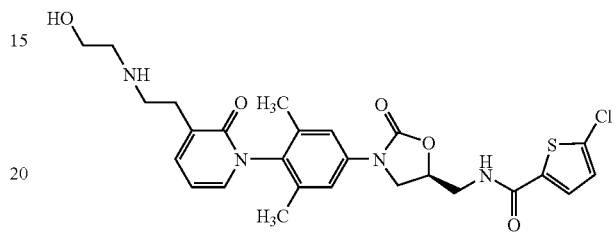

100 mg (0.20 mmol) of Example 65A are dissolved in 3 ml of anhydrous dichloromethane and cooled to −78° C., and 64 mg (0.59 mmol) of 2,6-dimethylpyridine and 84 mg (0.29 mmol) of trifluoromethanesulphonic anhydride are added. After 1 h at −78° C., 121 mg (1.99 mmol) of 2-aminoethanol are added, cooling is removed after 5 min and the mixture is stirred at room temperature for 18 h. The solvent is then removed under reduced pressure and the residue is purified twice by preparative HPLC using a gradient of acetonitrile and 0.3% strength formic acid in water. This gives 27 mg (25% of theory) of the desired compound.

$^1$H-NMR (400 MHz, DMSO-$d_6$, δ/ppm): δ=9.01 (t, 1H), 8.30 (s, 1H), 7.70 (d, 1H), 7.46 (d, 1H), 7.41-7.34 (m, 2H), 7.31 (d, 1H), 7.19 (d, 1H), 6.33 (dd, 1H), 4.91-4.82 (m, 1H), 4.20 (dd, 1H), 3.86 (dd, 1H), 3.61 (t, 2H), 3.54 (t, 2H), 2.94 (t, 2H), 2.81 (t, 2H), 2.72 (t, 2H), 1.96 (s, 6H).

LC-MS (method 12): $R_t$=1.22 min
MS (ESIpos): m/z=545 (M+H)$^+$

Example 38

5-Chloro-N-{[(5S)-3-{4-[3-{2-[(trans-4-hydroxycyclohexyl)amino]ethyl}-2-oxopyridin-1(2H)-yl]-3,5-dimethylphenyl}-2-oxo-1,3-oxazolidin-5-yl]methyl}thiophene-2-carboxamide

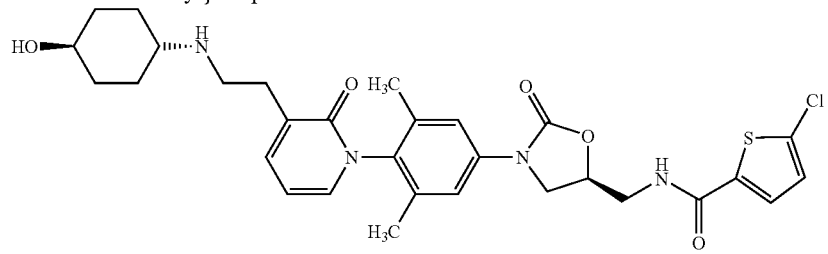

100 mg (0.20 mmol) of Example 65A are dissolved in 3 ml of anhydrous dichloromethane and cooled to −78° C., and 64 mg (0.59 mmol) of 2,6-dimethylpyridine and 84 mg (0.29 mmol) of trifluoromethanesulphonic anhydride are added. After 1 h at −78° C., 114 mg (0.97 mmol) of trans-4-aminohexanol are added, cooling is removed after 5 min and the mixture is stirred at room temperature for 18 h. The solvent is then removed under reduced pressure and the residue is purified twice by preparative HPLC using a gradient of acetonitrile and 0.3% strength formic acid in water. This gives 15 mg (13% of theory) of the desired compound.

$^1$H-NMR (400 MHz, DMSO-$d_6$, δ/ppm): δ=9.00 (t, 1H), 8.28 (s, 1H), 7.70 (d, 1H), 7.51-7.42 (m, 1H), 7.41-7.34 (m, 2H), 7.31 (d, 1H), 7.19 (d, 1H), 6.33 (dd, 1H), 4.91-4.82 (m, 1H), 4.20 (t, 1H), 3.86 (dd, 1H), 3.64-3.55 (m, 2H), 3.52 (dd, 1H), 3.38-3.29 (m, 2H), 2.95-2.86 (m, 2H), 2.78 (dd, 1H), 2.74-2.60 (m, 3H), 1.96 (s, 6H), 1.94-1.75 (m, 2H), 1.20-1.10 (m, 3H). The spectrum contains signals of formic acid and/or the formate of the title compound.

LC-MS (method 12): $R_t$=1.24 min
MS (ESIpos): m/z=599 (M+H)$^+$

Alternative Synthesis 1:

600 mg (1.19 mmol) of Example 65A are dissolved in 18 ml of anhydrous dichloromethane and cooled to −78° C., and 384 mg (3.58 mmol) of 2,6-dimethylpyridine and 573 mg (2.03 mmol) of trifluoromethanesulphonic anhydride are added. After 1 h at −78° C., 688 mg (5.97 mmol) of trans-4-aminohexanol are added, cooling is removed after 5 min and the mixture is stirred at room temperature for 18 h. The solvent is then removed under reduced pressure and the residue is purified by preparative HPLC using a 1:1 mixture of acetonitrile/0.1% strength diisopropylethylamine in water. This gives 263 mg (36% of theory) of the desired compound.

$^1$H-NMR (400 MHz, DMSO-$d_6$, δ/ppm): δ=8.98 (t, 1H), 7.70 (d, 1H), 7.48-7.33 (m, 3H), 7.25 (d, 1H), 7.19 (d, 1H), 6.28 (dd, 1H), 4.91-4.82 (m, 1H), 4.44 (d, 1H), 4.20 (t, 1H), 3.86 (dd, 1H), 3.64-3.55 (m, 2H), 2.72 (dd, 2H), 2.64-2.50 (m, 3H), 2.35-2.23 (m, 1H), 1.96 (s, 6H), 1.82-1.71 (m, 4H), 1.20-0.89 (m, 4H).

LC-MS (method 14): $R_t$=0.83 min
MS (ESIpos): m/z=599 (M+H)$^+$

Alternative Synthesis 2:

39 g (77 mmol) of Example 65A (alternative synthesis) are dissolved in 1.17 l of anhydrous dichloromethane and cooled to below −60° C. First, 24.9 g (233 mmol) of 2,6-dimethylpyridine are added, and 22.3 ml (132 mmol) of trifluoromethanesulphonic anhydride are then added dropwise. After 15 min at −70° C., a solution of 46.1 g (388 mmol) of trans-4-aminohexanol in 360 ml of dichloromethane and 360 ml of isopropanol is then added quickly at below −50° C. The mixture is stirred in a dry-ice bath for 15 min, and the cooling bath is then removed. After 3 h, the solvent is removed under reduced pressure and the residue is purified by chromatography on silica gel (dichloromethane/methanol/25% strength ammonia solution 9:1:0.2). The product-containing fractions are combined, freed from the solvent and re-purified by chromatography on silica gel (dichloromethane/methanol/25% strength ammonia solution 9:1:0.2). The product-containing fractions are combined and freed from the solvent under reduced pressure. To remove any methanol still present, twice, in each case 130 ml of water are added and the solvent is then removed at 50° C. under reduced pressure, and the product is dried under high vacuum. This gives 34.1 g (73% of theory) of the desired product.

$^1$H-NMR (400 MHz, DMSO-$d_6$, δ/ppm): δ=8.98 (t, 1H), 7.70 (d, 1H), 7.48-7.33 (m, 3H), 7.25 (d, 1H), 7.19 (d, 1H), 6.28 (dd, 1H), 4.91-4.82 (m, 1H), 4.44 (d, 1H), 4.20 (t, 1H), 3.86 (dd, 1H), 3.64-3.55 (m, 2H), 2.72 (dd, 2H), 2.64-2.50 (m, 3H), 2.35-2.23 (m, 1H), 1.96 (s, 6H), 1.82-1.71 (m, 4H), 1.20-0.89 (m, 4H).

Example 39

5-Chloro-N-{[(5S)-3-{4-[3-{2-[(trans-4-hydroxycyclohexyl)amino]ethoxy}-2-oxopyridin-1(2H)-yl]-3,5-dimethylphenyl}-2-oxo-1,3-oxazolidin-5-yl]methyl}thiophene-2-carboxamide

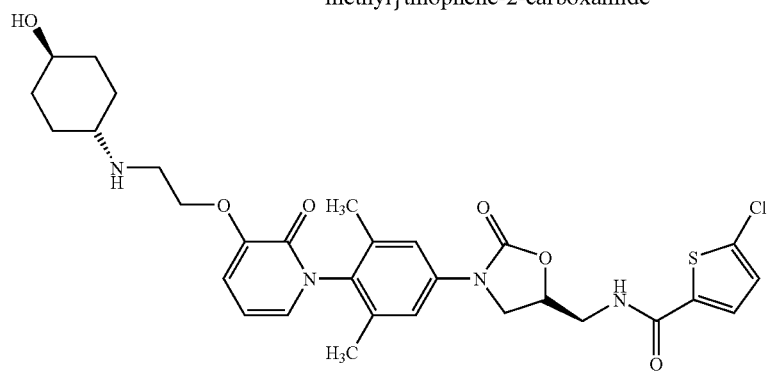

211 mg (0.393 mmol) of Example 73A, 62 mg (0.41 mmol) of sodium iodide and 226 mg (1.97 mmol) of trans-4-aminohexanol are initially charged in 3.5 ml of 1,2-dimethoxyethane. The reaction is stirred at 90° C. for 15 hours. For work-up, the reaction solution is concentrated completely in a rotary evaporator and then taken up in a dichloromethane/water mixture and stirred at RT for 10 min. After phase separation, the aqueous phase is extracted with dichloromethane. The combined organic phases are washed with a saturated aqueous sodium chloride solution. After drying over sodium sulphate, the drying agent is filtered off and the solvent is removed completely on a rotary evaporator. The residue is pre-purified by chromatography on silica gel (dichloromethane/ethanol 10:1, addition of 1% ethyldimethylamine). Subsequent purification by preparative HPLC using an acetonitrile/water mixture gives 104 mg (43% of theory) of the desired product.

$^1$H-NMR (400 MHz, DMSO-d$_6$, δ/ppm): δ=8.99 (t, 1H), 7.61 (dd, 1H), 7.43-7.36 (m, 2H), 7.20 (d, 1H), 7.15-7.07 (m, 2H), 6.34 (t, 1H), 4.88-4.80 (m, 1H), 4.23-4.15 (m, 3H), 3.92-3.65 (m, 1H), 3.61 (dd, 4H), 3.40-3.31 (m, 3H), 3.13-3.03 (m, 1H), 2.07-1.95 (m, 2H), 1.96 (s, 6H), 1.88-1.80 (m, 2H), 1.41-130 (m, 2H), 1.23-1.12 (m, 2H).

HPLC (method 2): R$_t$=3.84 min

MS (ESIpos): m/z=615 (M+H)$^+$

Example 40

5-Chloro-N-{[(5S)-3-{4-[3-{2-[(2-hydroxyethyl)amino]ethoxy}-2-oxopyridin-1(2H)-yl]-3,5-dimethylphenyl}-2-oxo-1,3-oxazolidin-5-yl]methyl}thiophene-2-carboxamide

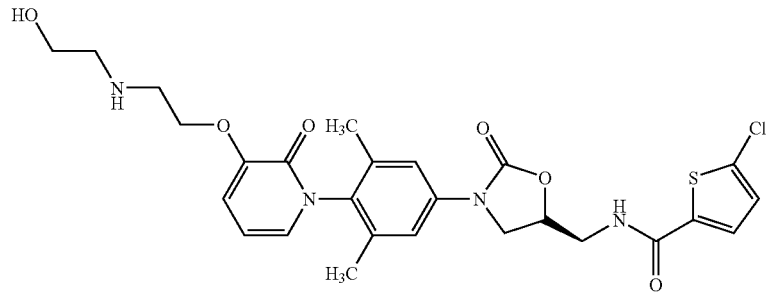

255 mg (0.475 mmol) of Example 73A, 74 mg (0.50 mmol) sodium iodide and 145 mg (2.38 mmol) of 2-aminoethanol are dissolved in 4.2 ml of 1,2-dimethoxyethane and stirred at 90° C. for 15 hours. For work-up, the reaction solution is concentrated completely on a rotary evaporator and the residue is taken up in 100 ml of a dichloromethane/water mixture and stirred at RT for 10 min. After phase separation, the aqueous phase is extracted with dichloromethane. The combined organic phases are washed with a saturated aqueous sodium chloride solution. After drying over sodium sulphate, the drying agent is filtered off and the solvent is removed completely on a rotary evaporator. The residue is purified by chromatography on silica gel (dichloromethane/ethanol 10:1->5:1, addition of 1% ethyldimethylamine). This gives 168 mg (58% of theory) of the desired product.

$^1$H-NMR (400 MHz, DMSO-d$_6$, δ/ppm): δ=9.07 (t, 1H), 7.78-7.72 (m, 1H), 7.41-7.35 (m, 2H), 7.20 (d, 1H), 7.08-7.02 (m, 2H), 6.31 (dd, 1H), 4.92-4.81 (m, 1H), 4.22-4.12 (m, 2H), 3.92-3.86 (dd, 1H), 3.63-3.56 (m, 4H), 3.40-3.27 (m, 3H), 3.23-3.17 (m, 2H), 2.97-2.92 (m, 2H), 1.96 (s, 6H).

HPLC (method 2): R$_t$=3.80 min

MS (ESIpos): m/z=561 (M+H)$^+$

B. Evaluation Of the Pharmacological Activity

The suitability of the compounds according to the invention for treating thromboembolic disorders can be demonstrated using the following assay systems:

a) Test Descriptions (In Vitro)

a.1) Measurement of the Factor Xa Inhibition in Buffer

To determine the factor Xa inhibition of the substances listed above, a biological test system is constructed in which the conversion of a factor Xa substrate is used for determining the enzymatic activity of human factor Xa. Here, factor Xa cleaves aminomethylcoumarin, which is measured fluorescently, from the peptidic substrate. The determinations are carried out in microtitre plates.

Substances to be tested are dissolved in various concentrations in dimethyl sulphoxide and incubated for 30 min with human factor Xa (1.3 nmol/l dissolved in 50 mmol/l of Tris buffer [C,C,C-tris(hydroxymethyl)aminomethane], 100 mmol/l of sodium chloride, 5 mmol/l of calcium chloride, 0.1% BSA [bovine serum albumin], pH 7.4) at 22° C. The substrate (5 μmol/l Boc-Ile-Glu-Gly-Arg-AMC from Bachem) is then added. After 30 min of incubation, the sample is excited at a wavelength of 360 nm and the emission is measured at 460 nm. The measured emissions of the test batches with test substance are compared to the control batches without test substance (only dimethyl sulphoxide instead of test substance in dimethyl sulphoxide) and the IC$_{50}$ values are calculated from the concentration/activity relationships.

a.2) Measurement of Thrombin Inhibition in Buffer

To determine the thrombin inhibition of the substances listed above, a biological test system is constructed in which the conversion of a thrombin substrate is used for determining the enzymatic activity of human thrombin. Here, thrombin cleaves aminomethylcoumarin, which is measured fluorescently, from the peptidic substrate. The determinations are carried out in microtitre plates.

Substances to be tested are dissolved in various concentrations in dimethyl sulphoxide and incubated for 15 min with human thrombin (0.06 nmol/l dissolved in 50 mmol/l of Tris buffer [C,C,C-tris(hydroxymethyl)aminomethane], 100 mmol/l of sodium chloride, 0.1% BSA [bovine serum albumin], pH 7.4) at 22° C. The substrate (5 μmol/l Boc-Asp (OBzl)-Pro-Arg-AMC from Bachem) is then added. After 30 min of incubation, the sample is excited at a wavelength of 360 nm and the emission is measured at 460 nm. The measured emissions of the test batches with test substance are compared to the control batches without test substance (only dimethyl sulphoxide instead of test substance in dimethyl sulphoxide) and the IC$_{50}$ values are calculated from the concentration/activity relationships.

a.3) Determination of the Selectivity

To demonstrate the selectivity of the substances with respect to thrombin and factor Xa inhibition, the test substances are examined for their inhibition of other human serine proteases, such as factor XIIa, factor XIa, trypsin and plasmin. To determine the enzymatic activity of factor XIIa (10 nmol/l from Kordia), factor XIa (0.4 nmol/l from Kordia), trypsin (83 mU/ml from Sigma) and plasmin (0.1 µg/ml from Kordia), these enzymes are dissolved (50 mmol/l of Tris buffer [C,C,C-tris(hydroxymethyl)aminomethane], 100 mmol/l of sodium chloride, 0.1% BSA [bovine serum albumin], 5 mmol/l of calcium chloride, pH 7.4) and incubated for 15 min with test substance in various concentrations in dimethyl sulphoxide and also with dimethyl sulphoxide without test substance. The enzymatic reaction is then started by addition of the appropriate substrates (5 µmol/l of H-Pro-Phe-Arg-AMC from Bachem for factor XIIa, 5 µmol/l of Boc-Ile-Glu-Gly-Arg-AMC from Bachem for Trypsin, 5 µmol/l of Boc-Glu(OBzl)-Ala-Arg-AMC from Bachem for factor XIa, 50 µmol/l of MeOSuc-Ala-Phe-Lys-AMC from Bachem for plasmin). After an incubation time of 30 min at 22° C., fluorescence is measured (excitation: 360 nm, emission: 460 nm). The measured emissions of the test batches with test substance are compared to the control batches without test substance (only dimethyl sulphoxide instead of test substance in dimethyl sulphoxide), and the $IC_{50}$ values are calculated from the concentration/activity relationships.

a.4) Determination of the Factor Xa-inhibitory Activity of the Potential Inhibitors in Plasma Samples To determine the inhibition of factor Xa in plasma samples, the factor X present in plasma is activated by a protease from rattlesnake toxin. The factor Xa activity or its inhibition by potential inhibitors is then measured by addition of a chromogenic substrate.

Various concentrations of the substances to be tested are dissolved in dimethyl sulphoxide and mixed with an aqueous refludan solution (10 µg/ml). In clear 96-well plates having a flat bottom, 30 µl of citrate plasma (Octapharma) are mixed with 10 µl of the substance dilution. Then, either 20 µl of a solution of a rattlesnake toxin (Russel viper venom (RVV); RVV reagent: Pentapharm 121-06, final concentration 0.6 mU) in an aqueous calcium chloride solution buffer (final concentration of calcium chloride 0.05 M) or 20 µl of the aqueous calcium chloride solution (final concentration of calcium chloride 0.05 M) without RVV reagent (as reference for an unstimulated sample) are added. After addition of 20 µl of ChromozymX substrate (final concentration 1.6 mmol/l, Bachem L-1565, diluted in water) the samples are measured in a SpectraFluor Reader using a measurement filter of 405 nm each minute over a period of 20 minutes. The $IC_{50}$ value is determined when about 70% of the maximum signal is reached (about 12 min).

Representative activity data from this test are listed in Table 1 below:

TABLE 1

| Example No. | $IC_{50}$ [nM] |
| --- | --- |
| 6 | 31 |
| 9 | 11 |
| 10 | 15 |
| 13 | 17 |
| 16 | 18 |
| 21 | 11 |

TABLE 1-continued

| Example No. | $IC_{50}$ [nM] |
| --- | --- |
| 36 | 29 |
| 37 | 29 |
| 38 | 34 | a.5) Determination of the Thrombin-inhibitory Activity of the Potential Inhibitors in Plasma Samples Various concentrations of the substances to be tested are dissolved in dimethyl sulphoxide and diluted with water. In white 96-well plates having a flat bottom, 20 µl of substance dilution are mixed with 20 µl of ecarin solution (ecarin reagent, from Sigma E-0504, final concentration 20 mU per batch) in Ca buffer (200 mM Hepes+560 mM sodium chloride+10 mM calcium chloride+0.4% PEG) or with 20 µl of Ca buffer (as unstimulated control). Furthermore, 20 µl of fluorogenic thrombin substrate (from Bachem I-1120, final concentration 50 µmol/l) and 20 µl of citrate plasma (from Octapharma) are added and homogenized thoroughly. The plate is measured in a SpectraFluorplus Reader using an excitation filter of 360 nm and an emission filter of 465 nm each minute over a period of 20 minutes. The $IC_{50}$ value is determined when about 70% of the maximum signal is reached (about 12 min).

Representative activity data from this test are listed in Table 2 below:

TABLE 2

| Example No. | $IC_{50}$ [nM] |
| --- | --- |
| 6 | 143 |
| 9 | 10 |
| 10 | 24 |
| 13 | 16 |
| 16 | 10 |
| 21 | 34 |
| 36 | 36 |
| 37 | 15 |
| 38 | 30 | a.6) Thrombin Generation Assay (Thrombogram)

The effect of the test substances on the thrombogram (thrombin generation assay according to Hemker) is determined in vitro in human plasma (Octaplas® from Octapharma). In the thrombin generation assay according to Hemker, the activity of thrombin in coagulating plasma is determined by measuring the fluorescent cleavage products of the substrate I-1140 (Z-Gly-Gly-Arg-AMC, Bachem). Reagents from Thrombinoscope (PPP reagent: 30 µM recombinant tissue factor, 24 µM phospholipids in HEPES) are used to start the coagulation reaction. The reaction is carried out in the presence of varying concentrations of test substance or the corresponding solvent. Moreover, a thrombin calibrator from Thrombinoscope is used whose amidolytic activity is required for calculating the thrombin activity in a plasma sample.

The test is carried out according to the specifications of the manufacturer (Thrombinoscope BV): 4 µl of the test substance or of the solvent, 76 µl of plasma and 20 µl of PPP reagent or thrombin calibrator are incubated at 37° C. for 5 min. After addition of 20 µl of 2.5 mM thrombin substrate in 20 mM Hepes, 60 mg/ml of BSA, 102 mM calcium chloride, the thrombin generation is measured every 20 s over a period of 120 min. Measurement is carried out using a fluorometer (Fluoroskan Ascent) from Thermo Electron fitted with a 390/

460 nm filter pair and a dispenser. Using the Thrombinoscope software, the thrombogram is calculated and presented graphically. What is calculated are the following parameters: lag time, time to peak, peak, ETP (endogenous thrombin potential) and start tail.

a.7) Determination of the Anticoagulatory Activity

The anticoagulatory activity of the test substances is determined in vitro in human plasma, rabbit plasma and rat plasma. To this end, blood is drawn off in a mixing ratio of sodium citrate/blood of 1/9 using a 0.11 molar sodium citrate solution as receiver. Immediately after the blood has been drawn off, it is mixed thoroughly and centrifuged at about 4000 g for 15 minutes. The supernatant is pipetted off.

The prothrombin time (PT, synonyms: thromboplastin time, quick test) is determined in the presence of varying concentrations of test substance or the corresponding solvent using a commercial test kit (Neoplastin® from Boehringer Mannheim or Hemoliance® RecombiPlastin from Instrumentation Laboratory). The test compounds are incubated with the plasma at 37° C. for 3 minutes. Coagulation is then started by addition of thromboplastin, and the time when coagulation occurs is determined. The concentration of test substance which effected a doubling of the prothrombin time is determined.

The thrombin time (TT) is determined in the presence of varying concentrations of test substance or the corresponding solvent using a commercial test kit (thrombin reagent from Roche). The test compounds are incubated with the plasma at 37° C. for 3 minutes. Coagulation is then started by addition of the thrombin reagent, and the time when coagulation occurs is determined. The concentration of test substance which effects a doubling of the thrombin time is determined.

The activated partial thromboplastin time (APTT) is determined in the presence of varying concentrations of test substance or the corresponding solvent using a commercial test kit (PTT reagent from Roche). The test compounds are incubated with the plasma and the PTT reagent (cephalin, kaolin) at 37° C. for 3 minutes. Coagulation is then started by addition of 25 mM calcium chloride, and the time when coagulation occurs is determined. The concentration of test substance which effects a doubling of the APTT is determined.

a.8) Thromboelastography (Thromboelastogram)

The thromboelastography is carried out with the aid of the thromboelastograph ROTEM from Pentapharm and its accessories, cup and pin. The measurement is carried out in whole blood drawn off beforehand into sodium citrate monovettes from Sarstedt. The blood in the monovettes is kept in motion using a shaker and preincubated at 37° C. for 30 min. A 2 molar stock solution of calcium chloride in water is prepared. This is diluted 1:10 with an aqueous 0.9% strength sodium chloride solution. For the measurement, 20 µl of this 200 mM calcium chloride solution are initially charged into the cups (final concentration of calcium chloride 12.5 mM). 3.2 µl of substance or solvent are added. The measurement is started by addition of 300 µl of whole blood. After the addition, using the tip of the pipette, the mixture is briefly drawn into the pipette and released again without generating air bubbles. The measurement is carried out over a period of 2.5 hours or is stopped when fibrinolysis sets in. For evaluation, the following parameters are determined: CT (clotting time/[sec.]), CFT (clotting formation time/[sec.]), MCF (maximum clot firmness/[mm]) and the alpha angle [°]. The measurement points are determined every 3 seconds and represented graphically, with the y axis for MCF [mm] and the x axis for time [sec.].

a.9) Inhibition of the Thrombus-bound Coagulation Factors Thrombin and Factor Xa Blood clots formed either prior to initiation of therapy with anticoagulants, during therapy breaks or in spite of therapy contain large amounts of coagulation factors which may favour the progressing thrombus formation. These coagulation factors are bound firmly to the thrombus and cannot be washed out. In certain clinical situations, this may result in a risk for the patient. In the tests carried out below, both thrombin and factor Xa having biological (procoagulatory) activity can be demonstrated in human thrombi.

Thrombi Formed In Vitro

Thrombi are formed in vitro from human plasma and examined for the activity of the bound coagulation factors thrombin and factor Xa. To this end, 300 µl of plasma are mixed with 30 µl of lipid vesicles and 30 µl of an aqueous calcium chloride solution in a 48-well MTP plate and incubated for 30 min. This and the following steps are carried out at 37° C. and with constant agitation (300 rpm). The thrombi formed are transferred into a new 48-well MTP plate and washed twice with 0.9% strength sodium chloride solution over a period of 10 min, the thrombus being dabbed on filter paper during the washing steps. The thrombus is transferred into buffer B (Owens Veronal Buffer, 1% BSA) and incubated for 15 min, dabbed on filter paper and incubated in test substance of various concentrations in buffer B for 30 min. The clots are then washed twice as described above. The thrombi are dabbed and transferred into buffer D: (240 µl Owren's Veronal Buffer, 1% BSA and 15.6 mM calcium chloride) and incubated with or without 0.6 µM prothrombin for 45 min. The reaction is stopped by addition of 75 µl of a 1% EDTA solution. The thrombin activity is measured separately in the thrombus in buffer A (7.5 mM $Na_2EDTA \times 2H_2O$, 175 mM sodium chloride, 1% BSA, pH 8.4) or in the supernatant from the last step. To this end, the substrate I-1120 in used in a final concentration of 50 µM, and the resulting fluorescence is measured in a fluorescence plate reader (360/465 nm).

The activity of this thrombus-bound thrombin cannot be suppressed by a selective factor Xa inhibitor in therapeutically relevant concentrations. In contrast, it can be inhibited with dual factor IIa/factor Xa inhibitors or a factor IIa reference inhibitor.

After addition of prothrombin, if thrombus-bound factor Xa is present (prothrombinase complex), new thrombin is formed which is detected by the fluorescent substrate. This renewed formation of thrombin cannot be prevented by a pure thrombin inhibitor; however, it can be inhibited by dual factor IIa/factor Xa inhibitors or by the selective factor Xa reference inhibitor.

The biological activity of the thrombus-bound thrombin activity is tested by adding fluorescently labelled fibrinogen which, by active thrombin, is converted into fibrin and bound to the thrombus. To this end, the thrombus is formed as described above and incubated in 250 µl of a fibrinogen solution (100 µg/ml) labelled with Alexa488 and 30 µl of an aqueous 100 mM calcium chloride solution (with or without various concentrations of test substances). The fluorescence of the supernatant is measured in a fluorescence plate reader at a suitable wavelength. Moreover, the thrombi are washed four times with in each case 15 min and evaluated by fluorescence microscopy. The decrease of the fluorescence from the supernatant and the increase of the fluorescence of the thrombi can be inhibited by dual factor IIa/factor Xa inhibitors, but not by the factor Xa reference inhibitor.

Intracardial Thrombi Formed In Vivo (Patient Material)

The experiments are repeated with thrombi taken from the left ventricle of patients during heart surgery. To this end, the thrombi were thawed and divided into pieces (wet weight 10-100 mg). Depending on the protocol, the thrombi are used after repeated washing or without washing, and the thrombin activity is measured analogously to the method described above using the substrate I-1120 (final concentration 100 µM).

a.10) Specific Diagnosis of Impaired Coagulation and Organ Function in Endotoxaemic Mice and Rats Thrombin/Antithrombin Complexes Thrombin/antithrombin complexes (hereinbelow referred to as "TAT") are a measure for the thrombin formed endogenously by coagulation activation. TAT are determined using an ELISA assay (Enzygnost TAT micro, Dade-Behring). Plasma is obtained from citrate blood by centrifugation. 50 µl of TAT sample buffer are added to 50 µl of plasma, and the sample is shaken briefly and incubated at room temperature for 15 min. The samples are filtered off with suction, and the well is washed 3 times with wash buffer (300 µl/well). During the washings, the liquid is removed by tapping the plate. Conjugate solution (100 µl) is added, and the plate is incubated at room temperature for 15 min. The samples are sucked off, and the well is washed 3 times with wash buffer (300 µl/well). Chromogenic substrate (100 µl/well) is then added, the plate is incubated in the dark at room temperature for 30 min, stop solution is added (100 µl/well) and the colour development is measured at 492 nm (Saphire plate reader).

Parameters for Organ Function

Various parameters are determined who allow conclusions to be drawn with respect to a restriction of the function of various internal organs by administration of LPS and which allow the therapeutic effect of test substances to be estimated. Citrate blood or, if appropriate, lithium/heparin blood is centrifuged, and the parameters are determined from the plasma. Typically, the following parameters are determined: creatinin, urea, aspartate aminotransferase (AST), alanine aminotransferase (ALT), total bilirubin, lactate dehydrogenase (LDH), total protein, total albumin and fibrinogen. The values give indications concerning the function of the kidneys, the liver, the cardiovascular system and the blood vessels.

Parameters for Inflammation

The extent of the inflammatory reaction triggered by endotoxin can be detected by the increase of inflammation mediators, for example interleukins (1, 6, 8 and 10), tumour necrosis factor alpha or monocyte chemoattractant protein-1 in the plasma. To this end, ELISAs or the luminex system may be used.

b) Determination of the Antithrombotic Activity (In Vivo)

b.1) Arteriovenous Shunt and Haemorrhage Model (Combi-model Rat)

Fasting male rats (strain: HSD CPB:WU) having a weight of 300-350 g are anaesthetized using Inactin (150-180 mg/kg). Thrombus formation is initiated in an arteriovenous shunt in accordance with the method described by Christopher N. Berry et al., Br. J. Pharmacol. (1994), 113, 1209-1214. To this end, the left jugular vein and the right carotid artery are exposed. The two vessels are connected by an extracorporeal shunt using a polyethylene tube (PE 60) of a length of 10 cm. In the middle, this polyethylene tube is attached to a further polyethylene tube (PE 160) of a length of 3 cm which contains a roughened nylon thread arranged to form a loop, to form a thrombogenic surface. The extracorporeal circulation is maintained for 15 minutes. The shunt is then removed and the nylon thread with the thrombus is weighed immediately. The weight of the nylon thread on its own is determined before the experiment is started.

To determine the bleeding time, immediately after opening of the shunt circulation, the tip of the tail of the rats is docked by 3 mm using a razor blade. The tail is then placed into physiological saline kept at a temperature of 37° C., and the bleeding from the cut is observed over a period of 15 min. What is determined are the time until bleeding ceases for at least 30 seconds (initial bleeding time), total bleeding time over a period of 15 minutes (cumulative bleeding time) and the quantitative blood loss via photometric determination of the collected haemoglobin.

Before the extracorporeal circulation is set up and the tip of the tail is docked, the test substances are administered to the animals while awake either intravenously via the contralateral jugular vein as a single bolus or as a bolus with subsequent continuous infusion or orally using a pharyngeal tube.

c) Solubility Assay

Reagents Required:

PBS buffer pH 7.4: 90.00 g of NaCl p.a. (for example Merck Art. No. 1.06404.1000), 13.61 g of $KH_2PO_4$ p.a. (for example Merck Art. No. 1.04873.1000) and 83.35 g of 1N NaOH (for example Bernd Kraft GmbH Art. No. 01030.4000) are weighed into a 1 l measuring flask, the flask is filled with water and the mixture is stirred for about 1 hour.

Acetate buffer pH 4.6: 5.4 g of sodium acetate×$3H_2O$ p.a. (for example Merck Art. No. 1.06267.0500) are weighed into a 100 ml measuring flask and dissolved in 50 ml of water, 2.4 g of glacial acetic acid are added, the mixture is made up to 100 ml with water, the pH is checked and, if required, adjusted to pH 4.6.

Dimethyl sulphoxide (for example Baker Art. No. 7157.2500)

Destilled water

Preparation of the Calibration Solutions:

Preparation of the stock solution for calibration solutions: About 0.5 mg of the active compound are weighed accurately into a 2 ml Eppendorf Safe-Lock tube (Eppendorf Art. No. 0030 120.094), DMSO is added to a concentration of 600 µg/ml (for example 0.5 mg of active compound+833 µl of DMSO) and the mixture is vortexed until everything has gone into solution.

Calibration solution 1 (20 µg/ml): 1000 µl of DMSO are added to 34.4 µl of the stock solution, and the mixture is homogenized.

Calibration solution 2 (2.5 µg/ml): 700 µl of DMSO are added to 100 µl of calibration solution 1, and the mixture is homogenized.

Preparation of the Sample Solutions:

Sample solution for solubilities of up to 10 g/l in PBS buffer pH 7.4: About 5 mg of the active compound are weighed accurately into a 2 ml Eppendorf Safe-Lock tube (Eppendorf Art. No. 0030 120.094), and PBS buffer pH 7.4 is added to a concentration of 5 g/l (for example 5 mg of active compound+500 µl of PBS buffer pH 7.4).

Sample solution for solubilities of up to 10 g/l in acetate buffer pH 4.6: About 5 mg of the active compound are weighed accurately into a 2 ml Eppendorf Safe-Lock tube (Eppendorf Art. No. 0030 120.094), and acetate buffer pH 4.6 is added to a concentration of 5 g/l (for example 5 mg of active compound+500 µl of acetate buffer pH 4.6).

Sample solution for solubilities of up to 10 g/l in water: About 5 mg of the active compound are weighed accurately into a 2 ml Eppendorf Safe-Lock tube (Eppendorf Art. No. 0030 120.094), and water is added to a concentration of 5 g/l (for example 5 mg of active compound+500 µl of water).

Practice:

The sample solutions prepared in this manner are shaken at 1400 rpm in a temperature-adjustable shaker (for example Eppendorf Thermomixer comfort Art. No. 5355 000.011 with interchangeable block Art. No. 5362.000.019) at 20° C. for 24 hours. In each case 180 µl are taken from these solutions and transferred into Beckman Polyallomer centrifuge tubes (Art. No. 343621). These solutions are centrifuged at about 223 000*g for 1 hour (for example Beckman Optima L-90K ultracentrifuge with type 42.2 Ti rotor at 42 000 rpm). From each of the sample solutions, 100 µl of the supernatant are removed and diluted 1:5, 1:100 and 1:1000 with the respective solvent used (water, PBS buffer 7.4 or acetate buffer pH 4.6). From each dilution, a sample is transferred into a vessel suitable for HPLC analysis.

Analysis:

The samples are analysed by RP-HPLC. Quantification is carried out using a two-point calibration curve of the test compound in DMSO. The solubility is expressed in mg/l.

Analysis Sequence:
Calibration solution 2.5 mg/ml
Calibration solution 20 µg/ml
Sample solution 1:5
Sample solution 1:100
Sample solution 1:1000
HPLC Method for Acids:

Agilent 1100 with DAD (G1315A), quat. pump (G1311A), autosampler CTC HTS PAL, degasser (G1322A) and column thermostat (G1316A); column: Phenomenex Gemini C18, 50×2 mm, 5µ; temperature: 40° C.; mobile phase A: water/phosphoric acid pH 2; mobile phase B: acetonitrile; flow rate: 0.7 ml/min; gradient: 0-0.5 min 85% A, 15% B; ramp: 0.5-3 min 10% A, 90% B; 3-3.5 min 10% A, 90% B; ramp: 3.5-4 min 85% A, 15% B; 4-5 min 85% A, 15% B.

HPLC Method for Bases:

Agilent 1100 with DAD (G1315A), quat. pump (G1311A), autosampler CTC HTS PAL, degasser (G1322A) and column thermostat (G1316A); column: VDSoptilab Kromasil 100 C18, 60×2.1 mm, 3.5µ; temperature: 30° C.; mobile phase A: water+5 ml perchloric acid/l; mobile phase B: acetonitrile; flow rate: 0.75 ml/min; gradient: 0-0.5 min 98% A, 2% B; ramp: 0.5-4.5 min 10% A, 90% B; 4.5-6 min 10% A, 90% B; ramp: 6.5-6.7 min 98% A, 2% B; 6.7-7.5 min 98% A, 2% B.

d) Determination of Pharmacokinetics (In Vivo)

To determine the in vivo pharmacokinetics, the test substances are dissolved in various formulating compositions (for example plasma, ethanol, DMSO, PEG400, etc.) or mixtures of these solubilizers and administered intravenously or perorally to mice, rats, dogs or monkeys. Intravenous administration is carried out either as a bolus injection or as an infusion. The doses administered are in the range from 0.1 to 5 mg/kg. Blood samples are taken by means of a catheter or as sacrifice plasma at various times over a period of up to 26 h. Furthermore, in some cases, samples of organs, tissue and urine are also taken. Quantitative determination of the substances in the test samples takes place using calibration samples adjusted in the matrix in question. Proteins present in the samples are removed by precipitation with acetonitrile or methanol. The samples are then fractionated by HPLC using reversed-phase columns in a 2300 HTLC system (Cohesive Technologies, Franklin, Mass., USA). The HPLC system is coupled via a turbo ion spray interface to an API 3000 Triple Quadropole mass spectrometer (Applied Biosystems, Darmstadt, Germany). The plasma concentration time course is analysed using a validated kinetic analysis program.

The affinity of a substance for a transport protein is examined by in vitro testing in a flux assay using Caco-2 cells or cells which are overexpressed in a specific transporter (Troutman M D, Thakker D R, Pharm. Res. 20 (8) 1210-1224 (2003); Schwab D, Fischer H, Tabatabaei A, Poli S, Huwyler J, J. Med. Chem. 46, 1716-1725 (2003); Merino G, Jonker J W, Wagenaar E, Pulido M M, Molina A J, Alvarez A I, Schinkel A H, Drug Metab. Dispos. 33 (5) 614-618 (2005)). To this end, the cells are cultivated on 24- or 96-well filter plates for 4 to 15 days. To determine the permeation, the substances in HEPES buffer are added either apically (A) or basally (B) to the cells, and the mixture is incubated for 2 h. After 0 h and 2 h, samples are taken from the cis- and trans-compartments and analysed by LC-MS/MS. The Papp value is calculated using the formula published by Schwab et al. A substance is classified as actively transported when the ratio of Papp (B–A)/Papp (A–B) is >2 or <0.5.

e) Determination of the Endotoxinaemia Activity (In Vivo)

The examination is carried out using rats or mice. In the mouse model (NMRI, male), LPS (*Escherichia coli* serotype 055:B5, Sigma-Aldrich) is injected 50 mg/kg intraperitoneally. The test substances are administered up to one hour prior to the LPS injection either intravenously via the tail vein, subcutaneously, intraperitoneally or orally using a stomach tube. Four hours after the LPS administration, the animal is anaesthetized (Ketavet/Rompun) and the abdomen is opened by surgery. Sodium citrate solution (3.2% w/v) (formula: body weight in g/13 times 100 µl) is injected into the lower vena carva, and a blood sample (about 1 ml) is taken after 30 sec. Various parameters, for example cellular blood components (in particular erythrocytes, leukocytes and platelets), lactate concentration, coagulation activation (TAT) or parameters of organ dysfunction or organ failure and mortality are determined from the blood.

f) Description of the Method Used for DIC Tests on Rats

LPS (*E. coli* 055 B5, manufactured by Sigma, dissolved in PBS) is administered to male Wistar rats at a dosage of 250 µg/kg intravenously into the tail vein (administration volume 2 ml/kg). The test substance is dissolved in PEG 400/$H_2O$ 60%/40% and administered orally (administration volume 5 ml/kg) 30 minutes prior to the LPS injection. 1, 5 or 4 hours after the LPS injection, the animals are exsanguinated by puncture of the heart in terminal anaesthesia (Trapanal® 100 mg/kg i.p.), and citrate plasma is obtained for the determination of fibrinogen, PT, TAT and platelet number. Optionally, serum is obtained for the determination of liver enzymes, kidney function parameters and cytokines. TNFα and IL-6 are determined using commercially available ELISAs (R&D Systems).

It is also possible to measure direct parameters of organ function, for example left- and right-ventricular pressures, arterial pressures, urine excretion, kidney perfusion and blood gases and acid/base state.

C. Exemplary Embodiments of Pharmaceutical Compositions

The compounds according to the invention can be converted into pharmaceutical preparations in the following ways:

Tablet:

Composition:

100 mg of the compound according to the invention, 50 mg of lactose (monohydrate), 50 mg of corn starch (native), 10 mg of polyvinylpyrrolidone (PVP 25) (from BASF, Ludwigshafen, Germany) and 2 mg of magnesium stearate.

Tablet weight 212 mg. Diameter 8 mm, radius of curvature 12 mm.

Preparation:

The mixture of the compound according to the invention, lactose and starch is granulated with a 5% strength solution (m/m) of PVP in water. The granules are dried and then mixed with the magnesium stearate for 5 minutes. This mixture is compressed using a conventional tablet press (see above for format of the tablet). As guideline, a compressive force of 15 kN is used for the compression.

Oral Suspension:
Composition:
1000 mg of the compound according to the invention, 1000 mg of ethanol (96%), 400 mg of Rhodigel® (xanthan gum from FMC, Pennsylvania, USA) and 99 g of water.

10 ml of oral suspension are equivalent to a single dose of 100 mg of the compound according to the invention.

Preparation:
The Rhodigel is suspended in ethanol, and the compound according to the invention is added to the suspension. The water is added while stirring. The mixture is stirred for about 6 h until the swelling of the Rhodigel is complete.

Oral Solution:
Composition:
500 mg of the compound according to the invention, 2.5 g of polysorbate and 97 g of polyethylene glycol 400.20 g of oral solution are equivalent to a single dose of 100 mg of the compound according to the invention.

Production:
The compound according to the invention is suspended in the mixture of polyethylene glycol and polysorbate while stirring. Stirring is continued until the compound according to the invention is completely dissolved.

i.v. Solution:
The compound according to the invention is dissolved at a concentration below saturation solubility in a physiologically acceptable solvent (for example isotonic sodium chloride solution, glucose solution 5% and/or PEG 400 solution 30%). The solution is sterilized by filtration and filled into sterile and pyrogen-free injection containers.

The invention claimed is:
1. A compound of the formula

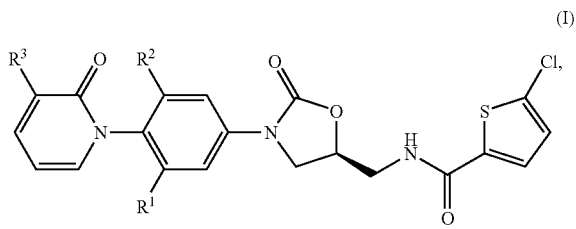

(I)

in which
$R^1$ represents chlorine, trifluoromethoxy, methyl, ethyl, n-propyl, methoxy, methoxymethyl or ethoxymethyl,
$R^2$ represents hydrogen or methyl, and
$R^3$ represents a group of the formula

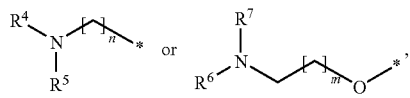

where
* is the point of attachment to the oxopyridine ring,
n represents the number 1, 2, 3 or 4,
m represents the number 1 or 2,
$R^4$ represents, methyl, ethyl, cyclopropyl, cyclobutyl, 2-hydroxyeth-1-yl, 3-hydroxyprop-1-yl, 2-methoxyeth-1-yl, 3-methoxyprop-1-yl, 4-hydroxycyclohex-1-yl, tetrahydrofuran-2-ylmethyl or 1,4-dioxan-2-ylmethyl,
$R^5$ represents hydrogen, methyl or ethyl, or
$R^4$ and $R^5$ together with the nitrogen atom to which they are attached form a pyrrolidin-1-yl ring, a 2-methoxymethylpyrrolidin-1-yl ring, a morpholin-4-yl ring, a 1,1-dioxothiomorpholin-4-yl ring, a 1,4-oxazepan-4-yl ring, a 4-methylpiperazin-1-yl or a 4-hydroxypiperidin-1-yl ring,
$R^6$ represents hydrogen, methyl, ethyl, cyclopropyl, cyclobutyl, 2-hydroxyeth-1-yl, 3-hydroxyprop-1-yl, 2-methoxyeth-1-yl, 3-methoxyprop-1-yl, 4-hydroxycyclohex-1-yl, tetrahydrofuran-2-ylmethyl or 1,4-dioxan-2-ylmethyl,
$R^7$ represents hydrogen, methyl or ethyl,
$R^6$ and $R^7$ together with the nitrogen atom to which they are attached form a pyrrolidin-1-yl ring, a 2-methoxymethylpyrrolidin-1-yl ring, a morpholin-4-yl ring, a 1,1-dioxothiomorpholin-4-yl ring, a 1,4-oxazepan-4-yl ring, a 4-methylpiperazin-1-yl or a 4-hydroxypiperidin-1-yl ring,
or one of its salt.

2. A compound according to claim 1, wherein
$R^1$ represents chlorine, trifluoromethoxy, methyl, ethyl, n-propyl, methoxy or methoxymethyl,
$R^2$ represents hydrogen or methyl, and
$R^3$ represents a group of the formula

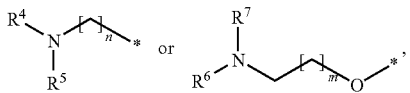

where
* is the point of attachment to the oxopyridine ring,
n is the number 1, 2 or 3,
m represents the number 1 or 2,
$R^4$ represents, methyl, ethyl, cyclopropyl, cyclobutyl, 2-hydroxyeth-1-yl, 3-hydroxyprop-1-yl, 2-methoxyeth-1-yl, 3 -methoxyprop-1-yl, 4-hydroxycyclohex-1-yl, tetrahydrofuran-2-ylmethyl or 1,4-dioxan-2-ylmethyl,
$R^5$ represents hydrogen, methyl or ethyl, or
$R^4$ and $R^5$ together with the nitrogen atom to which they are attached form a pyrrolidin-1-yl ring, a 2-methoxymethylpyrrolidin-1-yl ring, a morpholin-4-yl ring, a 1,1-dioxothiomorpholin-4-yl ring, a 1,4-oxazepan-4-yl ring, a 4-methylpiperazin-1-yl or a 4-hydroxypiperidin-1-yl ring,
$R^6$ represents hydrogen, methyl, ethyl, cyclopropyl, cyclobutyl, 2-hydroxyeth-1-yl, 3-hydroxyprop-1-yl, 2-methoxyeth-1-yl, 3-methoxyprop-1-yl, 4-hydroxycyclohex-1-yl, tetrahydrofuran-2-ylmethyl or 1,4-dioxan-2-ylmethyl,
$R^7$ represents hydrogen, methyl or ethyl, $R^6$ and $R^7$ together with the nitrogen atom to which they are attached form a pyrrolidin-1-yl ring, a 2-methoxymethylpyrrolidin-1-yl ring, a morpholin-4-yl ring, a 1,1-dioxothiomorpholin-4-yl ring, a 1,4-oxazepan-4-yl ring, a 4-methylpiperazin-1-yl or a 4-hydroxypiperidin-1-yl ring,
or one of its salts.

3. A compound according to claim 1, wherein
$R^1$ represents methyl, ethyl, n-propyl, methoxy or methoxymethyl,
$R^2$ represents hydrogen or methyl, and $R^3$ represents a group of the formula

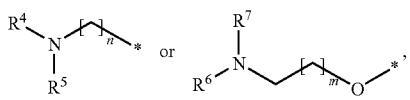

where
* is the point of attachment to the oxopyridine ring,
n is the number 1, 2 or 3,
m represents the number 1 or 2,
$R^4$ represents, methyl, ethyl, cyclopropyl, cyclobutyl, 2-hydroxyeth-1-yl, 3-hydroxyprop-1-yl, 2-methoxyeth-1-yl, 3-methoxyprop-1-yl, 4-hydroxycyclohex-1-yl, tetrahydrofuran-2-ylmethyl or 1,4-dioxan-2-ylmethyl,
$R^5$ represents hydrogen, methyl or ethyl,
$R^6$ represents hydrogen, methyl, ethyl, cyclopropyl, cyclobutyl, 2-hydroxyeth-1-yl, 3-hydroxyprop-1-yl, 2-methoxyeth-1-yl, 3-methoxyprop-1-yl, 4-hydroxycyclohex-1-yl, tetrahydrofuran-2-ylmethyl or 1,4-dioxan-2-ylmethyl,
$R^7$ represents hydrogen, methyl or ethyl,
or one of its salts.

4. A compound according to claim 1, wherein
$R^1$ represents methyl or methoxy,
$R^2$ represents hydrogen, or
$R^1$ represents methyl,
$R^2$ represents methyl, and
$R^3$ represents a group of the formula

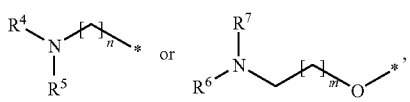

where
* is the point of attachment to the oxopyridine ring,
n represents the number 2,
m represents the number 1,
$R^4$ represents 2-hydroxyeth-1-yl or 4-hydroxycyclohex-1-yl,
$R^5$ represents hydrogen,
$R^6$ represents 2-hydroxyeth-1-yl or 4-hydroxycyclohex-1-yl,
$R^7$ represents hydrogen,
or one of its salts.

5. A compound according to claim 1, wherein
$R^1$ represents methoxymethyl,
$R^2$ represents hydrogen, or
$R^1$ represents methyl,
$R^2$ represents methyl, and
$R^3$ represents a group of the formula

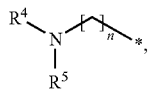

where
* is the point of attachment to the oxopyridine ring,
n represents the number 2,
$R^4$ represents 2-hydroxyeth-1-yl or 4-hydroxycyclohex-1-yl,
$R^5$ represents hydrogen,
or one of its salts.

6. A compound according to claim 1, wherein
$R^1$ represents methyl,
$R^2$ represents hydrogen, or
$R^1$ represents methyl,
$R^2$ represents methyl, and
$R^3$ represents a group of the formula

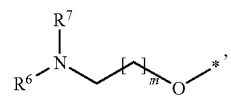

where
* is the point of attachment to the oxopyridine ring,
m represents the number 1,
$R^6$ represents 2-hydroxyeth-1-yl or 4-hydroxycyclohex-1-yl,
$R^7$ represents hydrogen,
or one of its salts.

7. A process for preparing a compound of the formula (I) or one or its salts according to claim 1, comprising:

[A] reacting a compound of the formula

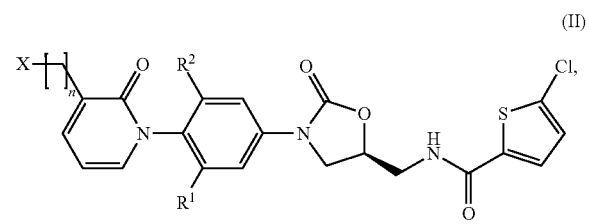
(II)

in which n, $R^1$ and $R^2$ have the meaning given in claim 1, and
X represents hydroxyl or bromine,
with a compound of the formula

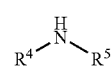
(III)

in which $R^4$ and $R^5$ have the meaning given in claim 1,
to give a compound of the formula

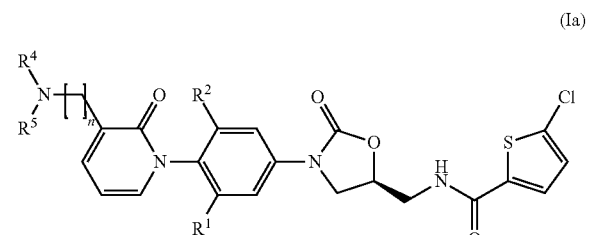
(Ia)

in which n, $R^1$, $R^2$, $R^4$ and $R^5$ have the meaning given in claim 1, or

[B] reacting a compound of the formula

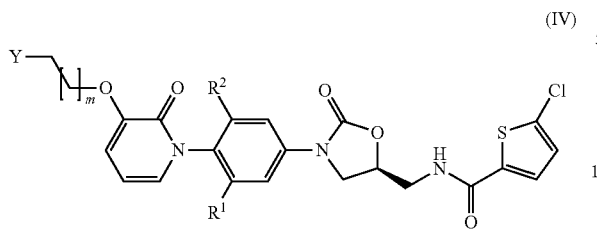

(IV)

in which m, $R^1$ and $R^2$ have the meaning given in claim 1, and

Y represents hydroxyl or chlorine, with a compound of the formula

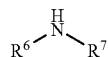

(V)

in which $R^6$ and $R^7$ have the meaning given in claim 1, to give a compound of the formula

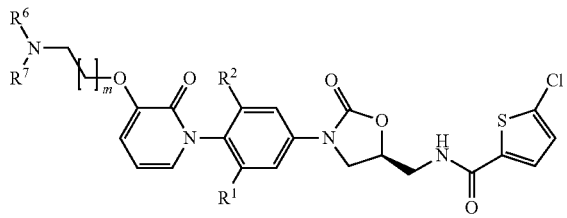

(Ib)

in which m, $R^1$, $R^2$, $R^6$ and $R^7$ have the meaning given in claim 1.

8. A pharmaceutical composition comprising a compound according to claim 1 and an inert nontoxic pharmaceutically acceptable auxiliary.

9. A pharmaceutical composition comprising a compound according to claim 1 in combination with a further active compound.

10. A method for the treatment and/or prophylaxis of thromboembolic disorders comprising administering to a human or animal in need thereof an anticoagulatory effective amount of at least one compound according to claim 1.

11. A method for preventing blood coagulation in vitro, wherein an anticoagulatory effective amount of a compound according to claim 1 is added.

\* \* \* \* \*